(12) United States Patent
Tapolsky et al.

(10) Patent No.: US 8,557,823 B2
(45) Date of Patent: Oct. 15, 2013

(54) FAMILY OF PFKFB3 INHIBITORS WITH ANTI-NEOPLASTIC ACTIVITIES

(75) Inventors: Gilles Tapolsky, Louisville, KY (US);
Pooran Chand, Birmingham, AL (US);
John O. Trent, Louisville, KY (US);
Sucheta Telang, Louisville, KY (US);
Brian F. Clem, Louisville, KY (US);
Jason A. Chesney, Louisville, KY (US)

(73) Assignees: Advanced Cancer Therapeutics, LLC, Louisville, KY (US); University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/307,552

(22) Filed: Nov. 30, 2011

(65) Prior Publication Data

US 2012/0177749 A1    Jul. 12, 2012

Related U.S. Application Data

(63) Continuation-in-part of application No. 12/141,751, filed on Jun. 18, 2008, now Pat. No. 8,088,385.

(60) Provisional application No. 60/936,030, filed on Jun. 18, 2007.

(51) Int. Cl.
*A01N 43/42* (2006.01)
*A61K 31/47* (2006.01)
*A61K 31/497* (2006.01)
*C07D 215/12* (2006.01)
*C07D 215/14* (2006.01)

(52) U.S. Cl.
USPC ....... 514/253.08; 514/311; 514/314; 546/174

(58) Field of Classification Search
None
See application file for complete search history.

(56) References Cited

PUBLICATIONS

Li et al. In vitro antimalarial activity of chalcones and their derivatives. J. Med. Chem. 1995, 38, 5031-5037.*
Chia et al. Synthesis and anti-inflammatory structure-activity relationsihps of thiazine-quinoline-quinones: inhibitors of the neutrophil respiratory burst in a model of acute gouty arthritis. Bioorganic & Medicinal Chemistry, 16, 2008, 9432-9442.*
Williams et al. (Foye's Principles of Medicinal Chemistry, 5th edition, pp. 59-63, 2002).*

* cited by examiner

*Primary Examiner* — Anna Pagonakis
(74) *Attorney, Agent, or Firm* — Dinsmore & Shohl LLP

(57) ABSTRACT

A methods and compounds for inhibiting 6-phosphofructo-2-kinase/fructose-2,6-bisphosphatase 3 (PFKFB3) are described. Also described are methods of inhibiting cell proliferation, treating cancer, and screening compounds to determine their ability to inhibit PFKFB3.

3 Claims, 45 Drawing Sheets

Plasma versus concentration profile for PFK-070 (5 mg/kg IV) in Balbc mice

Plasma versus concentration profile for PFK-0141 (5 mg/kg IV) in Balbc mice

Plasma versus concentration profile for PFK-141 (5 mg/kg IV) in SD rats

Plasma versus concentration profile for PFK-141 (5 mg/kg IV) in Beagle dogs (n=3)

Plasma versus concentration profile for PFK-151 (5 mg/kg IV) in Balbc mice

Plasma versus concentration profile for PFK-154 (5 mg/kg IV) in Balbc mice

PFK-070, efficacy profile in the LLC model at 25/35 mg/kg IP
Top curve is vehicle; bottom curve is ACT-PFK-070

PFK-141, efficacy Profile in U87MG model at 20 mg/kg IP (top curve is control group; lower curve is treated group, PFK-141 at 20 mg/kg)

PFK-141, efficacy profile in the CT26 colon cancer murine model at 20 / 23 mg/kg IP (top curve is control group; lower curve is treated group)

FAMILY OF PFKFB3 INHIBITORS WITH ANTI-NEOPLASTIC ACTIVITIES

CROSS REFERENCE TO RELATED APPLICATIONS

This application is a continuation-in-part of U.S. application Ser. No. 12/141,751, filed Jun. 18, 2008, which is based on and claims priority to U.S. Provisional Application Ser. No. 60/936,030, filed Jun. 18, 2007, each of which is incorporated by reference herein in its entirety.

GOVERNMENT INTEREST

This presently disclosed subject matter was made with U.S. Government support under Grant No. PCF OGMB04-1166 awarded by the U.S. Department of Defense. Thus, the U.S. Government has certain rights in the presently disclosed subject matter.

TECHNICAL FIELD

The presently disclosed subject matter relates to methods and compounds for reducing glycolytic flux. More particularly, the presently disclosed subject matter relates to aza chalcones and analogs thereof that inhibit 6-phosphofructo-2-kinase/fructose-2,6-bisphosphatase 3 (PFKFB3), an inducible isozyme of 6-phosphofructo-2-kinase (PFK-2). Methods of using the compounds to reduce glycolytic flux, to inhibit cell proliferation, and to treat cancer are described. Also described is a method of screening compounds for their ability to inhibit PFKFB3.

ABBREVIATIONS

2-DG=2-deoxyglucose
3-BrPA=3-bromopyruvate
3PO=3-(3-pyridinyl)-1-(4-pyridinyl)-2-propen-1-one
AA=amino acid
ATP=adenosine triphosphate
Ci=curie
DMSO=dimethyl sulfoxide
DNA=deoxyribonucleic acid
DNEM=Dulbecco's Modified Eagle Medium
EDTA=ethylenediaminetetraacetic acid
F2,6BP=fructose-2,6-bisphosphate
F6P=fructose-6-phosphate
HIF-1=hypoxia inducible factor 1
ht=human telomerase
LDH=lactate dehydrogenase
LT=large T antigen
μM=micromolar
mg=milligram
mL=milliliter
min=minute
ng=nanogram
NHBE=Normal Human Bronchial Epithelial
Ni=nickel
nm=nanometer
NTA=nitrilotriacetic acid
PBS=phosphate buffered saline
PEP=phophoenolpyruvate
PFK-1=6-phosphofructo-1-kinase
PKF-2=6-phosphofructo-2-kinase
PFKFB3=6-phosphofructo-2-kinase/fructose-2,6-bisphosphatase 3
PK=pyruvate kinase
PMSF=phenylmethylsulphonyl fluoride
PRPP=5-phospho-D-ribosyl-1-pyrophosphate
RNA=ribonucleic acid
SLN=Sybyl line notation
STD=standard deviation

BACKGROUND

The glycolytic pathway is a fundamental anaerobic pathway for sugar metabolism in eukaryotic cells. Glycolysis has a dual role, to degrade sugars to generate energy (ATP) and to provide building blocks for synthetic reactions. The rate of conversion of glucose into pyruvate is regulated to meet these two major cellular needs. In particular, enzymes such as hexokinase, phosphofructokinase and pyruvate kinase, which catalyze irreversible reactions in the glycolytic process, are regulated as control points in glycolysis.

In 1930, Warburg pointed out that tumors have a high rate of anaerobic glycolysis and do not show a decreased glycolytic rate even at relatively high oxygen concentrations. This loss of regulatory control (i.e., the Pasteur effect) has come to be called the Warburg effect. Since then, subsequent studies have consistently corroborated the inherent nature of cancer to involve: a) rapid consumption of glucose; b) robust glycolytic activity (see Maublant et al., *Bull Cancer*, 85, 935-950 (1998)); c) rapid cell proliferation (see Chesney et al., *Proc Natl Acad Sci USA*, 96, 3047-3052 (1999)); d) production and accumulation of lactic acid (see Baggetto, *Biochimie*, 74, 959-974 (1992)); and e) a low extracellular pH with depleted glucose levels circumscribing the perimeter of the tumor. See U.S. Patent Application Publication No. 20060035981.

Due to cancer cells' metabolic shift to increased glycolytic flux for energy and production of macromolecule precursors, inhibition of glycolysis has emerged as a potential targeted anti-neoplastic strategy. Over the past several decades, various small molecules have been identified as possessing anti-tumor characteristics by acting through inhibition of the glycolytic pathway. Two in particular, 3-bromopyruvate (3-BrPA) and 2-deoxyglucose (2-DG), both of which target hexokinase, have been demonstrated to exhibit cytotoxicity towards transformed cells with mitochondrial respiratory defects or under hypoxia. See Xu et al., *Cancer Res.*, 65, 613-621 (2005); Lui et al., *Biochemistry*, 40, 5542-5547 (2001); and Maher et al., *Cancer Chemother. Pharmacol.*, 53, 116-122 (2004). The anti-neoplastic agent Imatinib (i.e., Gleevec®, Novartis Pharmaceuticals Incorporation, East Hanover, N.J., United States of America) has also been demonstrated to suppress hexokinase.

There remains a need for additional anti-cancer therapeutics, particularly those which target neoplastic cells via mechanisms related to the increased glycolytic flux associated with cancers. There also remains a need for additional methods of screening compounds to determine their ability to inhibit the enzymes associated with glycolysis.

SUMMARY

The presently disclosed subject matter provides a method of inhibiting 6-phosphofructo-2-kinase/fructose-2,6-bisphosphatase 3 (PFKFB3), the method comprising contacting PFKFB3 with an inhibitory compound. In some embodiments, the method comprises contacting PFKFB3 with a compound of Formula (I):

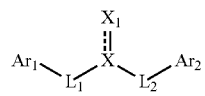

(I)

wherein:

X is C or CH;

$X_1$ is selected from the group consisting of O, S, $NR_1$, $C(R_2)_2$, $OR_3$, $SR_4$, $NR_5R_6$, and $C(R_7)_3$, wherein $R_1$, $R_3$, $R_4$, $R_5$ and $R_6$ are each independently selected from the group consisting of H, alkyl, aryl, aralkyl, and acyl, and each $R_2$ and $R_7$ is independently selected from the group consisting of H, halo, hydroxyl, alkoxy, alkyl, aralkyl, and aryl;

$L_1$ can be present or absent, and when present is selected from the group consisting of O, S, $NR_8$, alkylene, and substituted alkylene, wherein $R_8$ is selected from the group consisting of H, alkyl, aryl, and aralkyl;

$L_2$ can be present or absent, and when present is selected from the group consisting of O, S, $NR_9$, alkylene, substituted alkylene, and a trivalent linking group, wherein $R_9$ is selected from the group consisting of H, alkyl, aryl, and aralkyl, and the trivalent linking group comprises one atom bonding to $Ar_2$, a second atom bonding to X, and a third atom bonding to one of the group consisting of $Ar_1$ and $Ar_2$.

$Ar_1$ and $Ar_2$ are independently selected from the group consisting of aryl, substituted aryl, heteroaryl, and substituted heteroaryl.

In some embodiments, at least one of $Ar_1$ and $Ar_2$ is azaaryl. In some embodiments, at least one of $Ar_1$ and $Ar_2$ is selected from the group consisting of pyridine, substituted pyridine, quinoline, substituted quinoline, isoquinoline, and substituted isoquinoline.

In some embodiments, $L_1$ is absent. In some embodiments, $L_2$ is present and is $C_2$ alkylene.

In some embodiments, the compound of Formula (I) has a structure of Formula (II):

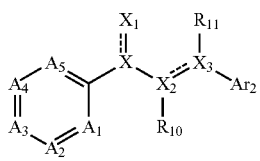

(II)

wherein:

X, $X_2$, and $X_3$ are each C or CH;

$X_1$ is selected from the group consisting of O, S, $NR_1$, $C(R_2)_2$, $OR_3$, $SR_4$, $NR_5R_6$, and $C(R_7)_3$, wherein $R_1$, $R_3$, $R_4$, $R_5$ and $R_6$ are each independently selected from the group consisting of H, alkyl, aryl, aralkyl, and acyl, and each $R_2$ and $R_7$ is independently selected from the group consisting of H, halo, hydroxyl, alkoxy, alkyl, aralkyl, and aryl;

$R_{10}$ is selected from the group consisting of H, alkyl, halo, cyano, hydroxyl, aryl, and aralkyl;

$R_{11}$ is selected from the group consisting of H, alkyl, halo, cyano, hydroxyl, aryl, and aralkyl;

$A_1$, $A_2$, $A_3$, $A_4$, and $A_5$ are each independently N or $CR_{12}$, wherein each $R_{12}$ is independently selected from the group consisting of H, alkyl, halo, nitro, cyano, hydroxyl, mercapto, amino, alkylamino, dialkylamino, carboxyl, acyl, carbamoyl, alkylcarbamoyl, dialkylcarbamoyl, sulfate, and a group having the structure:

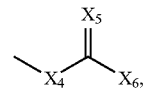

wherein:

$X_4$ is $NR_{14}$, wherein $R_{14}$ is selected from the group consisting of H, alkyl, hydroxyl, aralkyl, and aryl;

$X_5$ is selected from the group consisting of O, S, $C(R_{15})_2$, and $NR_{14}$, wherein each $R_{15}$ is independently selected from the group consisting of H, hydroxyl, alkoxy, alkyl, aralkyl, and aryl; and $X_6$ is selected from H, alkyl, aralkyl, aryl, heteroaryl, alkylamino, dialkylamino, and alkoxy;

or wherein $R_{10}$ and one $R_{12}$ are together alkylene;

$Ar_2$ is selected from the group consisting of

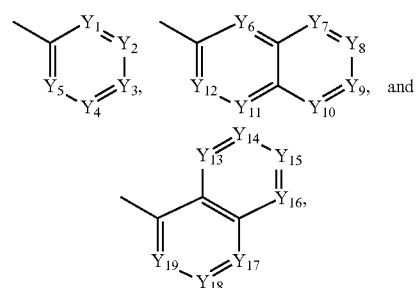

wherein:

each $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, and $Y_{19}$ is independently selected from the group consisting of N and $CR_{13}$, wherein each $R_{13}$ is independently selected from the group consisting of H, alkyl, halo, nitro, cyano, hydroxyl, mercapto, amino, alkylamino, dialkylamino, carboxyl, acyl, carbamoyl, alkylcarbamoyl, dialkylcarbamoyl, sulfate, and a group having the structure:

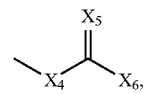

wherein:

$X_4$ is $NR_{14}$, wherein $R_{14}$ is selected from the group consisting of H, alkyl, hydroxyl, aralkyl, and aryl;

$X_5$ is selected from the group consisting of O, S, $C(R_{15})_2$, and $NR_{14}$, wherein each $R_{15}$ is independently selected from the group consisting of H, hydroxyl, alkoxy, alkyl, aralkyl, and aryl; and $X_6$ is selected from H, alkyl, aralkyl, aryl, heteroaryl, alkylamino, dialkylamino, and alkoxy;

or wherein $R_{10}$ and one $R_{13}$ are together alkylene; and wherein at least one of $A_1$, $A_2$, $A_3$, $A_4$, $A_5$, $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, and $Y_{19}$ is N;

or a pharmaceutically acceptable salt thereof.

In some embodiments, $X_1$ is O and X is C.

In some embodiments, $Ar_2$ is:

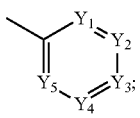

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound of Formula (II) has a structure of Formula (III):

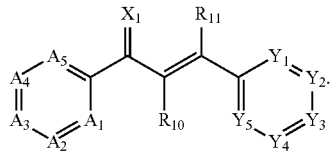

(III)

In some embodiments, $X_1$ is O. In some embodiments, $R_{10}$ and $R_{11}$ are each H.

In some embodiments, the compound of Formula (III) is selected from the group consisting of:

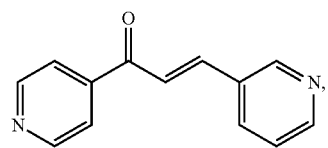

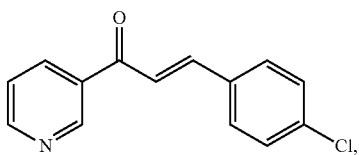

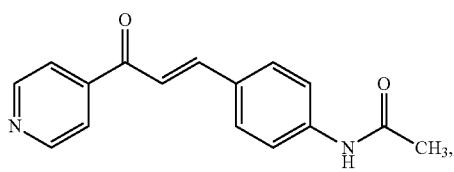

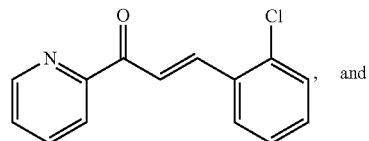, and

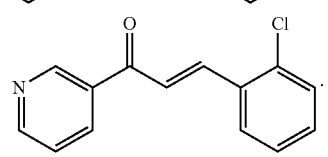.

In some embodiments, $Ar_2$ is:

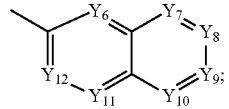

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound of Formula (II) has a structure of Formula (IV):

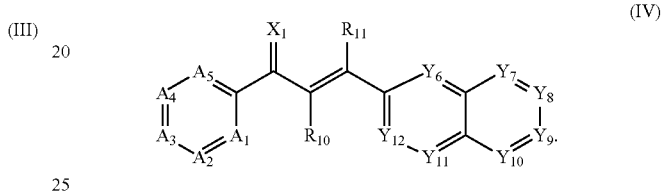

(IV)

In some embodiments, $X_1$ is O. In some embodiments, $R_{10}$ and $R_{11}$ are each H. In some embodiments, the compound of Formula (IV) is

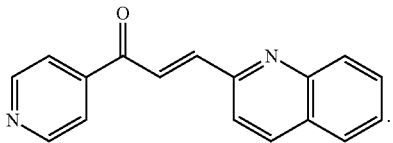

In some embodiments, $Ar_2$ is

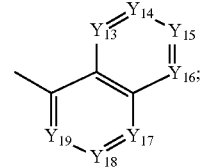

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound of Formula (II) has a structure of Formula (V):

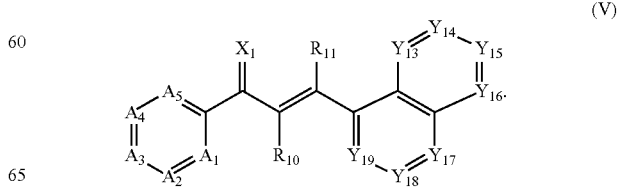

(V)

In some embodiments, $X_1$ is O. In some embodiments, $R_{10}$ and $R_{11}$ are each H. In some embodiments, the compound of Formula (V) is:

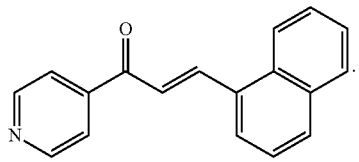

In some embodiments, the compound of Formula (II) has the structure of Formula (VI):

Formula (VI)

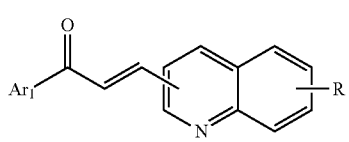

wherein $Ar_1$ is substituted or unsubstituted and is selected from the group consisting of phenyl, 2-pyridyl, 3-pyridyl, 4-pyridyl, 3,5-pyrimidinyl, and 2,4-pyrimidinyl, wherein the $Ar_1$ substitutions are selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof; and R is one, two or three substitutions at any position on the quinoline ring, wherein the R substitutions are independently selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof.

In another embodiment, the compound of Formula (II) has the structure of Formula (VII):

Formula (VII)

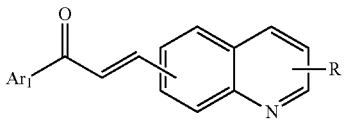

wherein $Ar_1$ is substituted or unsubstituted and is selected from the group consisting of phenyl, 2-pyridyl, 3-pyridyl, 4-pyridyl, 3,5-pyrimidinyl, and 2,4-pyrimidinyl, wherein the $Ar_1$ substitutions are selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof; and R is one, two or three substitutions at any position on the quinoline ring, wherein the R substitutions are independently selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof.

In some embodiments, the presently disclosed subject matter provides a method of reducing glycolytic flux in a cell, the method comprising contacting the cell with an effective amount of a PFKFB3 inhibitor. In some embodiments, the presently disclosed subject matter provides a method of reducing glycolytic flux in a cell, the method comprising contacting the cell with an effective amount of a compound of Formula (I).

In some embodiments, the presently disclosed subject matter provides a method of reducing proliferative capacity in a cell, the method comprising contacting the cell with an effective amount of a PFKFB3 inhibitor. In some embodiments, the presently disclosed subject matter provides a method of reducing proliferative capacity in a cell, the method comprising contacting the cell with an effective amount of a compound of Formula (II). In some embodiments, the compound comprises a group having the structure:

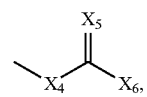

wherein $X_4$ is $NR_{14}$, wherein $R_{14}$ is selected from the group consisting of H, alkyl, hydroxyl, aralkyl, and aryl; $X_5$ is selected from the group consisting of O, S, $C(R_{15})_2$, and $NR_{14}$, wherein each $R_{15}$ is independently selected from the group consisting of H, hydroxyl, alkoxy, alkyl, aralkyl, and aryl; and $X_6$ is selected from H, alkyl, aralkyl, aryl, heteroaryl, alkylamino, dialkylamino, and alkoxy. In some embodiments, $X_5$ is O and $X_6$ is selected from H, alkyl, aralkyl, and aryl. In some embodiments, the compound is a compound of one of Formulas (IIIa), (IIIb), (IIIc), and (IIId):

(IIIa)

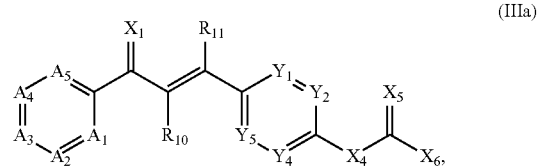

(IIIb)

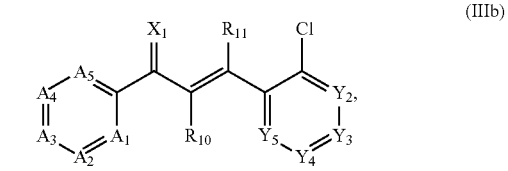

(IIIc)

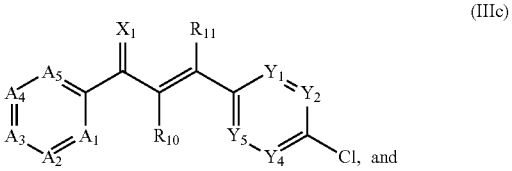

(IIId)

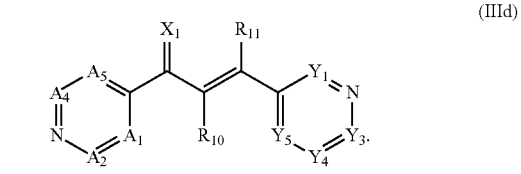

In some embodiments, the cell is a mammalian cell. In some embodiments, the cell is a human cell. In some embodiments, the cell is a cancer cell.

In some embodiments, the presently disclosed subject matter provides a method of treating a cancer in a subject in need of treatment thereof, the method comprising administering to the subject an effective amount of a PFKFB3 inhibitor. In some embodiments, the presently disclosed subject matter provides a method of treating a cancer in a subject in need of treatment thereof, the method comprising administering to the subject an effective amount of a compound of Formula (II). In some embodiments, the compound is a compound of one of Formulas (IIIa), (IIIb), (IIIc), and (IIId). In some embodiments, the subject is a mammal. In some embodiments, the subject is a human. In some embodiments, the cancer is selected from the group consisting of breast cancer, lung cancer, cervical cancer, skin cancer, and leukemia.

In some embodiments, the method further comprises administering to the subject one or more additional therapeutic compound. In some embodiments, the one or more additional therapeutic compound is an anti-cancer therapeutic. In some embodiments, the one or more additional therapeutic compound is selected from the group consisting of cisplatin and paclitaxel.

In some embodiments, the presently disclosed subject matter provides a method of screening a compound for having an ability to inhibit PFKFB3, the method comprising: providing a three-dimensional model of PFKFB3, the model comprising a fructose-6-phosphate (F6P) binding pocket of PFKFB3; providing a three-dimensional model of a compound; and screening the model of the compound against the model of PFKFB3 to determine a potential for the compound to contact one or more solvent accessible sites in the F6P binding pocket of PFKFB3. In some embodiments, the presently disclosed subject matter provides a method of screening a compound for having the ability to inhibit tumor growth. In some embodiments, screening the compound comprises screening a plurality of compound against a model of PFKFB3 to determine the potential for each of the plurality of compounds to contact one or more solvent accessible site in the F6P binding pocket of the PFKFB3.

Thus, it is an object of the presently disclosed subject matter to provide compounds that inhibit PFKFB3, thereby mediating glycolytic flux.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

DETAILED DESCRIPTION

Figure 1:
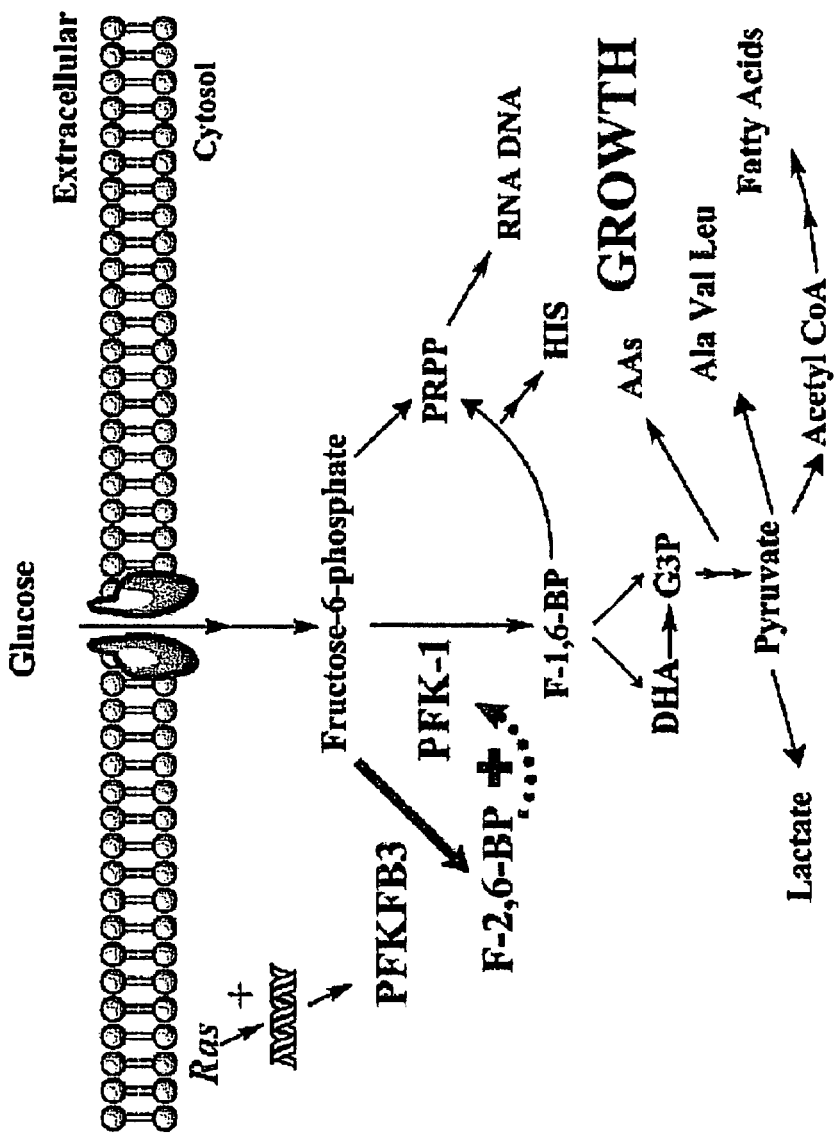
FIG. 1 is a schematic drawing illustrating pathways by which 6-phosphofructo-2-kinase/fructose-2,6-bisphosphatase 3 (PFKFB3) upregulates glycolytic flux through fructose-2,6-bisphosphate activation of PFK-1.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. DEFINITIONS

The term "cancer" as used herein refers to diseases caused by uncontrolled cell division and the ability of cells to metastasize, or to establish new growth in additional sites. The terms "malignant", "malignancy", "neoplasm", "tumor" and variations thereof refer to cancerous cells or groups of cancerous cells.

Specific types of cancer include, but are not limited to, skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

The term "competitive inhibitor" refers to an inhibitor whose binding to an enzyme prevents the binding of the enzyme's normal substrate.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

As used herein, the term "aza" refers to a heterocyclic ring structure containing at least one nitrogen atom. Specific examples of aza groups include, but are not limited to, pyrrolidine, piperidine, quinuclidine, pyridine, pyrrole, indole, purine, pyridazine, pyrimidine, and pyrazine.

The term "azaaryl" refers to a heterocyclic aryl group wherein one or more of the atoms of the aryl group ring or rings is nitrogen. Examples of azaaryl groups include monocyclic or bicyclic mono- or diazaaryl (i.e., an aryl group comprising two nitrogen atoms), which is unsubstituted or substituted by a member selected from the group consisting of lower alkyl, for example methyl, lower alkoxy, for example methoxy, and/or halogen, for example chlorine or bromine. Therefore, the term "azaaryl" refers to groups including, but not limited to, pyridine, pyridazine, pyrimidine, pyrazine, quinoline, quinaldine, quinoxaline, and substituted analogs thereof. In some embodiments, the azaaryl group is pyridyl, for example 2-, 3- or 4-pyridyl; quinolinyl or isoquinolinyl, for example 4-quinolinyl or 1-isoquinolinyl; imidazolyl; pyrimidinyl, for example 2- or 4-pyrimidinyl; pyridazinyl, for example 3-pyridazinyl; or pyrazinyl, for example 2-pyrazinyl.

A structure represented generally by a formula such as:

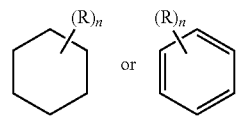

as used herein refers to a ring structure, for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

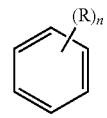

wherein n is an integer from 0 to 2 comprises compound groups including, but not limited to:

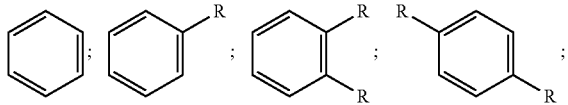

and the like.

A dashed line representing a bond in a chemical structure indicates that the bond can be either present or absent. For example, the group:

can refer to a group comprising a single bond or a double bond.

When a named atom or group is defined as being "absent," the named atom or group is replaced by a direct bond. When the linking group or spacer group is defined as being absent, the linking group or spacer group is replaced by a direct bond.

In some embodiments, the compounds of the presently disclosed subject matter contain a linking group. As used herein, the term "linking group" comprises a bivalent chemical moiety, including, but not limited to an alkylene group, which is bonded to two or more other chemical moieties, to form a stable structure. In some embodiments, a single atom, such as O or S, can serve as a linking group. In some embodiments, the linking group can include oxy or thio groups, such as, for example, methylenedioxyl (—O—CH$_2$—O—) or ethylenedioxyl (—O—CH$_2$CH$_2$—O—). In some embodiments, the linking group can be a divalent aryl group, such as a phenylene, furanyl, thienyl, or pyrrolyl radical.

The term "trivalent linking group" refers to a linking group that is links three groups or three sites (e.g., atoms) on one or more chemical groups. For example, the trivalent linking group can have the formula:

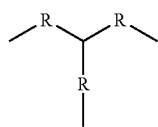

wherein each R is independently $C_0$-$C_6$ alkyl which can include one or more O, S, nitrogen or substituted nitrogen, or unsaturated bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents," including hydroxyl, halo, nitro, alkyl, aryl, aralkyl, carboxyl and the like. There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

As used herein, the term "acyl" refers to an organic carboxylic acid group wherein the —OH of the carboxyl group has been replaced with another substituent (i.e., as represented by RCO—, wherein R is an alkyl, aralkyl or aryl group as defined herein, including substituted alkyl, aralkyl, and aryl groups). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O–CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl–NR— group wherein acyl is as previously described and R is H or alkyl. Thus, the "acylamino" group can have the structure —NR—C(═O)—R', wherein R' is alkyl, aryl, aralkyl, and the like.

The term "amino" refers to the —$NH_2$ group.

The term "carbonyl" refers to the —(C═O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "aza" refers to a compound wherein a carbon atom is replaced by a nitrogen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term "chalcone" or "chalkone" refers to 1,3-diphenyl-1-propen-3

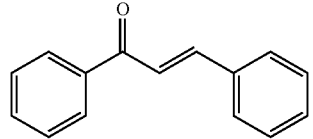 [SMILES: O=C(/C=C/c1ccccc1)c1ccccc1]

and to analogs thereof (e.g., to diaryl propenones, thia and aza analogues of diaryl propenones, and diarylpropanes,). The term "aza chalcone" refers to a chalcone comprising one or more nitrogen atoms. In particular, the aza chalcone can comprise one or more azaaryl groups.

When the term "independently selected" is used, the substituents being referred to (e.g., R groups, such as groups $R_1$ and $R_2$, or groups X and Y), can be identical or different. For example, both $R_1$ and $R_2$ can be substituted alkyls, or $R_1$ can be hydrogen and $R_2$ can be a substituted alkyl, and the like.

A named "R", "X", "A", "Ar", "Y" or "L" group will generally have the structure that is recognized in the art as corresponding to a group having that name, unless specified otherwise herein. For the purposes of illustration, certain representative "R," "X," "Y," "L," "Ar," and "A" groups as set forth above are defined below. These definitions are intended to supplement and illustrate, not preclude, the definitions that would be apparent to one of ordinary skill in the art upon review of the present disclosure.

II. GENERAL CONSIDERATIONS

Understanding the exact mechanisms by which neoplastic tissues bring about a metabolic shift to increased glycolytic flux has been the focus of intense investigation for some time. Increased glycolysis is achieved by a variety of factors including: a) substrate availability, b) expression of metabolic enzymes necessary for glycolytic flux, and c) levels of allosteric activators and inhibitors that act on particular points within the pathway. For example, it is thought that increased expression of glucose transporters, such as GLUT1, provide the excess supply of glucose needed to sustain an elevated glycolytic rate, while key rate-limiting enzymes such as hexokinase and phosphofructo-1-kinase (PFK1) have been revealed to be upregulated in neoplastic cells. See Vora et al., *Cancer Res.*, 45(7), 2993-3001 (1985); Macheda et al., *J. Cell Physiol.*, 202(3), 654-662 (2005); and Mathupala et al., *Oncogene*, 25(34), 4777-4786 (2006). Lastly, allosteric regulators of the glycolytic enzymes play a large role in the flux of glucose, primarily at the first irreversible, committed rate limiting step involving PFK1. See Van Schaftingen, et al., *Proc. Natl. Acad. Sci. USA*, 78(6), 3483-3486 (1981).

PFK1 activity has been observed to be increased in tumor cell lines, as well as in primary tumor tissues. Further, the introduction of oncogenic ras or src into Rat-1 fibroblasts or chick-embryo fibroblasts, respectively, results in higher PFK-1 activity. See Hennipman et al., *Tumour Biol.*, 8(5), 251-263 (1987); Kole, et al., *Arch. Biochem. Biophys.* 286(2), 586-590 (1991); and Sanchez-Martinez and Aragon, *FEBS Lett.*, 409(1), 86-90 (1997). However, the higher level of activation of PFK1 within the transformed cells was not due to greater protein expression, but was found to be due to increased production of fructose-2,6-bisphosphate (F2,6BP). See Kole, et al., *Arch. Biochem. Biophys.* 286(2), 586-590 (1991). Identified in the early 1980's, F2,6BP was found to be a potent allosteric activator of PFK1, capable of relieving the inhibitory effects of ATP by shifting the conformational equilibrium of PFK1 from a low to a high affinity state for its substrate, fructose-6-phosphate. See Van Schaftingen, et al., *Biochem. J.*, 192(3), 887-895 (1980); Van Schaftingen, et al., *Biochem. J.*, 192(3), 897-901 (1980); and Van Schaftingen, et al., *Proc. Natl. Acad. Sci., USA*, 78(6), 3483-3486 (1981). Therefore, upregulation of F2,6BP levels allows for neoplastic tissues to maintain high glycolytic output even in the presence of high energy production (i.e., physiological ATP levels). FIG. 1 illustrates how oncogenic ras is believed to increase the expression and activity of PFKFB3 in neoplastic cells, thereby leading to enhanced F2,6BP production, the activation of rate-limiting PFK-1, and ultimately, higher glycolytic flux and increased production of macromolecules including RNA, DNA, amino acids (AAs), and fatty acids.

F2,6BP levels within the cell are maintained by a family of bi-functional enzymes termed 6-phosphofructo-2-kinase/fructose-2,6-bisphosphatases (PFK-2/FBPases), and are encoded by four genes PFKFB1-4. PFKFB1, 2, and 4 are reported to be expressed within the liver/muscle, kidney/heart, and testes, respectively, and exhibit equal kinase to phosphatase activity. An inducible isoform of PFK-2 (reported as iPFK2, placental PFK2, ubiquitous PFK2, and PGR1) encoded by the PFKFB3 gene has been shown to be upregulated via mitogenic, inflammatory, and hypoxic stimuli, and displays a kinase to phosphatase ratio of 740:1 due to a point mutation within the phosphatase domain.

PFKFB3 has been observed to be over-expressed in many types of neoplastic tissues including: colon, prostate, lung, breast, pancreas, and ovary. See Atsumi, et al., *Cancer Res.*, 62, 5881-5887 (2002). The addition of oncogenic ras to immortalized mouse fibroblasts results in increased PFKFB3 expression, suggesting that PFKFB3 may be a vital component necessary for neoplastic transformation. Chesney and coworkers have demonstrated a suppression of K562 leukemia xenografts in athymic mice using anti-sense oligonucleotides against PFKFB3, while also observing a decrease in 5-phosphoribosyl-1-pyrophosphate (PRPP), which is a precursor to nucleotide biosynthesis. In heterozygous PFKFB3 (+/−) mouse fibroblasts subsequently immortalized and transformed with human telomerase, Large T antigen, and oncogenic H-ras$^{v12}$, F2,6BP production is reduced and glycolytic flux of glucose to lactate is suppressed. More importantly, lower levels of PFKFB3 in ras-transformed fibroblasts resulted in a loss of anchorage-independent growth in soft agar and a marked reduction in in vivo growth of tumors in athymic mice. See Telang et al., *Oncogene*, 25, 7225-7234 (2006). Separately, siRNA suppression of PFKFB3 in A549 lung carcinoma cells also caused a decrease in F2,6BP, and a loss in soft agar colony formation.

Disclosed herein for the first time is the observation that selectively targeting PFKFB3 with small molecule inhibitors is a strategy for novel anti-cancer therapeutics.

III. PFKFB3 INHIBITORS

The presently disclosed subject matter provides a method of inhibiting PFKFB3, the method comprising contacting PFKFB3 with an inhibitory compound. In some embodiments, the method comprises contacting PFKFB3 with a small molecule inhibitor.

In some embodiments, the presently disclosed subject matter provides a method of contacting PFKFB3 with a compound that inhibits or otherwise changes the activity of PFKFB3, wherein the compound is a compound of Formula (I):

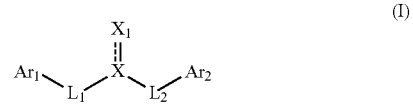

wherein:
X is C or CH;
$X_1$ is selected from the group consisting of O, S, $NR_1$, $C(R_2)_2$, $OR_3$, $SR_4$, $NR_5R_6$, and $C(R_7)_3$, wherein $R_1$, $R_3$, $R_4$, $R_5$ and $R_6$ are each independently selected from the group consisting of H, alkyl, aryl, aralkyl, and acyl, and each $R_2$ and $R_7$ is independently selected from the group consisting of H, halo, hydroxyl, alkoxy, alkyl, aralkyl, and aryl;

$L_1$ can be present or absent, and when present is selected from the group consisting of O, S, $NR_8$, alkylene, and substituted alkylene, wherein $R_8$ is selected from the group consisting of H, alkyl, aryl, and aralkyl;

$L_2$ can be present or absent, and when present is selected from the group consisting of O, S, $NR_9$, alkylene, substituted alkylene, and a trivalent linking group, wherein $R_9$ is selected from the group consisting of H, alkyl, aryl, and aralkyl, and the trivalent linking group comprises one atom bonding to $Ar_2$, a second atom bonding to X, and a third atom bonding to one of the group consisting of $Ar_1$ and $Ar_2$.

$Ar_1$ and $Ar_2$ are independently selected from the group consisting of aryl, substituted aryl, heteroaryl, and substituted heteroaryl.

In some embodiments the compound of Formula (I) is an aza chalcone.

In some embodiments, at least one of $Ar_1$ and $Ar_2$ are azaaryl. In some embodiments, both $Ar_1$ and $Ar_2$ are azaaryl. In some embodiments, at least one of $Ar_1$ and $Ar_2$ is selected from the group consisting of pyridine, substituted pyridine, quinoline, substituted quinoline, isoquinoline, and substituted isoquinoline.

In some embodiments, at least one of $Ar_1$ or $Ar_2$ is substituted with an acylamino group. In some embodiments, the compound of Formula (I) is an acylamino-substituted azachalcone.

In some embodiments, $Ar_1$ is an azaaryl group. In some embodiments, $Ar_1$ is 2-, 3-, or 4-pyridine or a substituted 2-, 3-, or 4-pyridine.

In some embodiments, $L_1$ is absent. In some embodiments, $L_2$ is present and is $C_2$ alkylene.

In some embodiments, the compound of Formula (I) has a structure of Formula (II):

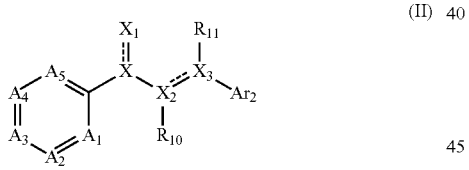

(II)

wherein:

X, $X_2$, and $X_3$ are each C or CH;

$X_1$ is selected from the group consisting of O, S, $NR_1$, $C(R_2)_2$, $OR_3$, $SR_4$, $NR_5R_6$, and $C(R_7)_3$, wherein $R_1$, $R_3$, $R_4$, $R_5$ and $R_6$ are each independently selected from the group consisting of H, alkyl, aryl, aralkyl, and acyl, and each $R_2$ and $R_7$ is independently selected from the group consisting of H, halo, hydroxyl, alkoxy, alkyl, aralkyl, and aryl;

$R_{10}$ is selected from the group consisting of H, alkyl, halo, cyano, hydroxyl, aryl, and aralkyl;

$R_{11}$ is selected from the group consisting of H, alkyl, halo, cyano, hydroxyl, aryl, and aralkyl;

$A_1$, $A_2$, $A_3$, $A_4$, and $A_5$, are each independently N or $CR_{12}$, wherein each $R_{12}$ is independently selected from the group consisting of H, alkyl, halo, nitro, cyano, hydroxyl, mercapto, amino, alkylamino, dialkylamino, carboxyl, acyl, carbamoyl, alkylcarbamoyl, dialkylcarbamoyl, sulfate, and a group having the structure:

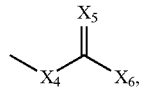

wherein:

$X_4$ is $NR_{14}$, wherein $R_{14}$ is selected from the group consisting of H, alkyl, hydroxyl, aralkyl, and aryl;

$X_5$ is selected from the group consisting of O, S, $C(R_{15})_2$, and $NR_{14}$, wherein each $R_{15}$ is independently selected from the group consisting of H, hydroxyl, alkoxy, alkyl, aralkyl, and aryl; and $X_6$ is selected from H, alkyl, aralkyl, aryl, heteroaryl, alkylamino, dialkylamino, and alkoxy;

or wherein $R_{10}$ and one $R_{12}$ are together alkylene;

$Ar_2$ is selected from the group consisting of

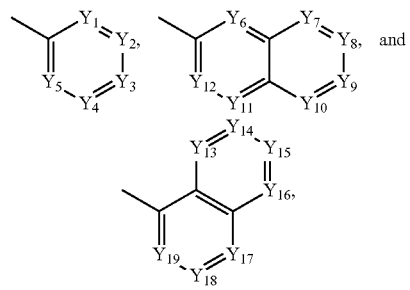

and wherein:

each $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, and $Y_{19}$ is independently selected from the group consisting of N and $CR_{13}$, wherein each $R_{13}$ is independently selected from the group consisting of H, alkyl, halo, nitro, cyano, hydroxyl, mercapto, amino, alkylamino, dialkylamino, carboxyl, acyl, carbamoyl, alkylcarbamoyl, dialkylcarbamoyl, sulfate, and a group having the structure:

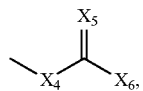

wherein:

$X_4$ is $NR_{14}$, wherein $R_{14}$ is selected from the group consisting of H, alkyl, hydroxyl, aralkyl, and aryl;

$X_5$ is selected from the group consisting of O, S, $C(R_{15})_2$, and $NR_{14}$, wherein each $R_{15}$ is independently selected from the group consisting of H, hydroxyl, alkoxy, alkyl, aralkyl, and aryl; and $X_6$ is selected from H, alkyl, aralkyl, aryl, heteroaryl, alkylamino, dialkylamino, and alkoxy;

or wherein $R_{10}$ and one $R_{13}$ are together alkylene; and wherein at least one of $A_1$, $A_2$, $A_3$, $A_4$, $A_5$, $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, and $Y_{19}$ is N;

or a pharmaceutically acceptable salt thereof.

In some embodiments, two of $A_1$, $A_2$, $A_3$, $A_4$, $A_5$, $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, and $Y_{19}$ are N.

In some embodiments, $X_1$ is O and X is C.

In some embodiments, $Ar_2$ is:

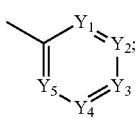

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound of Formula (II) has a structure of Formula (III):

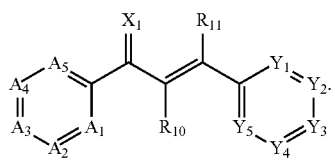

(III)

In some embodiments, $X_1$ is O. In some embodiments, $R_{10}$ and $R_{11}$ are each H.

In some embodiments, at least one of $Y_1$, $Y_2$, $Y_3$, $Y_4$, and $Y_5$ is $CR_{13}$, wherein $R_{13}$ is a group having the structure:

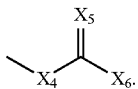

In some embodiments, $X_5$ is O and $X_6$ is selected from H, alkyl, aralkyl, and aryl, and $Ar_2$ is an acylamino-substituted aryl or heteroaryl group.

In some embodiments, the compound of Formula (III) is a compound of Formula (IIIa):

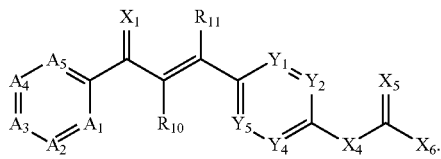

(IIIa)

In some embodiments, $A_3$ of the compound of Formula (IIIa) is N. In some embodiments, $A_3$ is N, each of $A_1$, $A_2$, $A_4$, and $A_5$ is $CR_{12}$, and each of $Y_1$, $Y_2$, $Y_4$, and $Y_5$ is $CR_{13}$.

In some embodiments, the compound of Formula (III) comprises at least one halo substituent. In some embodiments, the halo substituent is Cl. In some embodiments, the halo substituent is ortho to the carbon attached to the alkene.

In some embodiments, the compound of Formula (III) is a compound of Formula (IIIb):

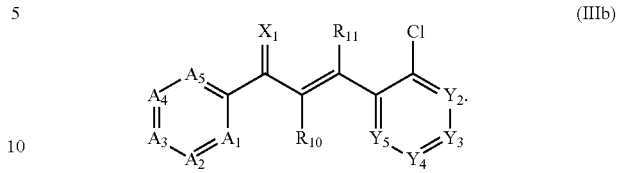

(IIIb)

In some embodiments, one of $A_4$ and $A_5$ of the compound of Formula (IIIb) is N. In some embodiments, one of $A_4$ and $A_5$ is N, each of $A_1$, $A_2$, and $A_3$ is $CR_{12}$, and each of $Y_2$, $Y_3$, $Y_4$, and $Y_5$ is $CR_{13}$.

In some embodiments, the halo substituent is para to the carbon attached to the alkene. In some embodiments, the compound of Formula (III) is a compound of Formula (IIIc):

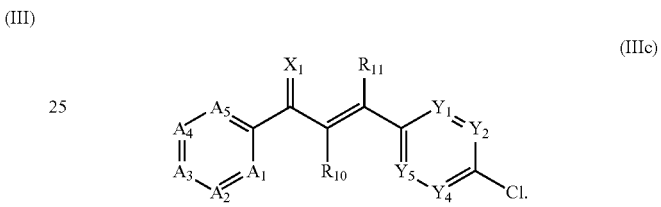

(IIIc)

In some embodiments, $A_2$ of the compound of Formula (IIIc) is N. In some embodiments, $A_2$ is N, each of $A_1$, $A_3$, $A_4$, and $A_5$ is $CR_{12}$, and each of $Y_1$, $Y_2$, $Y_4$, and $Y_5$ is $CR_{13}$.

In some embodiments, the compound of Formula (III) comprises two azaaryl groups. In some embodiments, the compound comprises one 4-pyridyl group and one 3-pyridyl group. In some embodiments, the compound of Formula (III) is a compound of Formula (IIId):

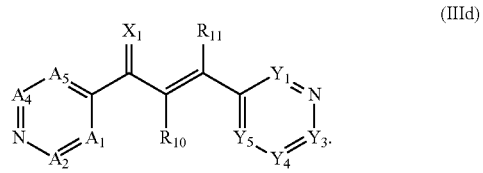

(IIId)

In some embodiments, each of $A_1$, $A_2$, $A_4$, and $A_5$ is $CR_{12}$, and each of $Y_1$, $Y_3$, $Y_4$, and $Y_5$ is $CR_{13}$.

In some embodiments, the compound of Formula (III) is selected from the group consisting of:

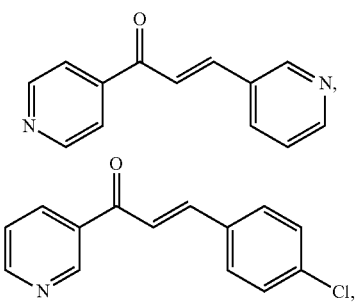

-continued

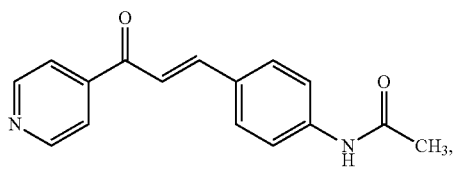

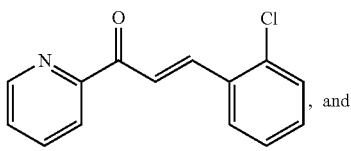, and

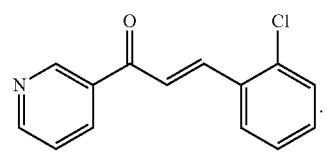.

In some embodiments, the compound of Formula (II) is a compound wherein $Ar_2$ is:

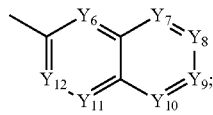

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound of Formula (II) has a structure of Formula (IV):

(IV)

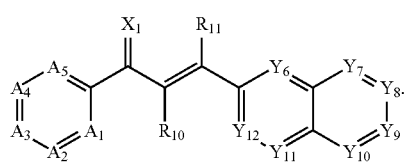

In some embodiments, the compound of Formula (IV) comprises two azaaryl groups. In some embodiments, $Y_6$ and $A_3$ are each N. In some embodiments each of $A_1$, $A_2$, $A_4$, and $A_5$ is $CR_{12}$ and each of $Y_7$, $Y_8$, $Y_9$, $Y_{10}$, $Y_{11}$, and $Y_{12}$ is $CR_{13}$. In some embodiments, the compound of Formula (IV) is

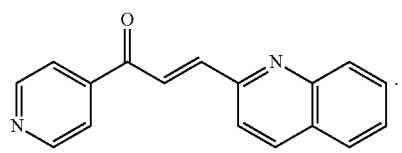 [SMILES: O=C(/C=C/c1ccc2ccccc2n1)c1ccncc1].

In some embodiments, the compound of Formula (II) is a compound wherein $Ar_2$ is

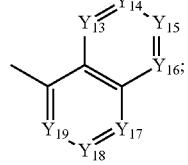

$X$, $X_2$, and $X_3$ are each C;

$X_1$ is selected from the group consisting of O, S, $NR_1$, and $C(R_2)_2$, wherein $R_1$, is selected from the group consisting of H and alkyl, and each $R_2$ is independently selected from the group consisting of H, halo, hydroxyl, alkoxy, and alkyl; and the compound has a structure of Formula (V):

(V)

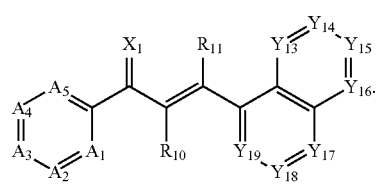

In some embodiments, $A_3$ is N. In some embodiments, the compound of Formula (V) is:

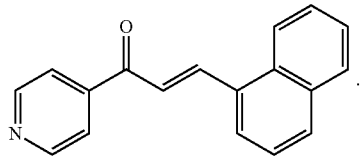 [SMILES: O=C(/C=C/c1cccc2ccccc12)c1ccncc1].

In some embodiments, the compound of Formula (II) has the structure of Formula (VI):

Formula (VI)

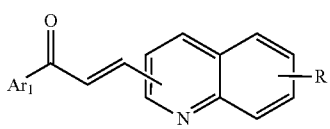

wherein $Ar_1$ is substituted or unsubstituted and is selected from the group consisting of phenyl, 2-pyridyl, 3-pyridyl, 4-pyridyl, 3,5-pyrimidinyl, and 2,4-pyrimidinyl, wherein $Ar_1$ substitutions are selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof; and R is one, two or three substitutions at any position on the quinoline ring, wherein the R substitutions are independently selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof.

In another embodiment, the compound of Formula (II) has the structure of Formula (VII):

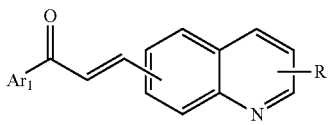

Formula (VII)

wherein $Ar_1$ is substituted or unsubstituted and is selected from the group consisting of phenyl, 2-pyridyl, 3-pyridyl, 4-pyridyl, 3,5-pyrimidinyl, and 2,4-pyrimidinyl, wherein substitutions are selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof; and R is one, two or three substitutions at any position on the quinoline ring, wherein the substitutions are independently selected from the group consisting of H, F, Cl, OH, alkyl, O-alkyl, amino, alkylamino, carboxyl, aminocarbonyl, alkylaminocarbonyl, alkylsulphonylamino, morpholinoethoxy, piperidinoethoxy, pyrrolidinoethoxy, and combinations thereof.

In some embodiments, the compound of Formula (I), (II), (III), (IIIa), (IIIb), (IIIc), (IIId), (IV), (V), (VI), or (VII) can be used to inhibit PFKFB3 or otherwise interfere or interact with PFKFB3 in vitro. In some embodiments, the compound is a competitive inhibitor of PFKFB3. In some embodiments, the compound can be used to contact a cell or cell extract comprising PFKFB3. In some embodiments, the compound can be used to contact a tissue, tissue extract, or other biologically derived sample, such as a blood sample. In some embodiments, the compound of Formula (I), (II), (III), (IIIa), (IIIb), (IIIc), (IIId), (IV), (V), (VI), or (VII) can be used to contact PFKFB3 in vivo, wherein the PFKFB3 is present in a living subject, such as a mammal or bird. In some embodiments, the mammal is a human. By interfering with PFKFB3 activity, the compound of Formula (I), (II), (III), (IIIa), (IIIb), (IIIc), (IIId), (IV), (V), (VI), or (VII) or a pharmaceutical formulation thereof can be used to decrease glycolytic flux in a cell, in some cases specifically in tumor cells, thereby decreasing intracellular lactate and fructose-2,6-bisphosphate levels.

IV. PHARMACEUTICAL FORMULATIONS

The compounds of Formulas (I), (II), (III), (IIIa), (IIIb), (IIIc), (IIId), (IV), (V), (VI), and (VII), the pharmaceutically acceptable salts thereof, the prodrugs corresponding to compounds of Formulas (I), (II), (III), (IIIa), (IIIb), (IIIc), (IIId), (IV), (V), (VI), and (VII), and the pharmaceutically acceptable salts thereof, are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral, intravenous, or aerosol administration as discussed in greater detail below. Also, the presently disclosed subject matter provides such active compounds that have been lyophilized and that can be reconstituted to form pharmaceutically acceptable formulations (including formulations pharmaceutically acceptable in humans) for administration.

The therapeutically effective dosage of any specific active compound, the use of which is within the scope of embodiments described herein, will vary somewhat from compound to compound, and subject to subject, and will depend upon the condition of the subject and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

In accordance with the presently disclosed methods, pharmaceutically active compounds as described herein can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations comprise a compound of Formula (I), (II), (III), (IIIa), (IIIb), (IIIc), (IIId), (IV), (V), (VI), or (VII) described herein, a prodrug as described herein, or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to compounds of Formulas (I), (II), (III), (IIIa), (IIIb), (IIIc), (IIId), (IV), (V), (VI), and (VII) or their salts or prodrugs, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising a compound of Formula (I), (II), (III), (IIIa), (IIIb), (IIIc), (IIId), (IV), (V), (VI), or (VII), or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. The unit dosage form typically comprises from about 10 mg to about 10 grams of the compound salt. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Other pharmaceutical formulations can be prepared from the water-insoluble compounds disclosed herein, or salts thereof, such as aqueous base emulsions. In such an instance, the formulation will contain a sufficient amount of pharmaceutically acceptable emulsifying agent to emulsify the desired amount of the compound or salt thereof. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound will be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques.

The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, more preferably from about 0.5 to about 5 microns. The solid particles can be obtained by processing the solid compound or a salt thereof, in any appropriate manner known in the art, such as by micronization. Most preferably, the size of the solid particles or droplets will be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation will comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

V. METHODS OF INHIBITING CELL PROLIFERATION AND TREATING CANCER WITH PFKFB3 INHIBITORS

The presently disclosed subject matter provides methods and compositions for inhibiting cell proliferation. In particular, the presently disclosed subject matter provides methods of interfering PFKFB3 activity and disrupting glycolytic flux. By disrupting glycolytic activity, proliferation of the cell ceases and, in some cases, apoptosis is triggered. Thus, the presently disclosed subject matter provides a method of treating diseases, including cancer, involving undesirable glycolytic activity, and/or undesirable cell proliferation.

In some embodiments, the methods for inhibiting cell proliferation or treating a cancer comprise administering to a subject in need thereof an active compound as described herein. These active compounds, as set forth above, include the compounds of Formulas (I), (II), (III), (IIIa), (IIIb), (IIIc), (IIId), (IV), (V), (VI), and (VII), their corresponding prodrugs, and pharmaceutically acceptable salts of the compounds and prodrugs. In some embodiments, the active compound is present in a pharmaceutical formulation as described hereinabove.

The presently disclosed compounds can provide therapy for a wide variety of tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, and lymphoid cancers.

An "effective amount" is defined herein in relation to the treatment of cancers is an amount that will decrease, reduce, inhibit, or otherwise abrogate the growth of a cancer cell or tumor. In some embodiments, the compound of Formula (I), (II), (III), (IIIa), (IIIb), (IIIc), (IIId), (IV), (V), (VI), or (VII) can be delivered regionally to a particular affected region or regions of the subject's body. In some embodiments, wherein such treatment is considered more suitable, the compound of Formula (I), (II), (III), (IIIa), (IIIb), (IIIc), (IIId), (IV), (V), (VI), or (VII) can be administered systemically. For example, the compound can be administered orally or intravenously.

In addition, it will be appreciated that therapeutic benefits for the treatment of cancer can be realized by combining treatment with a PFKFB3 inhibitor compound or other compound of the presently disclosed subject matter with one or more additional anti-cancer agents or treatments. The choice of such combinations will depend on various factors including, but not limited to, the type of disease, the age and general health of the subject, the aggressiveness of disease progression, and the ability of the subject to tolerate the agents that comprise the combination. For example, the PFKFB3 inhibitor compound can be combined with other agents and therapeutic regimens that are effective at reducing tumor size (e.g., radiation, surgery, chemotherapy, hormonal treatments, and or gene therapy). Further, in some embodiments, it can be desirable to combine the PFKFB3 inhibitor compound with one or more agents that treat the side effects of a disease or the side effects of one of the therapeutic agents, e.g., providing the subject with an analgesic, or agents effective to stimulate the subject's own immune response (e.g., colony stimulating factor).

In some embodiments, the presently disclosed methods and compounds can be used in conjunction with chemotherapy and/or radiation focused on aerobic, fast-growing cells, which we will here refer to collectively and individually as "aerobic treatment." In some embodiments, the use of the presently disclosed PFKFB3 inhibitors will add to the efficacy of cancer treatment by selectively killing the anaerobically slow-growing tumor cells found at the inner core of solid tumors, which are usually the most resistant and consequently the most difficult to eradicate using aerobic treatments.

Thus, a variety of chemical compounds, also described as "anti-neoplastic" agents or "chemotherapeutic agents" can be used in combination with one or more of the PFKFB3 inhibitor compounds of the presently described subject matter. Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, also can be combined with compounds of the presently disclosed subject matter in pharmaceutical compositions. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the PFKFB3 inhibitor compounds of the presently disclosed subject matter to provide a suitable cancer treatment.

Thus, current chemotherapeutic agents that can be used in a combination treatment with a PFKFB3 inhibitor of the presently disclosed subject matter include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chjlorambucil, bisulfan, nitrosurea, dactinomycin, duanorubicin, doxorubicin, bleomycin, plicomycin, tamoxifen, taxol, transplatimun, vinblastin, and methotrexate, and the like.

Combination treatments involving a PFKFB3 inhibitor compound and another therapeutic agent, such as another chemotherapeutic agent can be achieved by contacting cells with the PFKFB3 inhibitor and the other agent at the same time. Such combination treatments can be achieved by contacting the cell with a single composition or pharmacological formulation that includes both agents, or by contacting the cell with two distinct compositions or formulations, at the same time, wherein one composition includes the PFKFB3 inhibitor and the other includes the other agent.

Alternatively, treatment with the PFKFB3 inhibitor compound can precede or follow treatment with the other agent by intervals ranging from minutes to weeks. In embodiments where the other agent and the PFKFB3 inhibitor therapy are applied separately to the cell, one would generally ensure that a significant period of time did not expire between the time of each delivery, such that the agent and the PFKFB3 inhibitor treatment would still be able to exert an advantageously combined effect on the cell. In such instances, it is provided that one would contact the cell with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the PFKFB3 inhibitor or of the other agent will be desired.

In another embodiment, a PFKFB3 inhibitor compound of the presently disclosed subject matter or another anti-cancer compound being used in combination with the PFKFB3 inhibitor is either combined with or covalently bound to a cytotoxic agent bound to a targeting agent, such as a monoclonal antibody (e.g., a murine or humanized monoclonal antibody). It will be appreciated that the latter combination can allow the introduction of cytotoxic agents into cancer cells with greater specificity. Thus, the active form of the cytotoxic agent (i.e., the free form) will be present only in cells targeted by the antibody.

Additional cancer treatments also can be used in combination with administration of a PFKFB3 inhibitor compound. For example, a PFKFB3 inhibitor compound of the presently disclosed subject matter can be used as part of a treatment course further involving attempts to surgically remove part or all of a cancerous growth. For instance, a PFKFB3 inhibitor of the presently disclosed subject matter can be administered after surgical treatment of a subject to treat any remaining neoplastic or metastasized cells. Treatment with a PFKFB3 inhibitory agent of the presently disclosed subject matter also can precede surgery, in an effort to shrink the size of a tumor to reduce the amount of tissue to be excised, thereby making the surgery less invasive and traumatic.

Treating cancer with a PFKFB3 inhibitor agent of the presently disclosed subject matter can further include one or more treatment courses with a radiotherapeutic agent to induce DNA damage. Radiotherapeutic agents, include, for example, gamma irradiation, X-rays, UV-irradiation, microwaves, electronic emissions, radioisotopes, and the like. Therapy can be achieved by irradiating the localized tumor site with the above-described forms of radiation.

A combination therapy also can involve immunotherapy directed at tumor antigen markers that are found on the surface of tumor cells. Treatment of a cancer with a PFKFB3 inhibitor of the presently disclosed subject matter can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN-II, BRCA1, VHL, FCC, MCC, ras, myc, neu, raf, erb, src, fms, jun, trk, ret, gsp, hst, bcl, and abl, which are often mutated versions of their normal cellular couterparts in cancerous tissues.

The PFKFB3 inhibitor compounds of the presently disclosed subject matter can be tested to measure their ability to inhibit growth of cancer cells, to induce apoptosis of the cancer cells, to reduce tumor burden, and to inhibit metastases. For example, one can measure cell growth according to the MTT assay. Growth assays as measured by the MTT assay are well known in the art. In the MTT assay, cancer cells are incubated with various concentrations of anti-cancer compound, and cell viability is determined by monitoring the formation of a colored formazan salt of the tetrazolium salt, 3-(4,5-dimethylthiazol-2-yl)-2,5-diphenyltetrazolium bromide (MTT). Other known assays for measuring cell death and or cell proliferation can also be employed.

In vivo testing can be performed using a mouse xenograft model, for example, in which OVCAR-5 tumor cells are grafted onto nude mice, in which mice treated with a compound of Formula (I), (II), (III), (IIIa), (IIIb), (IIIc), (IIId), (IV), (V), (VI), or (VII) are expected to have tumor masses that, on average, increase for a period following initial dosing, but will shrink in mass with continuing treatment. In contrast, mice treated with a control (e.g., DMSO) are expected to have tumor masses that continue to increase. Additional methods of measuring the anti-neoplastic effects of the presently disclosed compounds are described further, hereinbelow, in the Examples.

VI. SCREENING METHODS

The presently disclosed subject matter provides a method of screening compounds for their ability to interfere with (e.g., inhibit or competitively inhibit) PFKFB3. In particular, the method comprises providing a three-dimensional model of PFKFB3, including the F6P binding pocket of PFKFB3; providing a three-dimensional model of a compound (e.g., a small molecule); and screening the compound for its ability to interact with one or more solvent accessible sites in the F6P binding pocket of the PFKFB3 model. In some embodiments, the method can be performed using a computer (i.e., in silico). In some embodiments, the method can include providing the three-dimensional models of a plurality of compounds (i.e., a library or database of compounds) and screening each compound individually and then comparing the ability of an individual compound to interact with the F6P binding pocket with the abilities of the other compounds in the plurality of compounds.

Thus, in one aspect, the method of screening compounds generally includes computationally evaluating the potential of a selected chemical entity or entities to associate with the computational model of the F6P binding pocket of PFKFB3. For example, this method can include the steps of (a) employing a computational approach to perform a fitting operation between the selected chemical entity or entities and the F6P binding pocket of PFKFB3; and (b) analyzing the results of the fitting operation to quantify the association between the chemical entity or entities and the binding pocket. In some embodiments, a molecule or library of molecules can be tested for binding affinity with the F6P binding pocket of PFKFB3 using visual inspection or using computer-aided docking experiments.

In some embodiments, the computational model of PFKFB3 can be derived from known X-ray structures of PFKFB3 isozymes. For example, a model of PFKFB3 can be derived by aligning the residue sequence of PFKFB3 with homologous sequences of the human liver PFKFB1 and rat testes PFKFB4 isozymes. The crystal structure of PFKFB3 itself has also been described. See Kim et al., *J. Biol. Chem.*, 281 (5) 2939-2944 (2006).

The term "binding pocket" refers to a region of a molecule or molecular complex, that as a result of its shape, favorably associates with another chemical entity (e.g., F6P or an inhibitor). The term "pocket" includes, but is not limited to, a cleft, channel or site. The shape of a binding pocket may be largely pre-formed before binding of a chemical entity, may be formed simultaneously with binding of a chemical entity, or may be formed by the binding of another chemical entity to a different binding pocket of the molecule, which in turn induces a change in shape of the binding pocket.

The term "docking" refers to orienting, rotating, translating a chemical entity in the binding pocket, domain, molecule or molecular complex or portion thereof based on distance geometry or energy. Docking can be performed by distance geometry methods that find sets of atoms of a chemical entity that match sets of sphere centers of the binding pocket, domain, molecule or molecular complex or portion thereof. See Meng et al., *J. Comp. Chem.*, 4, 505-524 (1992). Sphere centers are generated by providing an extra radius of a given length from the atoms (excluding hydrogen atoms) in the binding pocket, domain, molecule or molecular complex or portion thereof. Real-time interaction energy calculations, energy minimizations or rigid-body minimizations (see Gschwend et al., *J. Mol. Recognition*, 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen, et al., *J. Med.*

Chem., 33, 889-894 (1990)). Docking can also be performed by combining a Monte Carlo search technique with rapid energy evaluation using molecular affinity potentials. See Goodsell and Olson, *Proteins: Structure, Function and Genetics* 8, 195-202 (1990). Software programs that carry out docking functions include, but are not limited to, MATCH-MOL (see Cory, et al., *J. Mol. Graphics*, 2, 39 (1984)); MOLFIT (see Redington, *Comput. Chem.* 16, 217 (1992)) and DOCK (see Meng et al., supra).

The term "generating a three-dimensional structure" or "generating a three-dimensional representation" refers to converting the lists of structure coordinates into structural models or graphical representation in three-dimensional space. This can be achieved through commercially or publicly available software. A model of a three-dimensional structure of a molecule or molecular complex can thus be constructed on a computer screen by a computer that is given the structure coordinates and that comprises the correct software. The three-dimensional structure can be displayed or used to perform computer modeling or fitting operations. In addition, the structure coordinates themselves, without the displayed model, may be used to perform computer-based modeling and fitting operations.

In some embodiments, the ability of a compound to interact with a binding pocket or solvent accessible surface can be quantified. The term "contact score" refers to a measure of shape complementarity between the chemical entity and binding pocket, which is correlated with an RMSD value obtained from a least square superimposition between all or part of the atoms of the chemical entity and all or part of the atoms of the ligand bound in the binding pocket. The docking process can be facilitated by the contact score or RMSD values. For example, if the chemical entity moves to an orientation with high RMSD, the system will resist the motion. A set of orientations of a chemical entity can be ranked by contact score. A lower RMSD value will give a higher contact score. See Meng et al. *J. Comp. Chem.*, 4, 505-524 (1992).

The term "root mean square deviation" or "RMSD" means the square root of the arithmetic mean of the squares of the deviations from the mean. It is a way to express the deviation or variation from a trend or object.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

As will be understood by one of skill in the art in view of the presently disclosed subject matter, a variety of small molecule (i.e., compounds having a molecular weight of 1000 atomic mass units (amu) or less, 750 amu or less or of 500 amu or less) libraries are available for computational screening methods. Chemical structure databases which may be used include, but are not limited to, ACD (Molecular Designs Ltd, now Elsevier MDL, San Ramon, Calif., United States of America), NCI (National Cancer Institute, Fredrick, Md., United States of America), CCDC (Cambridge Crystallographic Data Center, Cambridge, United Kingdom), CAST (Chemical Abstract Service, Columbus, Ohio, United States of America), Maybridge (Maybridge Chemical Company Ltd, Tintagel, United Kingdom), Aldrich (Aldrich Chemical Company, Milwaukee, Wis.), and the Directory of Natural Products (Chapman & Hall, London, United Kingdom).

Computer programs such as CONCORD (Tripos Associates, St. Louis, Mo., United States of America) or DB-Converter (Molecular Simulations Ltd., San Leandro, Calif., United States of America) can be used to convert a data set represented in two dimensions to one represented in three dimensions. Programs suitable for searching three-dimensional databases to identify molecules bearing a desired pharmacophore include: MACCS-3D and ISIS/3D (Molecular Design Ltd., now Elsevier MDL, San Ramon, Calif., United States of America), ChemDBS-3D (Chemical Design Ltd., Oxford, United Kingdom), and Sybyl/3 DB Unity (Tripos Associates, St. Louis, Mo., United States of America). As used herein, a "pharmacophore" or a "pharmacophoric pattern" is a geometric arrangement of features of a chemical entity that are believed to be important for binding.

Compounds can also be screened for their ability to inhibit PFKFB3 using cell-based screening methods. Thus, in some embodiments, compounds can be screened for their ability to arrest cell proliferation and/or lactate production in cells expressing PFKFB3. In some embodiments, compounds can be screened using a cell-based screening method to further verify the PFKFB3 inhibitory ability of a compound previously identified via an in silico screening method.

EXAMPLES

General Methods

Statistical significance for the growth inhibition, lactate production, and in vivo studies between control and 3PO treatment was determined by a two-sample t-test using Graph Pad Prism Version 3.0 (Graph Pad Software, San Diego, Calif., United States of America). A p-value<0.01 was considered to be statistically significant.

Example 1

PFKFB3 Molecular Modeling and Compound Screening

Figure 2A:
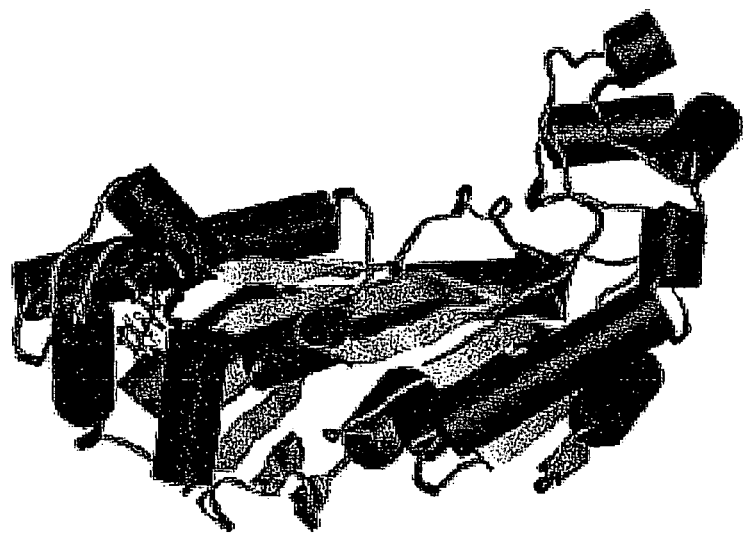
FIG. 2A is an schematic drawing of the homology model of 6-phosphofructo-2-kinase/fructose-2,6-bisphosphatase 3 (PFKFB3) illustrated in secondary structure. The drawing also shows 3-(3-pyridinyl)-1-(4-pyridinyl)-2-propen-1-one (3PO) in its binding site.
Figure 2B:
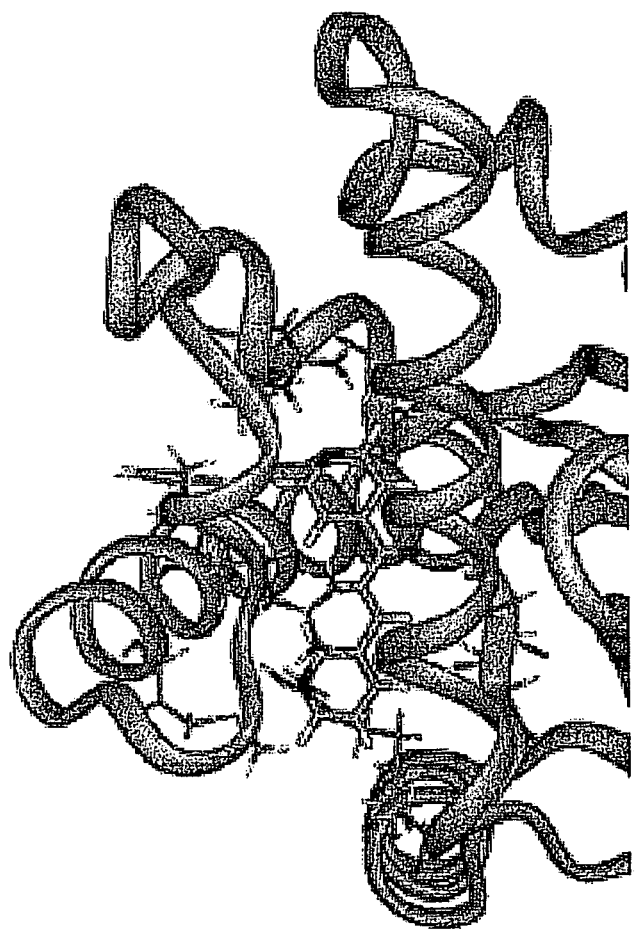
FIG. 2B is an illustration of the side view of the PFKFB3 binding pocket showing residues that are within 2.5 angstroms.
Figure 2C:
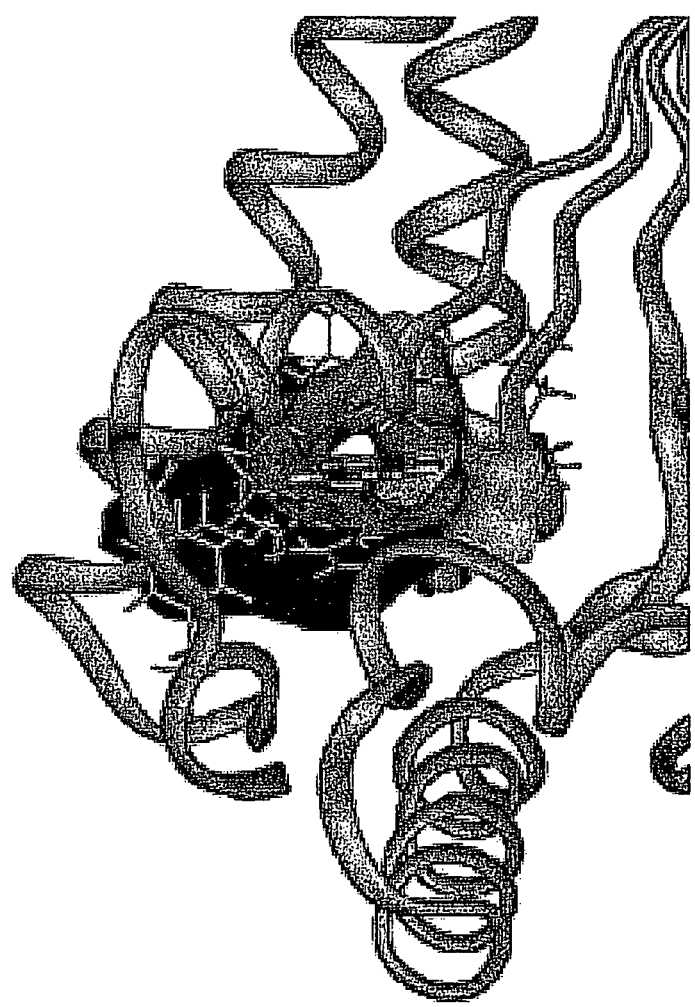
FIG. 2C is an illustration of the end view of the PFKFB3 binding pocket showing the Connelly surface of the binding pocket residues with the front residues shown in stick representation.

Computational modeling was carried out using a Silicon Graphics Array (71×R12000 and R14000 processors with over 1 TB storage), a 32P R14000 500 MHz Origin 2000 server and a 2P R12000 300 MHz OCTANE graphics workstation (SGI, Sunnyvale, Calif., United States of America). The PFKFB3 homology model used the X-ray structures of the rat testes PFKFB4 (PDB code 1BIF) isozyme as a structural template. An alignment was generated using ClustalW. See Chenna et al., *Nucleic Acids Res.*, 31, 3497-3500 (2003). Four homology models were generated using Modeller (see Sali and Blundell, *J. Mol. Biol.*, 234, 779-815 (1993)) and the structure that best reproduced the PFKFB3 binding site (see Chesney et al., *Proc. Natl. Acad. Sci*, 96, 3047-3052 (1999) and Bertrand et al., *Eur. J. Biochem.*, 254, 490-496 (1998)) was selected for further use. The residues essential to ligand binding and protein activity for PFKFB3 (see Chesney et al., *Proc. Natl. Acad. Sci*, 96, 3047-3052 (1999) and Bertrand et al., *Eur. J. Biochem.*, 254, 490-496 (1998)) were correlated to equivalent residue numbers in the consensus structure. The model was read into InsightII (Accelrys, San Diego, Calif., United States of America) and three of the essential residues, Arg 66, Tyr 161, and Thr 94, were selected as the centroid target for the virtual screening runs. Illustrations of the PFKFB3 homology model are shown in FIGS. 2A, 2B, and 2C.

The amino acid sequence for the homology model (SEQ ID NO: 1) corresponds to amino acids 34-466 of the amino acid sequence for 6-phosphofructo-2-kinase/fructose-2,6-biphosphatase 3 from *Homo sapiens* (GENBANK® Accession No. NP_004557). SEQ ID NO: 1 is encoded by nucleotides 429-1727 of GENBANK® Accession No. NM_004566 (SEQ ID NO: 2).

SEQ ID NO: 1 is:

```
SPTVIVMVGLPARGKTYISKKLTRYLNWIGVPTKVFNVGEYRREAVKQ
YSSYNFFRPDNEEAMKVRKQCALAALRDVKSYLAKEGGQIAVFDATNT
TRERRHMILHFAKENDFKAFFIESVCDDPTVVASNIMEVKISSPDYKD
CNSAEAMDDFMKRISCYEASYQPLDPDKCDRDLSLIKVIDVGRRFLVN
RVQDHIQSRIVYYLMNIHVQPRTIYLCRHGENEHNLQGRIGGDSGLSS
RGKKFASALSKFVEEQNLKDLRVWTSQLKSTIQTAEALRLPYEQWKAL
NEIDAGVCEELTYEEIRDTYPEEYALREQDKYYYRYPTGESYQDLVQR
LEPVIMELERQENVLVICHQAVLRCLLAYFLDKSAEEMPYLKCPLHTV
LKLTPVAYGCRVESIYLNVESVCTHRERSEDAKKGPNPLMRRNSVTPL
A.
```

The Ludi (Accelrys, San Diego, Calif., United States of America) virtual screening program was used to process the ChemNavigator iResearch library (ChemNavigator, San Diego, Calif., United States of America). After these screening runs were completed, molecules scoring above 500 using Ludi's scoring system were analyzed by visual inspection in the active site of the protein. Ligands that were docked correctly in the active pocket were catalogued according to the target and library used for screening. The 200 highest scoring molecules were identified using Scifinder Scholar and the top 45 were selected for potential experimental assays.

Structures of some of the compounds determined to have binding potential in the PFKFB3 F6P binding pocket are shown below in Table 1. The compounds of the presently disclosed subject matter can be obtained from suitable commercial sources, including, but not limited to, Sigma-Aldrich (St. Louis, Mo., United States of America) and Chembridge Corporation (San Diego, Calif., United States of America).

Alternatively, chalcones, aza-chalcones and analogues thereof can also be synthesized by methods known in the art. For example, the chalcones and aza-chalcones can be prepared by condensing the appropriate aryl aldehyde and aryl ketone followed by dehydration (i.e., loss of $H_2O$) to form an enone. The condensation can be catalyzed by either acid or base. In some embodiments, a benzaldehyde, substituted benzaldehyde or aza-analogue thereof can be mixed with an acetophenone, a substituted acetophenone, or an aza analogue thereof in the presence of a base (e.g., an aqueous solution of NaOH) at a suitable temperature for a period of time (e.g., minutes, one to several hours, one or more days). The solution can then be extracted with a hydrophobic solvent and the extract concentrated to provide the chalcone or aza-chalcone. In some embodiments, the extract can be purified further via any suitable means, such as chromatography or recrystallization.

TABLE 1

PFKFB3 Inhibitors

Ar—C(O)—CH=CH—Ar'

| Compound Number | Ar | Ar' | Structure |
|---|---|---|---|
| 1 (3PO) | 4-pyridyl | 3-pyridyl | 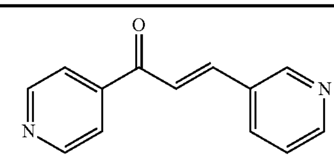 |
| 2 | 3-pyridyl | 4-chlorophenyl | 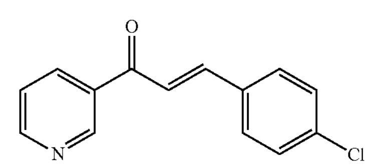 [SMILES: O=C(/C=C/c1ccc(Cl)cc1)c1cccnc1] |
| 3 | 4-pyridyl | 1-napthyl | 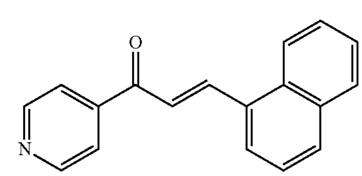 [SMILES: O=C(/C=C/c1cccc2ccccc12)c1ccncc1] |
| 4 | 3-pyridyl | 2-quinolynyl | 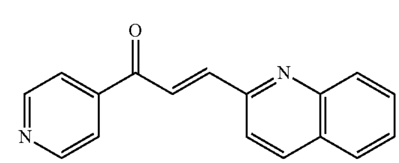 [SMILES: O=C(/C=C/c1ccc2ccccc2n1)c1ccncc1] |

TABLE 1-continued

PFKFB3 Inhibitors

Ar—C(=O)—CH=CH—Ar'

| Compound Number | Ar | Ar' | Structure |
|---|---|---|---|
| 5 | 4-pyridyl | 4-acetamidophenyl | 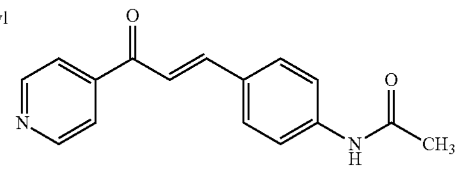 |
| 6 | 2-pyridyl | 2-chlorophenyl | 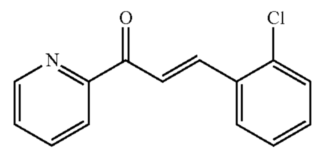 [SMILES: O=C(/C=C/c1ccccc1Cl)c1ccccn1] |
| 7 | 3-pyridyl | 2-chlorophenyl | 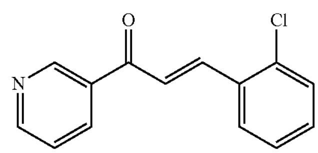 [SMILES: O=C(/C=C/c1ccccc1Cl)c1cccnc1] |

Example 2

In Vitro Recombinant Enzyme Assays

PKFKB3 Cloning, Expression and Purification:

Human PFKFB3 cDNA was amplified from a pre-existing mammalian expression plasmid using the following primers:

```
PFKFB3F:    5'-CTTCATATGCCGTTGGAACTGACGCA-3'
                                    (SEQ ID NO: 3)

PFKFB3R:    5'-CTTCTCGAGGTGTTTCCTGGAGGAGTCAGC-3'
                                    (SEQ ID NO: 4)
```

The PCR product was digested with XhoI and NdeI restriction enzymes (Promega, Madison, Wis., United States of America) and cloned into the corresponding sites in the pET-30b(+) vector (Novagen, San Diego, Calif., United States of America). The pET-30b(+)-PFKFB3C-termHis plasmid was subsequently transformed into BL21(DE3) *E. coli* competent cells (Novagen, San Diego, Calif., United States of America).

For expression and purification of PFKFB3, a one liter culture of BL21-PFKFB3 transformed cells was shaken for 16 hours at 37° C. After 16 hours, an additional liter of LB media containing 2 mM isopropyl β-D-1-thiogalactopyranoside (IPTG; final concentration=1 mM) was added to the cultures and shaken for 4 hours at 30° C. Bacteria were collected by centrifugation, and protein purification was performed as described in the Qiagen (Venlo, The Netherlands) protocol under native conditions. Briefly, bacterial pellets were washed once in Dulbecco's phosphate buffered saline (PBS; Invitrogen, Carlsbad, Calif., United States of America) and resuspended in 2 mL per pellet gram weight of lysis buffer with the addition of 5 mM β-mercaptoethanol, 1 mg/mL lysozyme, 1 mM phenylmethylsulphonyl fluoride (PMSF), and 1:100 dilution of protease inhibitor cocktail (Sigma-Aldrich, St. Louis, Mo., United States of America). The bacterial mixture was then sonicated 8 times for 10 seconds, and supernatant was obtained through centrifugation. Lysate was incubated for 1 hour with 3 mL of 50% Ni-NTA and the mixture was loaded onto a Poly-Prep chromatography column (BioRad, Hercules, Calif., United States of America). Beads were washed with 15 mL of 6× His wash buffer containing 1 mM PMSF and 1:100 dilution of protease inhibitor cocktail, and PFKFB3 was eluted with 1.5 mL of elution buffer containing 200 mM imidazole. For further purification, elution fractions were dialyzed for 16 hours against a 20 mM Tris-HCl, 200 mM NaCl (pH 7.4) buffer, and subjected to gel filtration via Sephadex S200 columns (Amersham, Piscataway, N.J., United States of America).

PFKFB3 Enzymatic Assays:

PFKFB3 activity was measured by an enzyme-coupled kinetics assay incorporating pyruvate kinase and lactate dehydrogenase as previously described. See Bucher and Pfleiderer, *Methods in Enzymology*, 1, 435-440 (1955). The assay measures NADH consumption spectrophotometrically as a loss of absorption at 340 nm with stoichiometry of 1 mol ATP: 1 mol NADH consumed. Assays were carried out in 96 well plates at 37° in 200 μL final volume containing 1XPFKFB3 reaction buffer (100 mM Tris-HCl, 100 μM EDTA, 5 mM $KH_2PO_4$; pH=7.4), 420 μM phophoenolpyruvate (PEP), 5 mM ATP, 400 μM NADH, 613 units of pyruvate kinase (PK), 1092 units of lactate dehydrogenase (LDH), increasing concentrations of fructose-6-phosphate (40-400 μM), and 15 μg of purified PFKFB3. Control reactions for the enzyme assays received active PFKFB3 without F6P. For compound 1 inhibition, reactions were incubated in the presence of either 60 μM, 100 μM, or 150 μM of the inhibitor. Control reactions for compound 1 inhibition contained increasing amounts of 1 without addition of PFKFB3. Assays were measured using a BioTek POWERWAVE™ plate reader (BioTek Instruments, Inc., Winooski, Vt., United States of America) in kinetics mode over 15 minute periods to determine kinetic rate of PFKFB3. The enzyme kinetics module for SigmaPlot® 9.0 (SYSTAT Software, Inc., San Jose, Calif., United States of America) was used to calculate the kinetic parameters for PFKFB3 and 1 inhibition ($V_{max}$, $K_m$, and $K_i$). The $V_{max}$ is expressed in specific activity of PFKFB3 as nmol F6P×min$^{-1}$×mg$^{-1}$. $K_m$ and $K_i$ values are expressed in µM for F6P or 1, respectively. The data represented are the mean±STD from triplicate measurements from two independent experiments.

Figure 3:
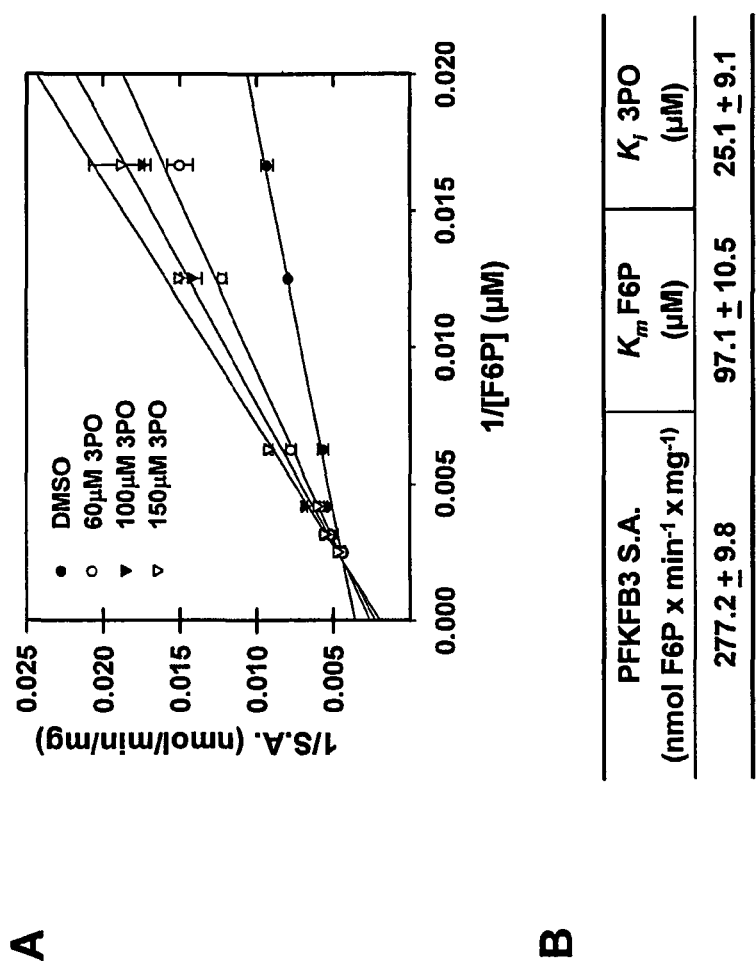
FIG. 3A is a graph showing the Lineweaver-Burke double reciprocal plots of PFKFB3 enzyme activity as a function of fructose-6-phosphate concentration (60, 80, 160, 240, 320, or 400 μM). Kinase assays were performed in the presence of DMSO (●), 60 μM 3PO (○), 100 μM 3PO (▼) and 150 μM 3PO (∇). 3PO refers to compound 1, 3-(3-pyridinyl)-1-(4-pyridinyl)-2-propen-1-one.
FIG. 3B is a table of enzyme kinetic parameters including the specific activity (S.A.) of PFKFB3, $K_m$ of fructose-6-phsophate, and $K_i$ of 3PO.

As shown in FIG. 3A, the Lineweaver-Burke double reciprocal plot reveals that 1 inhibits PFKFB3 activity through a mixed inhibition mechanism, both competitively and non-competitively. Incubation with 1 results in a significant dose-dependent decrease in PFKFB3 enzyme activity at lower concentrations of F6P. However, this inhibition is overcome by increasing amounts of F6P, suggesting that there is competition between 1 and F6P for the PFKFB3 binding site. From these studies, enzyme kinetics parameters were calculated for PFKFB3 activity and compound 1 inhibition. The specific activity of recombinant PFKFB3 was found to be 277±9 nmol F6P×min$^{-1}$×mg$^{-1}$, and the $K_m$ for F6P was determined to be 97 µM. See FIG. 3B. The $K_i$ for 1 was measured to be 25±9 µM, which is an approximately four-fold decrease compared to the $K_m$ for F6P. These studies confirm that 1 is in fact an inhibitor of PFKFB3 activity primarily through competition with F6P, and that molecular targeting of enzyme substrate binding sites for competitive inhibitors is a sound method for identifying anti-neoplastic therapies.

Example 3

Toxicity of Compound 1 in Transformed Tumor Cells

Generation of FLAG-PFKFB3 Construct for Mammalian Expression:

FLAG-PFKFB3 containing the complete PFKFB3 coding sequence and FLAG-epitope at its N-terminus was subcloned into the BamHI/HindIII restriction sites within the retroviral Tet response vector pRevTRE (Clontech, Mountain View, Calif., United States of America). Recombinant retrovirus was produced by Lipofectamine-mediated (Invitrogen, Carlsbad, Calif., United States of America) transfection of the pRevTRE-FLAG-PFKFB3 construct into PT67 packaging cell lines. To create Jurkat cell lines that have stably integrated and express inducible FLAG-PFKFB3, the cells were infected with recombinant retrovirus containing FLAG-PFKFB3, and stable clones were selected in the presence of 400 µg/mL hygromycin (Clontech, Mountain View, Calif., United States of America).

Cell Culture:

The K562, HL-60, MDA-MB231, and melanoma (CRL-11174) human cancer cell lines were purchased from ATCC (American Tissue Type Culture Collection, Manassas, Va., United States of America). HeLa, A549, Lewis Lung Carcinoma, MDA-MB231, and melanoma cells were grown in Dulbecco's Modified Eagle Medium (DMEM) (Hyclone, Logan, Utah, United States of America) supplemented with 10% fetal bovine serum (Hyclone, Logan, Utah, United States of America) and 50 µg/mL gentamicin sulfate (Invitrogen, Carlsbad, Calif., United States of America). The HL-60, K562, and Jurkat cell lines were grown in RPMI-1640 medium (Hyclone, Logan, Utah, United States of America) supplemented with 10% fetal bovine serum and 50 µg/mL gentamicin sulfate. The primary Normal Human Bronchial Epithelial (NHBE) cells and cells that were immortalized with human telomerase (ht) and large T antigen (LT) and transformed with mutated ras (ht/LT/ras cells) were cultured in Bronchial Epithelial Cell Basal Growth Medium (Cambrex, Walkersville, Md., United States of America) supplemented with 52 µg/mL bovine pituitary extract, 0.5 µg/mL hydrocortisone, 0.5 µg/mL human epidermal growth factor, 0.5 µg/mL epinephrine, 10 µg/mL transferrin, 5 µg/mL insulin, 0.1 ng/mL retinoic acid, 6.5 ng/mL triiodothyronine, 50 µg/mL gentamycin, and 50 ng/mL amphotericin-B (SingleQuots, Cambrex, Walkersville, Md., United States of America). All cell lines were maintained under 5% $CO_2$ at 37° C.

Cell Cycle Analysis and Flow Cytometry:

Jurkat cells were plated at 1×105 cells/mL in RPMI medium supplemented with 10% FBS and 50 µg/mL gentamicin sulfate. Cell cycle analysis was performed using Vybrant DyeCycle Orange stain (Molecular Probes-Invitrogen, Eugene, Oreg., United States of America) according to the manufacturer's protocol.

In Vitro Growth Inhibition:

All cell lines were plated at $1 \times 10^5$ cells/well in the appropriate medium. For suspension cells, increasing concentrations of 1 were added immediately to the medium, whereas, compound 1 treatment was initiated the following day for adherent cell lines. For dose-dependent studies, compound 1 was added in increasing concentrations for 36 hours. For time-dependent studies, 10 µM of compound 1 was added at time 0, 4, 8, 16, 24, or 36 hours. For PFKFB3 overexpression studies, Jurkat cells containing the FLAG-PFKFB3 expression vector or a control plasmid were induced by addition of doxycycline (1 µg/mL; Clontech, Mountain View, Calif., United States of America) 24 hours prior to incubation with compound 1.

Cells were collected 48 hours post-treatment, and cell number and viability were determined by trypan blue exclusion. $IC_{50}$ values were calculated as the compound 1 concentration needed for 50% of vehicle treated cell growth. The data represented are the mean±STD from triplicate measurements from three independent experiments.

Lactate Measurements:

$1 \times 10^5$ Jurkat cells were incubated with increasing concentrations of 1. At desired time points, media samples were collected and lactate levels were measured using a lactate oxidase based colorimetric assay read at 540 nm according to the manufacturer's instructions (Trinity, St. Louis, Mo., United States of America) and normalized to protein concentration.

Fructose-2,6-bisphosphate Assay:

Jurkat cells were plated at $1 \times 10^5$ cells/mL and immediately incubated with 10 µM compound 1 for 0, 4, 8, 16, 24, or 36 hours. F2,6BP assays were performed as previously described. See Van Shaftingen et al., *Eur. J. Biochem*, 129, 191-195 (1982).

2-Deoxy-glucose Uptake:

Jurkat cells were plated at $1 \times 10^5$ cells/mL in RPMI medium supplemented with 10% FBS and 50 µg/mL gentamicin sulfate. Cells were immediately treated with vehicle (DMSO) or 10 µM compound 1 for up to 36 hours, then placed in glucose free RPMI medium for 30 minutes. $^{14}$C-2-DG (0.25 µCi/mL; Perkin Elmer, Waltham, Mass., United States of America) was added for 60 more minutes. The cells were then washed three times with ice-cold, glucose-free RPMI. Cell lysates were collected in 500 µL of 0.1% SDS, and scintillation counts (cpm) were measured on 400 µL of lysate. Counts were normalized to protein concentration. Data represent mean±STD from duplicate measurements from two independent experiments.

Whole Cell ATP:

Jurkat cells were plated at $1\times10^5$ cells/mL and incubated with 10 µM compound 1 for various time points. ATP levels were determined using an ATP determination kit from Molecular Probes-Invitrogen (Eugene, Oreg., United States of America) according to the manufacturer's protocol.

NAD+ and NADH Levels:

Jurkat cells were plated at $1\times10^5$ cells/mL and immediately incubated with 10 µM compound 1 for 0, 4, 8, 16, 24, or 36 hours. NAD+ and NADH levels were measured using the EnzyChrom NAD+/NADH assay kit from BioAssay Systems (Hayward, Calif., United States of America) according to the maufacturer's protocol.

NMR:

Jurkat cells were treated with vehicle (DMSO) or 10 µM compound 1 in the presence of $^{13}$C-glucose for 36 hours. Equal numbers of cells were pelleted, washed twice with cold PBS to remove remaining medium, pelleted a final time and flash frozen in liquid nitrogen. The cold pellet was extracted with 10% ice-cold TCA twice, followed by lyophilization. The dried extract was redissolved in 0.35 mL $D_2O$ and placed in a 5 mm Shigemi tube. NMR spectra were recorded at 14.1 T on a Varian Inova NMR spectrometer (Varian, Inc., Palo Alto, Calif., United States of America) at 20° C. using a 90° excitation pulse. 2-Dimensional TOCSY and HSQC experiments were conducted. Metabolites were assigned based on their $^1H$ and $^{13}C$ chemical shifts and TOCSY connectivity pattern. Metabolites were quantified by integration in the TOCSY experiment.

Protein Extraction and Western Blot Analysis:

Protein extraction and Western blots were performed as previously described. See Telanq et al., *Oncogene*, 25, 7225-7234 (2006). Blots were probed for PFKFB3, stripped and re-probed for β-actin utilizing anti-PFKFB3 (Abjent, Inc., San Diego, Calif., United States of America) and anti-β-actin (Sigma, St. Louis, Mo., United States of America).

Figure 4:
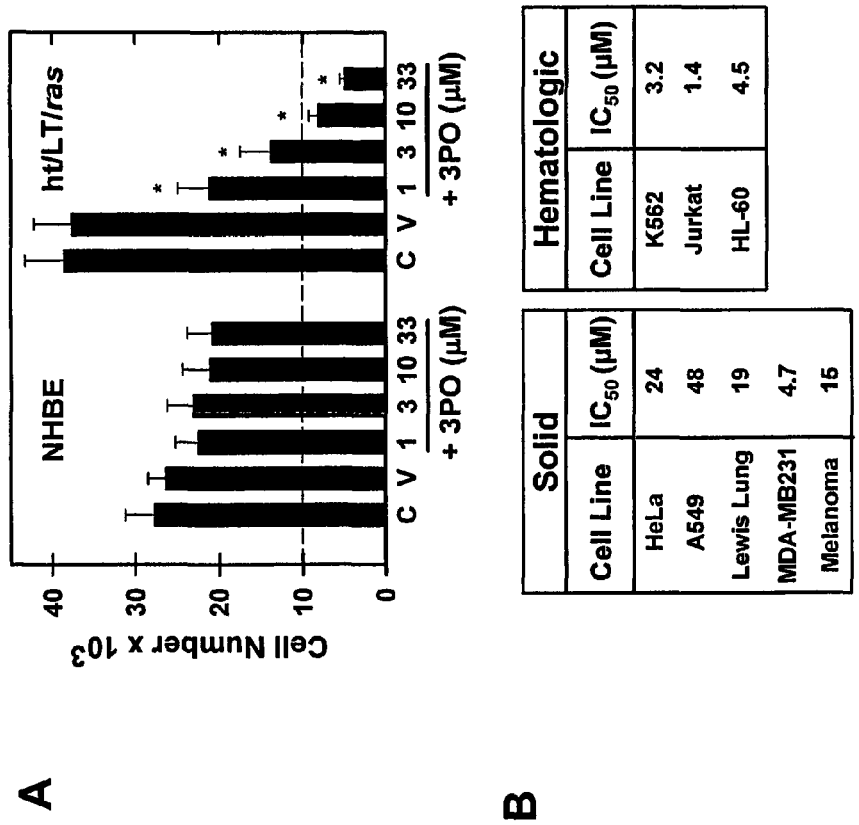
FIG. 4A is a bar graph showing cellular proliferation of NHBE cells (on the left-hand side of the graph) and transformed NHBE cells (ht/Lt/ras, right-hand side of the graph) 48 hours after being treated with 1, 3, 10, or 33 μM 3PO, or vehicle only (V). Untreated control cell populations (C) are also shown. Each bar indicates the mean cell number ($\times 10^3$) of triplicate measurements from a representative experiment. Error bars indicate±one standard deviation (STD); * indicates a p-value<0.01.
FIG. 4B are tables of the $IC_{50}$ values (μM) of compound 1 (i.e., 3PO) in various solid and hematological cell lines. The values are the concentration of 1 needed for 50% of vehicle control cell growth.

Results:

Without being bound to any one particular theory, assuming that increased glycolytic flux is necessary for transformed cell proliferation, the inhibition of PFKFB3 should selectively target tumor cell growth. Transformed NHBE cells (ht/LT/ras) were more sensitive to 1 than the genetically matched primary cells. See FIG. 4A. The primary NHBE cells demonstrated no significant susceptibility to 1 incubation, even at the highest concentration tested (33 µM). However, treatment of the transformed cells with 1 was cytostatic at concentrations below 1 µM, and completely cytotoxic at approximately 10 µM. The $IC_{50}$ for 1 against the NHBE-ht/LT/ras cells was determined to be 1.5 µM. Thus, compound 1 appears to provide a ten-fold greater potent than other inhibitors of glycolysis, 2-DG and 3-BrPA which have effective at concentrations of low mM to 1000, respectively.

The effect of 1 on transformed cells, including lines originating from both solid tumors and hematologically derived disease, was further examined by calculating the $IC_{50}$ of 1 for various tumor cells. The leukemia lines exhibited increased sensitivity (average about 7-fold) to treatment with 1 compared to the adherent cell lines. See FIG. 4B. The $IC_{50}$ values for the K562, Jurkat, and HL-60 leukemia cells were determined to be 3.2, 1.4, and 4.5 respectively. There was a greater $IC_{50}$ variability in the adherent cell lines. Two lung carcinoma models, human A549 and mouse LLC, revealed $IC_{50}$ values of 24 and 19 µM, while HeLa cervical cancer cells had a calculated $IC_{50}$ value of 24 µM. The MDA-MB231 breast adenocarcinoma cells seemed to be especially sensitive to treatment with 1 compared to the other solid tumor derived cell lines, with a calculated $IC_{50}$ of 4.7 µM. Lastly, a melanoma line had an $IC_{50}$ value of 15 µM. Thus, it appears that 1 is an anti-neoplastic compound with an ability to selectively target tumor cell proliferation.

Figure 5A:
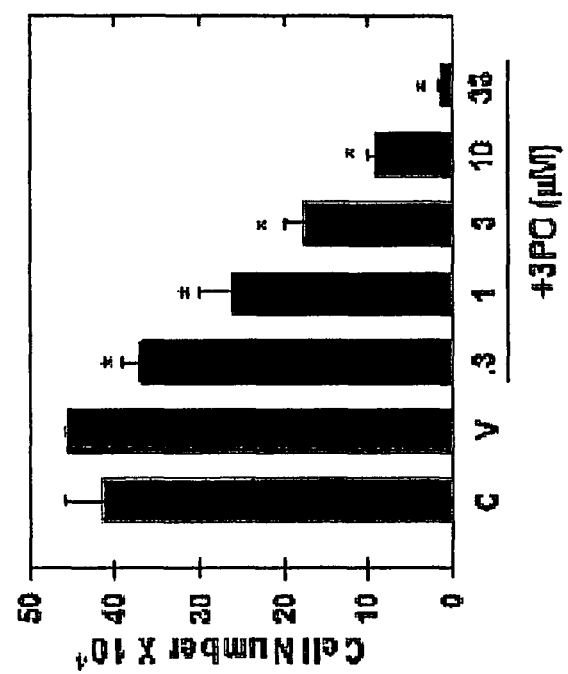
FIG. 5A is a bar graph of the cell growth of Jurkat cells treated with increasing concentrations (0.3, 1, 3, 10, and 33 μM) of 3PO for 36 hours. Cell growth for vehicle treated cells (V) and untreated control Jurkat cells (C) are also shown. Each bar indicates the mean cell number ($\times 10^4$) of triplicate values measured from a representative experiment. Error bars indicate ±one standard deviation (STD); * indicates a p-value<0.01.
Figure 5B:
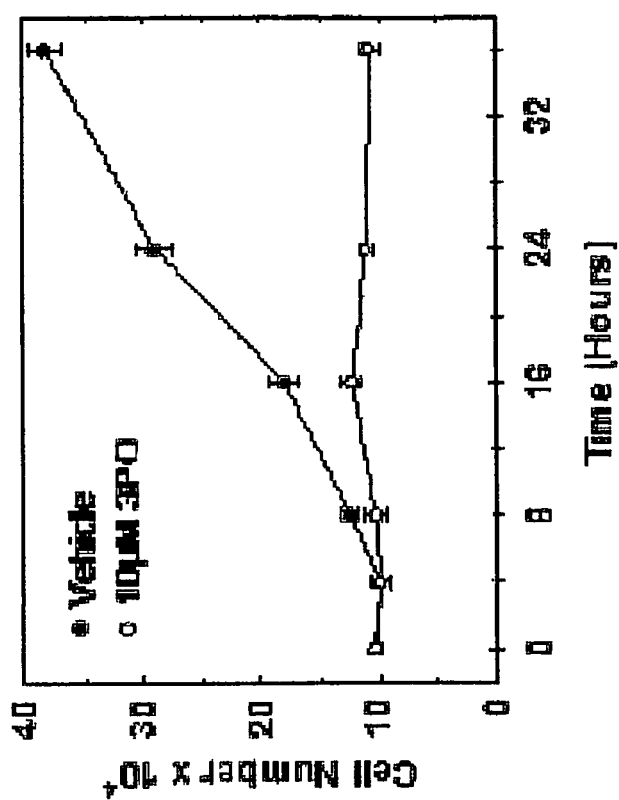
FIG. 5B is a graph showing time-dependent measurements of Jurkat cell growth in the presence of either vehicle (●) or 10 μM 3PO (○). Each data point indicates the mean cell number ($\times 10^4$) measured in three independent experiments. Error bars indicate ±one standard deviation (STD).
Figure 5C:
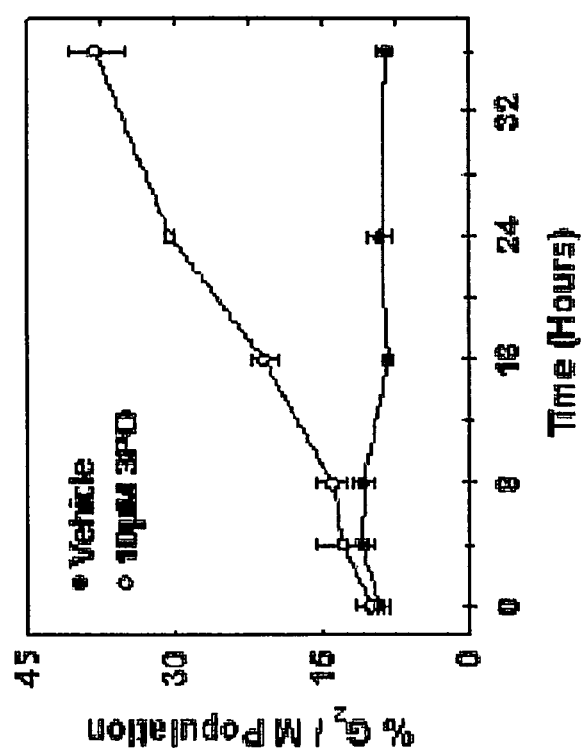
FIG. 5C is a graph showing the percentage (%) $G_2$/M cell cycle population of Jurkat cells over time treated with vehicle (●) or 10 μM 3PO (○). Each data point indicates the mean cell number ($\times 10^4$) measured in three independent experiments. Error bars indicate ±one standard deviation (STD).
Figure 5D:
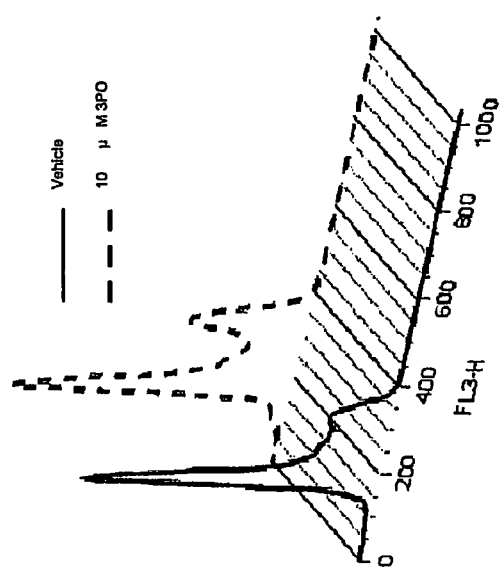
FIG. 5D is a composite cell cycle histogram measured by flow cytometry from Jurkat cells treated with vehicle (solid line) or 10 μM 3PO (dotted line) for 36 hours.
Figure 5E:
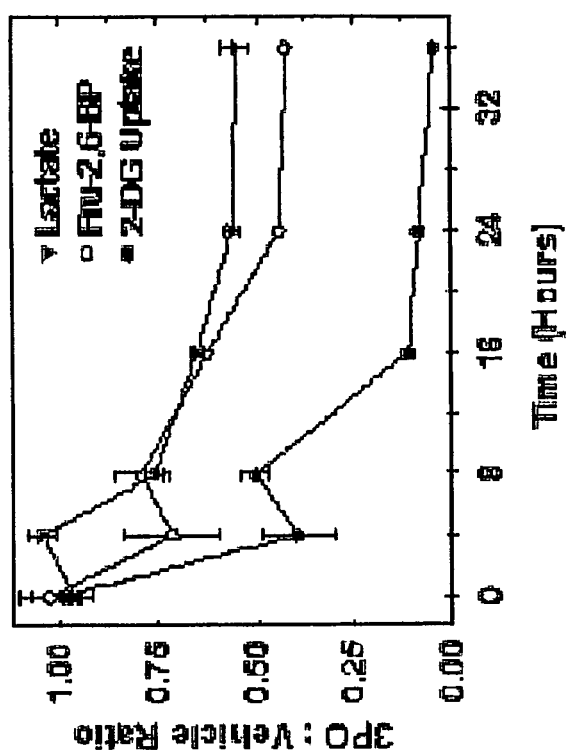
FIG. 5E is a graph showing lactate secretion (▼), 2-deoxyglucose (2-DG) uptake (●), and Fru-2,6-BP production (○) as a function of time in the presence or absence of 10 μM 3PO. Error bars indicate ±one standard deviation (STD).
Figure 5F:
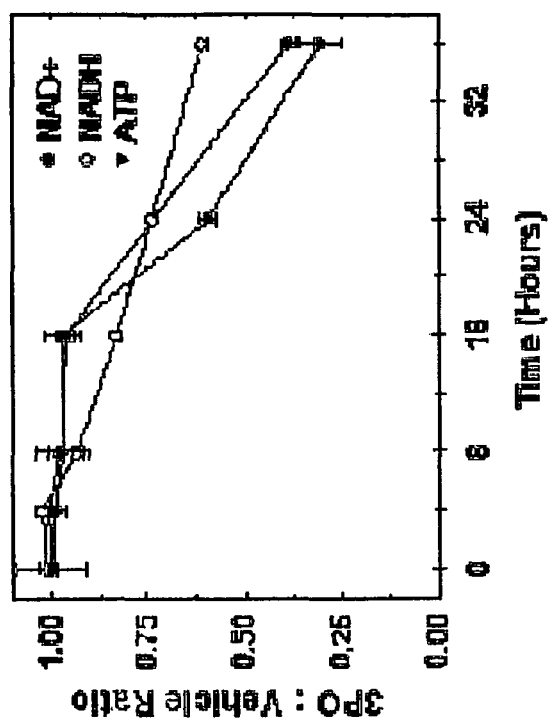
FIG. 5F is a graph showing whole cell NAD+ (●), NADH (○), and ATP (▼) levels as a function of time in the presence or absence of 10 μM 3PO. Error bars indicate ±one standard deviation (STD).
Figure 5G:
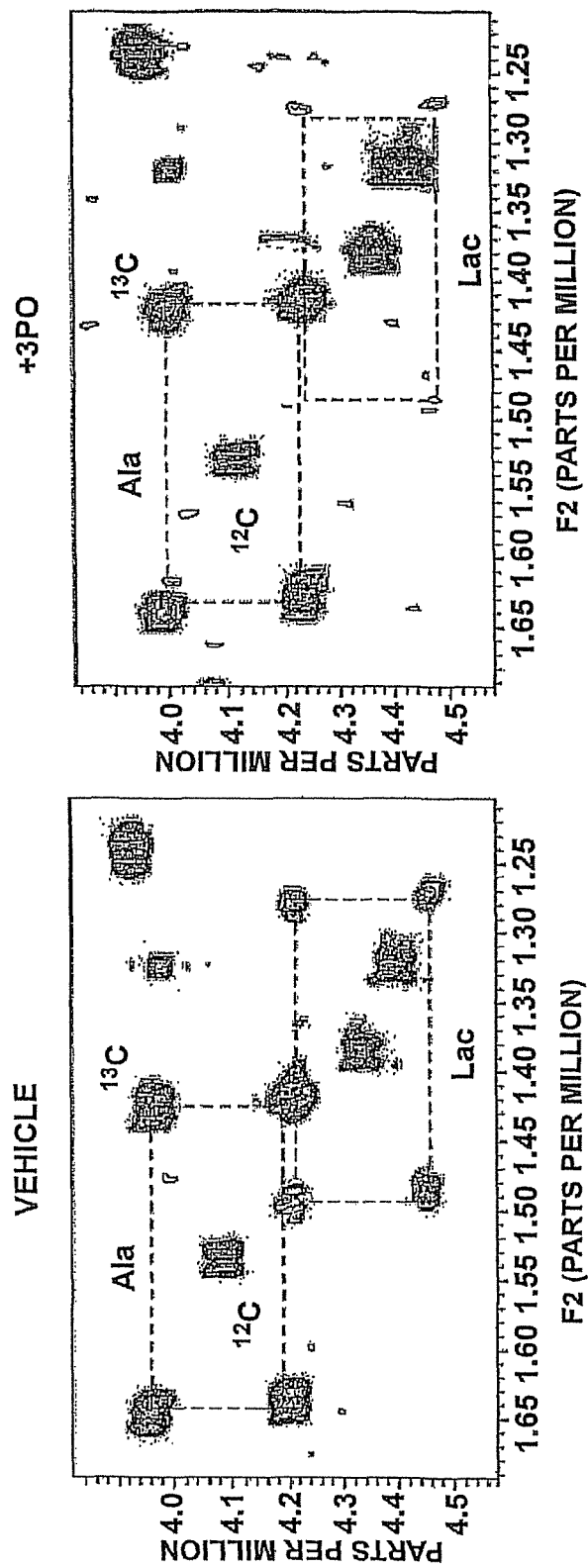
FIG. 5G are two-dimensional (2D) nuclear magnetic resonance (NMR) spectra illustrating $^{13}C$ incorporation into alanine (Ala) and intracellular lactate (Lac) in the presence of vehicle (left-hand spectrum) or 3PO (right-hand spectrum). Shown are representative spectra from three independent experiments. The edges of the dashed line boxes correspond to $^{13}C$ peaks for respective metabolites, which are surrounding the endogenous $^{12}C$ peak in the center.

Incubation with 1 results in a dose-dependent decrease in the proliferation of Jurkat T cell leukemia cells. See FIG. 5A. As little as 0.3 µM 3PO caused a decrease in cell proliferation and 10 µM 3PO completely inhibited proliferation over 36 hours. See FIGS. 5A and 5B. The suppression of cell proliferation appeared to be the result of a $G_2/M$ phase cell cycle arrest as determined by propidium iodide staining. See FIGS. 5C and 5D. The effects of 10 µM 1 on Fru-2,6-BP production, 2-deoxyglucose (2-DG) uptake, and lactate secretion were also investigated. See FIG. 5E. Both 2-DG uptake and Fru-2,6-BP were markedly reduced within 4 hours of exposure. These metabolic changes were followed by a decrease in lactate secretion (see FIG. 5E; 8 hrs), NADH (see FIG. 5F; 16 hrs), NAD+ (see FIG. 5F; 24 hrs) and ATP (see FIG. 5F; 24 hrs). Direct glycolytic flux to lactate was suppressed by pulsing the Jurkat cells with fully-labeled $^{13}C$-glucose during exposure to 1 and examining the fate of the $^{13}C$ atoms by NMR spectroscopy. See FIG. 5G.

Without being bound to any one theory, the observations that 1 decreases intracellular Fru-2,6-BP, 2-DG uptake, and lactate secretion prior to $G_2/M$ phase arrest provide substantial corollary support for the hypothesis that 1 inhibits cellular proliferation through disruption of energetic and anabolic metabolism. The $G_2/M$ arrest caused by 1 can be secondary to the high requirement for ATP during the $G_2/M$ phase of the cell cycle as has been previously observed in HL-60 promyelocytic leukemia cells. See Sweet and Singh, *Cancer Res.*, 55, 5164-5167 (1995). NMR spectroscopic tracking of $^{13}C$-glucose revealed suppression of glycolytic flux into lactate but not alanine. Alanine and lactate share the same pyruvate pool but glucose-derived lactate production can be especially affected by inhibition of glycolysis since lactate dehydrogenase requires a ready supply of NADH, a product of glycolytic flux through glyceraldehyde-3-phosphate dehydrogenase.

One of the most difficult challenges of new anti-neoplastic therapies is in situ target validation. To address this question, two different cell lines with varying levels of PFKFB3 expression were studied. If PFKFB3 is the true target of 1, then the cells which have decreased expression of the enzyme should be more susceptible to treatment with 1, or vice versa. Therefore, PFKFB3 haplo-insufficient (+/−) fibroblasts were immortalized with human telomerase (ht) and large T antigen (LT), and then transformed them with expression of mutated ras (PFKFB3+/−ht/LT/ras). These fibroblasts have been shown to have approximately 50% of PFKFB3 expression and lower F2,6BP production. The +/−ht/LT/ras transformed cells and their wild-type genetic matched counterparts (+/+ ht/LT/ras) were incubated with increasing concentrations of 1.

Figure 6A:
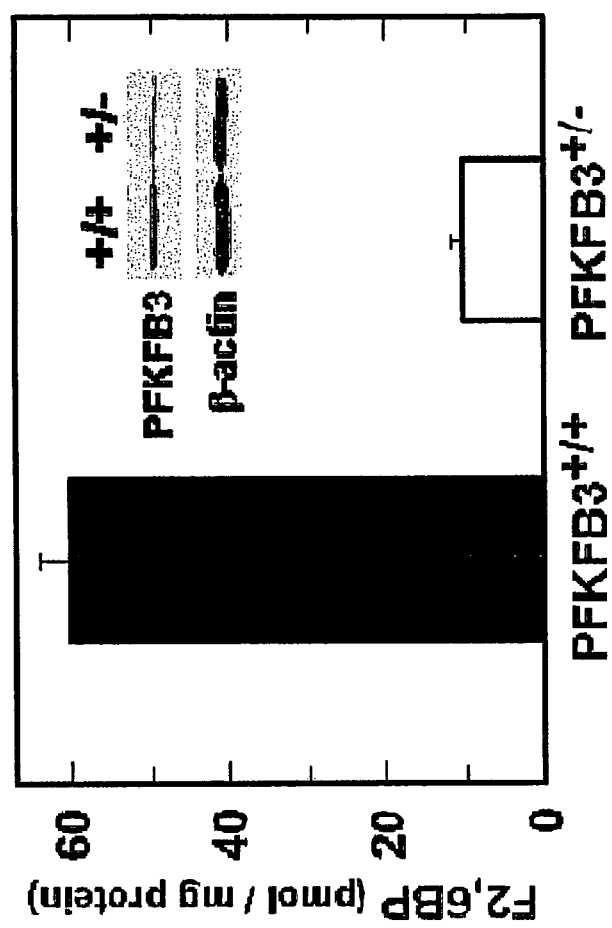
FIG. 6A is a bar graph of cellular levels of F2,5BP measured in fibroblasts from wild-type (+/+) or haplo-insufficient (+/−) PFKFB3 mice which were subsequently immortalized and transformed with human telomerase (ht), large T antigen (LT), and oncogenic H-ras$^{v12}$. The inset shows the Western blot analysis of PFKFB3 expression in the fibroblasts.
Figure 6B:
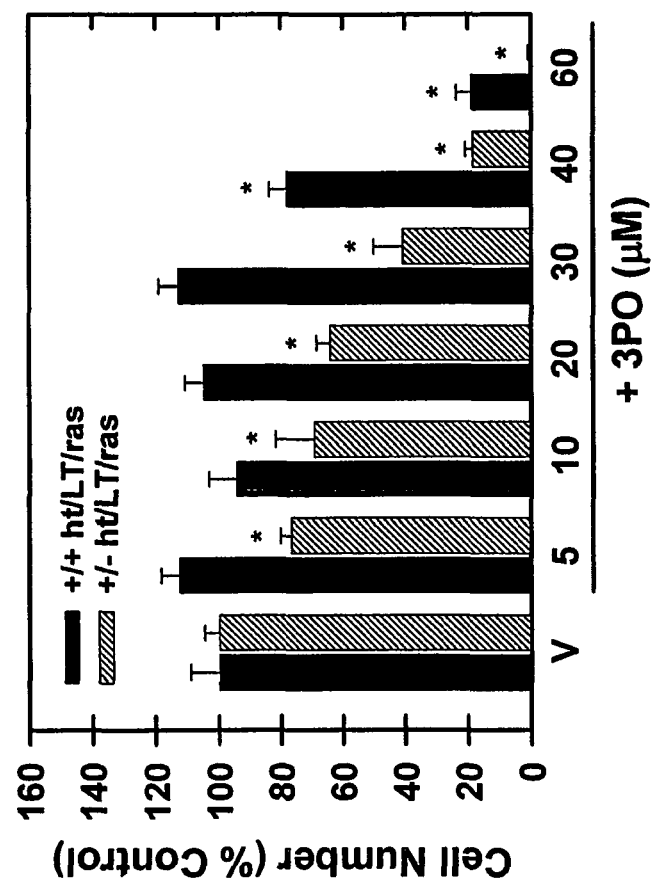
FIG. 6B is a bar graph showing the anti-proliferative effects of 3PO in fibroblasts from wild-type (+/+) or haplo-insufficient (+/−) PFKFB3 mice which were subsequently immortalized and transformed with human telomerase (ht), large T antigen (LT), and oncogenic H-ras$^{v12}$. Cell numbers (expressed as % of cell numbers of control cells) for transformed wild type (+/+) cells are shown in solid bars and numbers for transformed haplo-insufficient (+/−) cells are shown in striped bars. As indicated at the bottom of the graph, cells were incubated with vehicle or increasing amounts of 3PO (5, 10, 20, 30, 40, or 60 μM). Viable cells were counted after 48 hours. The bars represent the mean±STD of triplicate values from a representative experiment. * p-value<0.01 represents statistical difference between vehicle control and 3PO treated samples.

As shown in FIG. 6A, PFKFB3+/−LT/ras transformed fibroblasts express decreased PFKFB3 protein and low intracellular F2,6BP compared to wild-type counterparts. The F2,6BP concentration in the wild type cells was 60.3±3.7 pmol/mg, while in the PFKFB3+/−LT/ras transformed fibroblasts the F2,6BP concentration was 10.3±1.5 pmol/mg. As shown in FIG. 6B, the PFKFB3 heterozygous fibroblasts were more sensitive to treatment with 1 than the wild-type transformed cells. The calculated $IC_{50}$ value for the +/−fibroblasts (26 µM) was determined to be approximately two-fold less than the $IC_{50}$ value for the +/+fibroblasts (49 µM).

Figure 6C:
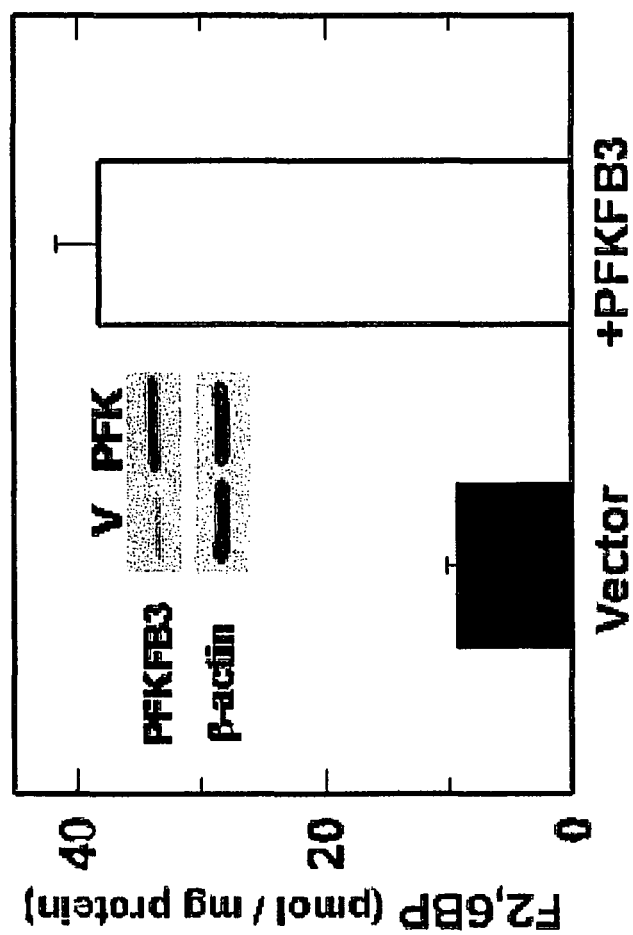
FIG. 6C is a bar graph of cellular levels of F2,5BP measured in Jurkat cells engineered to over-express PFKFB3 through doxycyclin treatment utilizing the Tet-on system (+PFKFB3) and control cells containing an empty vector (Vector). The cells were treated with 1 μg/mL of doxycyclin in order to induce expression of PFKFB3 protein. The inset shows the Western blot analysis of PFKFB3 expression in the cells.
Figure 6D:
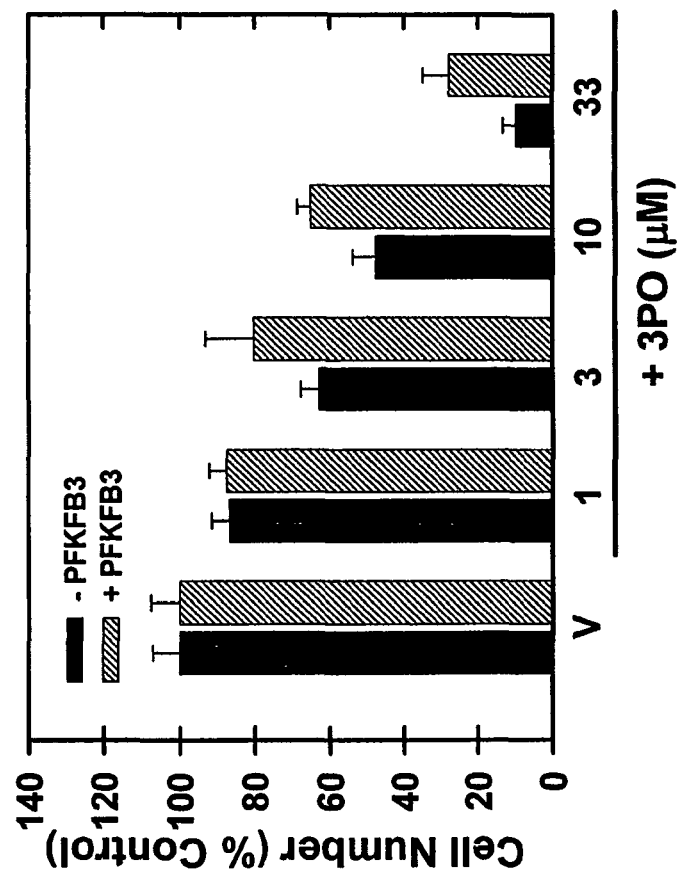
FIG. 6D is a bar graph showing the anti-proliferative effects of 3PO in Jurkat cells engineered to over-express PFKFB3 through doxycyclin treatment utilizing the Tet-on system (+PFKFB3, striped bars). Twenty-four hours prior to 3PO treatment, 1 μg/mL of doxycyclin is incubated with Jurkat cells containing a PFKFB3-expressing vector in order to induce PFKFB3 protein levels. Control cells (−PFKFB3, solid bars) containing an empty vector were similarly treated with doxycyclin and served as background PFKFB3 expression. Both cell types were subsequently incubated with increasing concentrations of 3PO (1, 3, 10, or 33 μM) or vehicle (V), and viable cells were analyzed after 48 hours. The bars represent the mean±STD of triplicate values from a representative experiment.

Conversely, over-expression of PFKFB3 should protect the cell from the diminished cellular proliferation effects of incubation with 1. PFKFB3 levels were manipulated in Jurkat cells under the influence of a doxycycline responsive PFKFB3 Tet-ON system. Addition of doxycycline allows for the increased expression of PFKFB3 compared to doxycyline treated control Jurkat cells with no PFKFB3 expression vector. Ectopic expression of PFKFB3 protein increased F2,6BP concentration. As shown in FIG. 6C, F2,6BP concentration in the +PFKFB3 cells was 38.1±3.4 pmol/mg, while in the control cells, the concentration of F2,6BP was 9.2±0.95 pmol/mg. Both cell types were incubated with increasing concentrations of 1, and as predicted, over-expression of PFKFB3 rescues Jurkat cells from the effects of the inhibitor (FIG. 6D). The $IC_{50}$ values for PFKFB3 over-expressing cells was determined to be 19.3 μM, while Jurkat cells expressing unaltered PFKFB3 levels was calculated as 8.9 μM. Together, these studies demonstrate that by controlling the expression of PFKB3, the cellular inhibitory effects of 1 can be altered, suggesting that PFKFB3 is the valid in situ target of 1.

Example 4

In Vivo Studies with Compound 1

Exponentially growing MDA-MB231 and HL-60 cells were collected in appropriate medium, washed twice and resuspended in PBS at a concentration of $20\times10^7$ cells/mL. Cells were then mixed 1:1 with Matrigel Matrix (BD Biosciences, Bedford, Mass., United States of America), and 0.1 mL of cell suspension was injected subcutaneously ($1\times10^7$ cells) into female Balb/c nude mice (20 g). Exponentially growing Lewis Lung Carcinoma cells were collected, washed twice, and resuspended in PBS ($1\times10^7$/mL). C57Blk/6 female mice (20 g) were injected subcutaneously with $1\times10^6$ cells in 0.1 mL volume. Body weight and tumor growth were monitored daily throughout the study. Tumor masses were determined by measurement with Vernier calipers using the formula: mass (mg)=[width ($mm^2$)×length (mm)]/2. See Taetle et al., *Cancer Treat. Rep.*, 71, 297-304 (1987). Mice with established tumors (between 130 mg-190 mg) were randomized into vehicle control or compound 1 treated groups. Vehicle control groups received intraperitoneal (i.p.) injections of 50 μL dimethyl sulfoxide (DMSO), while treated groups received i.p. injections of 0.07 mg/g 1 in 50 μL DMSO at the indicated time points.

Figure 7A:
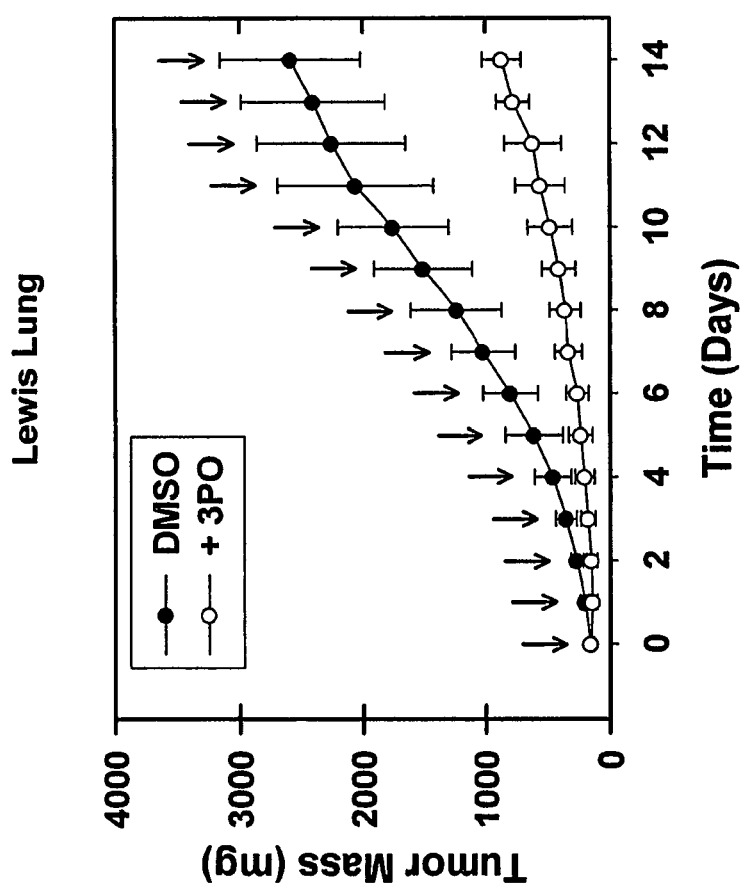
FIG. 7A is a graph showing the effects of 3PO treatment on the growth of Lewis Lung Carcinoma tumor xenografts in C57/Blk6 mice. Tumors were measured daily using blunt end Vernier calipers, and mice with established tumors (130-190 mg) were blindly randomized into either a DMSO control group (•, n=11) or a 3PO treatment group (○, n=14). Experimental mice were weighed and given daily intraperitoneal (i.p.) injections of either 50 μL DMSO or 0.07 mg/g 3PO in 50 μL DMSO at the indicated time points. Arrows (↓) represent control or 3PO daily administrations. Statistically significant difference between DMSO and 3PO groups was obtained after initial injection (Day 2, p-value<0.0003).
Figure 7B:
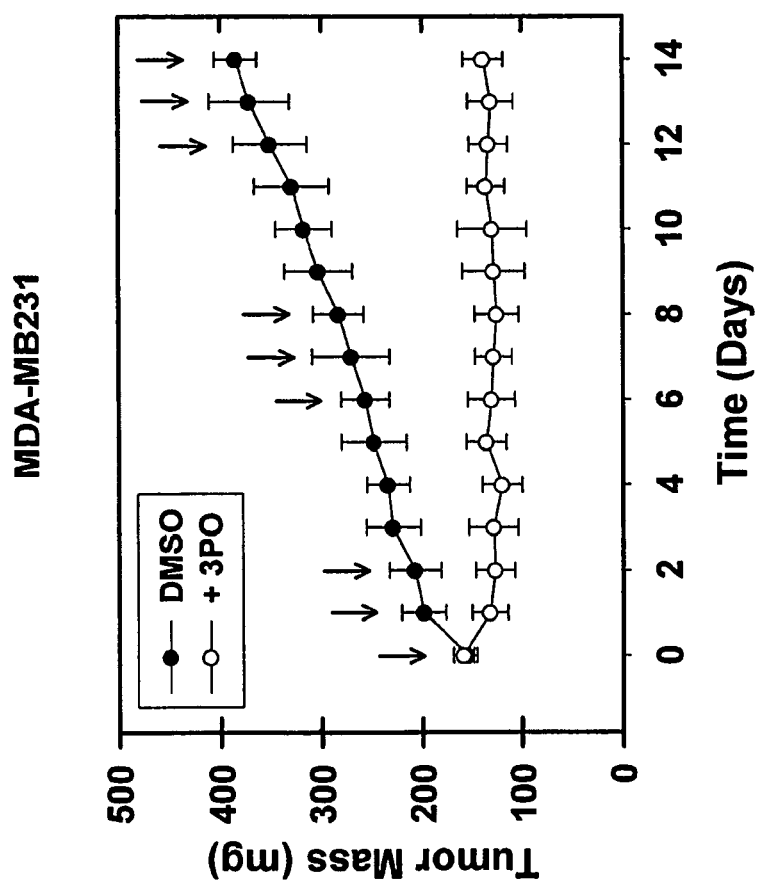
FIG. 7B is a graph showing the effects of 3PO treatment on the growth of established MDA-MB231 breast adenocarcinoma tumor zenografts in Balb/c athymic mice. Tumors were measured daily using blunt end Vernier calipers, and mice with established tumors (130-190 mg) were blindly randomized into either a DMSO control group (•, n=14) or a 3PO treatment group (○, n=13). Experimental mice were weighed and given intraperitoneal (i.p.) injections of either 50 μL DMSO or 0.07 mg/g 3PO in 50 μL DMSO according to a cyclical dosing regimen of three sequential daily injections followed by three off days for the duration of the study (14 days). Arrows (↓) represent control or 3PO administrations. Statistical difference between the DMSO control and 3PO experimental groups was observed on day 2 (p-value<0.0001).
Figure 7C:
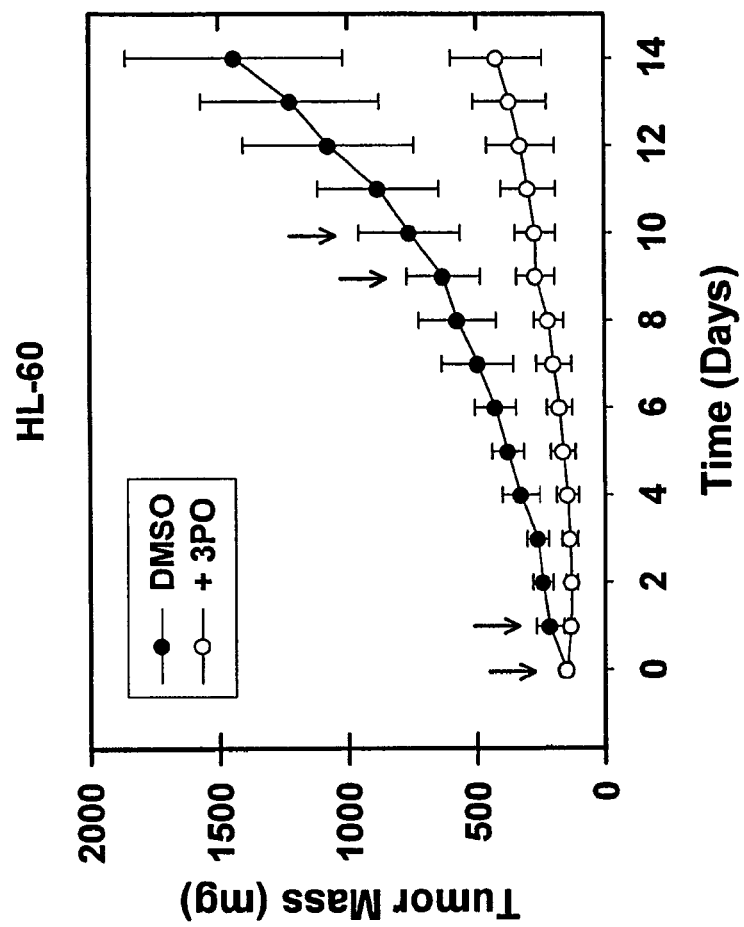
FIG. 7C is a graph showing the effects of 3PO treatment on the growth of established HL-60 acute promyelocytic leukemia xenografts in Balb/c athymic mice. Tumors were measured daily using blunt end Vernier calipers, and mice with established tumors (130-190 mg) were blindly randomized into either a DMSO control group (•, n=11) or a 3PO treatment group (○, n=12). Experimental mice were weighed and given intraperitoneal (i.p.) injections of either 50 μL DMSO or 0.07 mg/g 3PO in 50 μL DMSO according to a cyclical dosing regimen of two sequential daily injections of DMSO or 3PO followed by seven day rest period for the duration of the study (14 days). Arrows (↓) represent control or 3PO administrations. Statistical difference was obtained after initial injection with a p-value<0.0001.

Results:

Toxicity studies of 1 found that the highest tolerated dose producing no phenotypic side effects was intraperitoneal (IP) injection of 0.07 mg/g in DMSO. The first tumor model tested consisted of mouse Lewis Lung Carcinoma xenografts grown in C57/Blk6 mice. For this study, mice were given IP injections of either DMSO or the calculated dose of 1 once daily for the duration of the study (14 days). As illustrated in FIG. 7A, administration of 1 significantly suppresses the growth of Lewis Lung Carcinoma xenografts by 73% compared to the DMSO control group. Separately, MDA-MB231 human breast adenocarcinoma tumors were established in Balb/c nude mice. In this model, the frequency of the dose was decreased to determine whether reduced treatment would yield the same efficacy as seen in the Lewis Lung Carcinoma model. For both DMSO (control) and compound 1 treatment groups, mice were given a cyclical regiment of three daily injections followed by three days of no treatment. Total inhibition of xenograft growth of MDA-MB231 cells was observed compared to the DMSO controls (FIG. 7B) with a maximum inhibition of 66%. The third in vivo model comprised HL-60 leukemia cell xenografts in Balb/c nude mice. The treatment schedule was further reduced to include a regiment of two sequential daily injections followed by seven consecutive days of no injections. As demonstrated in FIG. 7C, treatment with compound 1, even in limited dosing, significantly inhibited HL-60 tumor growth by upwards of 74% compared to DMSO controls. Furthermore, the efficacy of the second dosing regiment is visible on the proliferation curve by the reduction in growth seen after treatment on day 9. The effects of 1 on the Lewis Lung Carcinoma and HL-60 xenograft models appear to be cytostatic since no regression in tumor growth was evident. However, the MDA-MB231 model suggests that compound 1 inhibition encompasses both an early cytotoxic effect, leading to initial tumor regression, followed by cytostatic properties as seen in the other two models. Together, these data support compound 1 as a potential anti-neoplastic agent for its ability to reduce in vivo tumor proliferation.

Example 5

Inhibition of PFKFB3 By Compounds 2-7

Figure 8:
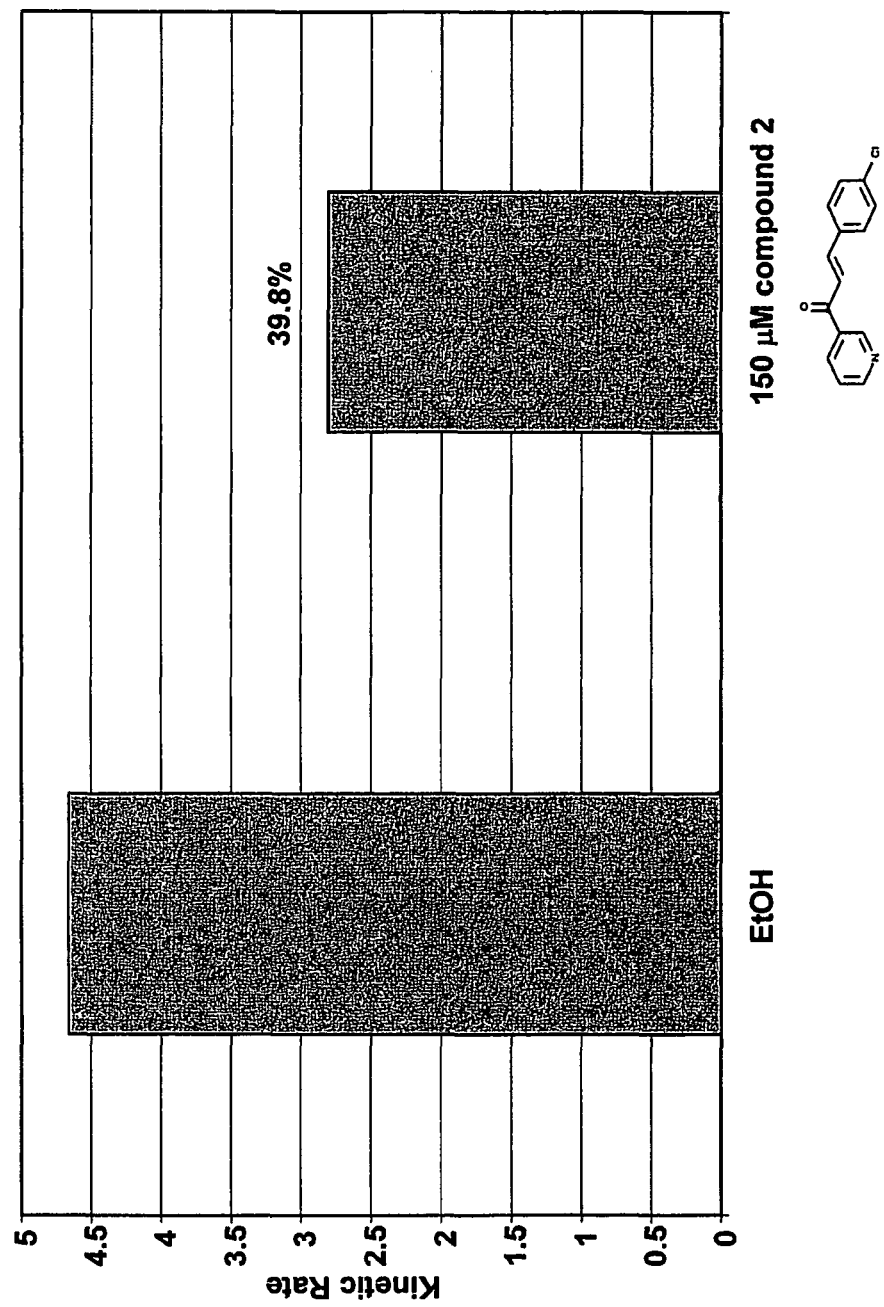
FIG. 8 is a bar graph showing the PFKFB3 inhibitory activity of compound 2,3-(4-chlorophenyl)-1-(3-pyridinyl)-2-propen-1-one. The kinetic rate of recombinant PFKFB3 treated with 150 μM 2 was 39.8% of that observed with PFKFB3 treated with the same volume of vehicle (EtOH).
Figure 9:
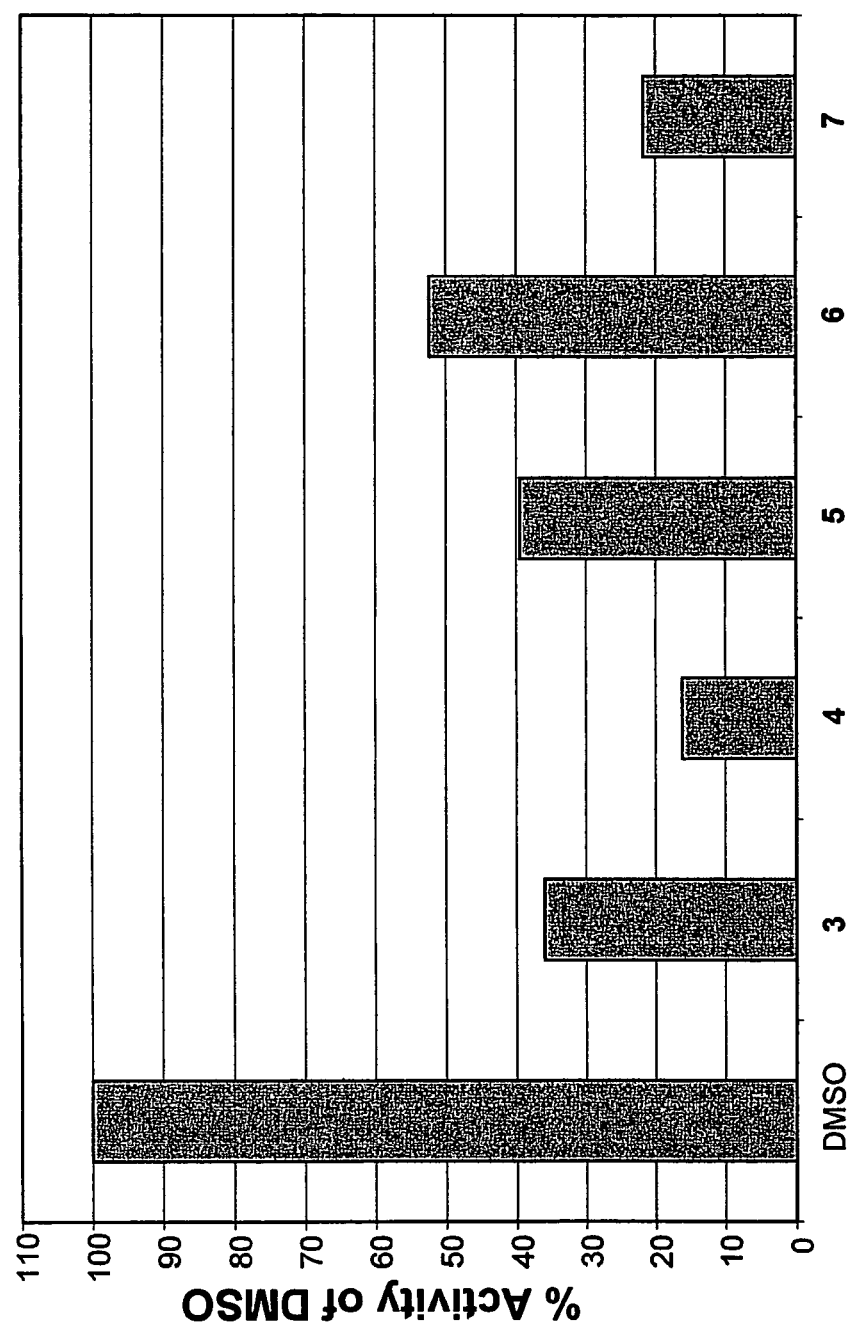
FIG. 9 is a bar graph showing the PFKFB3 inhibitory activity of compounds 3 (i.e., 3-(1-napthyl)-1-(4-pyridinyl)-2-propen-1-one), 4 (i.e., 1-(3-pyridinyl)-3-(2-quinolinyl)-2-propen-1-one), 5 (i.e., N-{4-[3-oxo-3-(4-pyridinyl)-1-propen-1-yl]phenyl}acetamide), 6 (i.e., 3-(2-chlorophenyl)-1-(2-pyridinyl)-2-propen-1-one), and 7 (i.e., 3-(2-chlorophenyl)-1-(3-pyridinyl)-2-propen-1-one) compared to the activity of vehicle (DMSO)-treated enzyme.

The ability of compounds 2-7 to inhibit PFKFB3 activity in vitro was determined using the enzymatic assay methods described above in Example 2. Treatment with 150 μM compound 2 caused the kinetic rate of PFKFB3 to be reduced 39.8% compared to treatment with vehicle (EtOH). See FIG. 8. The inhibitory effects of compounds 3-7 compared to vehicle (DMSO) treatment are compared in FIG. 9. Compound 4 reduced PFKFB3 the most, by over 80%.

Example 6

Toxicity of Compounds 2-7 in Transformed Tumor Cells

Figure 10:
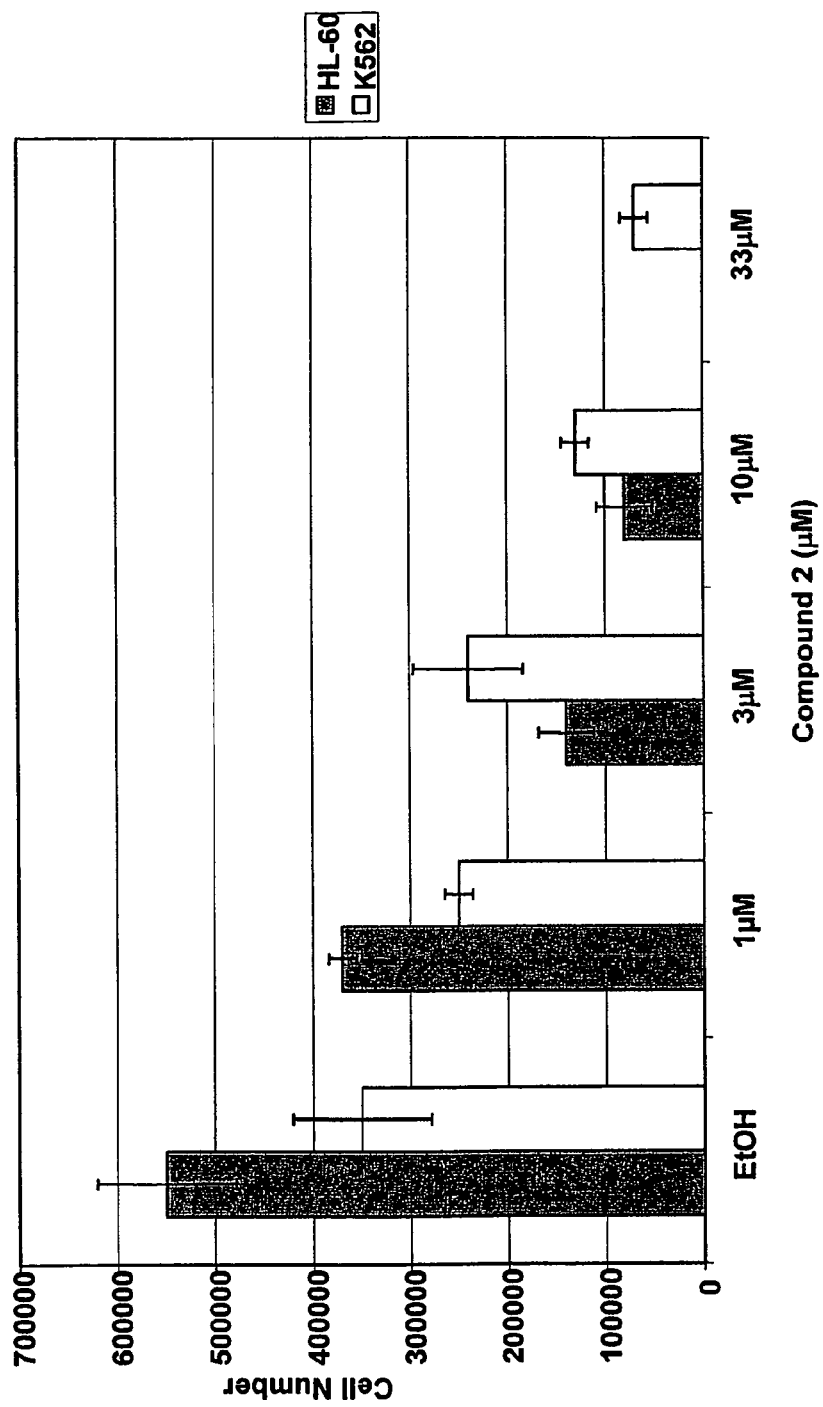
FIG. 10 is a bar graph showing cellular proliferation of HL-60 cells (dark bars) and K562 cells (light bars) treated with increasing concentrations (1, 3, 10, or 33 μM) of compound 2 or with vehicle (EtOH). The bars represent the mean±STD of triplicate values from a representative experiment.
Figure 11:
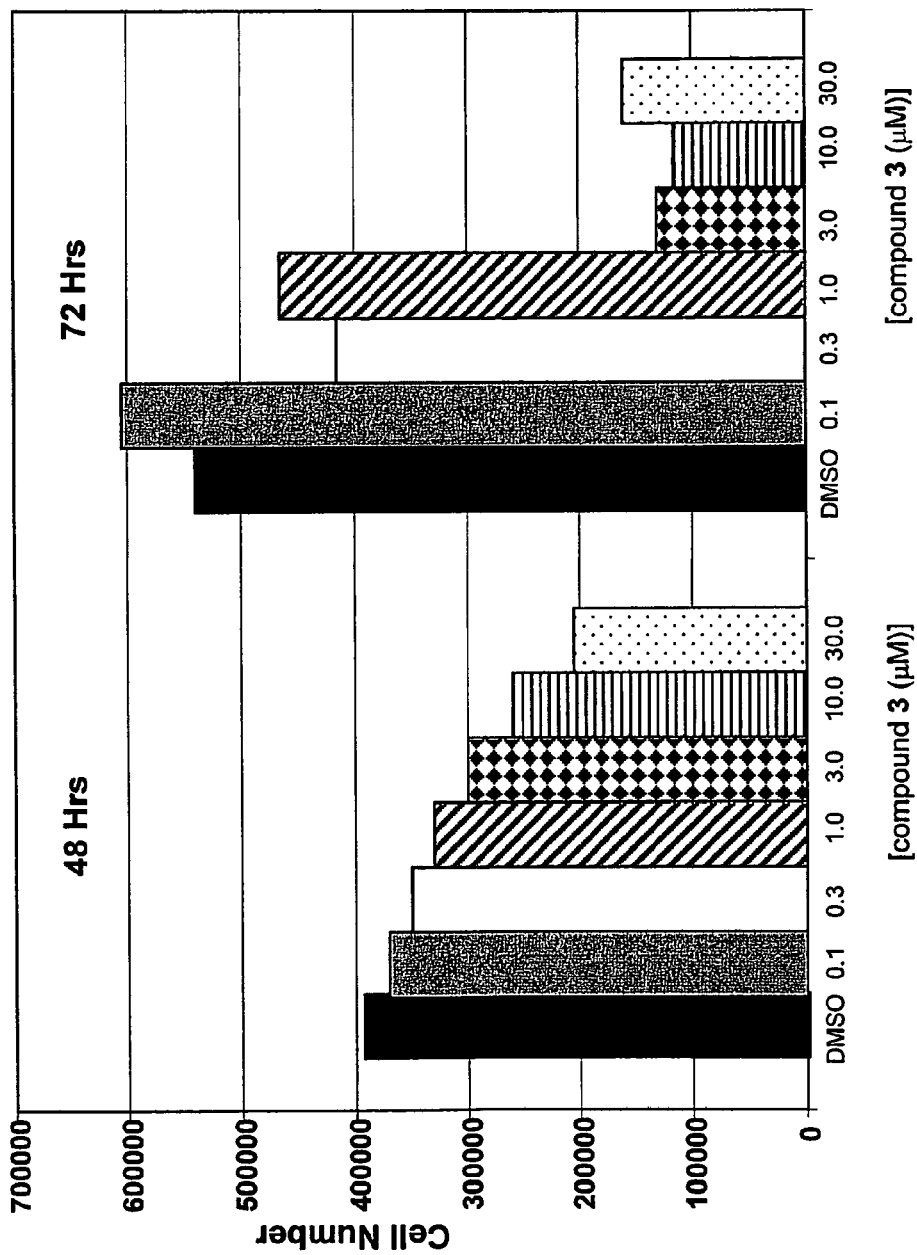
FIG. 11 is a bar graph showing cellular proliferation of Jurkat cells treated with compound 3 at concentrations of 0.1 (medium grey bars), 0.3 (uncolored bars), 1.0 (diagonally striped bars), 3.0 (diamond filled bars), 10.0 (horizontally striped bars), or 30.0 (dotted bars) μM for 48 or 72 hours as indicated at the top of the graph. Cellular proliferation of Jurkat cells treated with DMSO (dark colored bars) for 48 or 72 hours is also shown.
Figure 12:
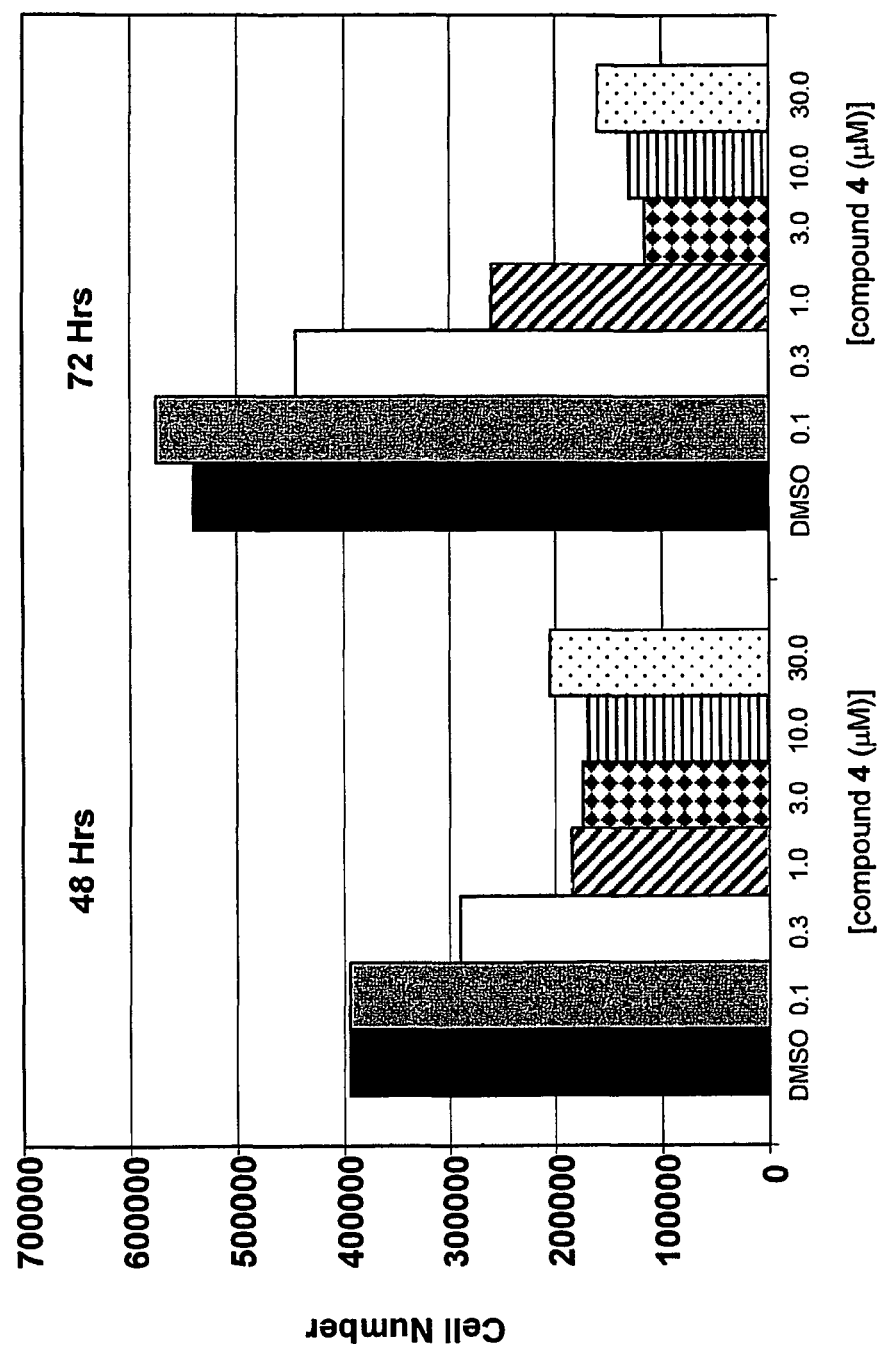
FIG. 12 is a bar graph showing cellular proliferation of Jurkat cells treated with compound 4 at concentrations of 0.1 (medium grey bars), 0.3 (uncolored bars), 1.0 (diagonally striped bars), 3.0 (diamond filled bars), 10.0 (horizontally striped bars), or 30.0 (dotted bars) μM for 48 or 72 hours as indicated at the top of the graph. Cellular proliferation of Jurkat cells treated with DMSO (dark colored bars) for 48 or 72 hours is also shown.
Figure 13:
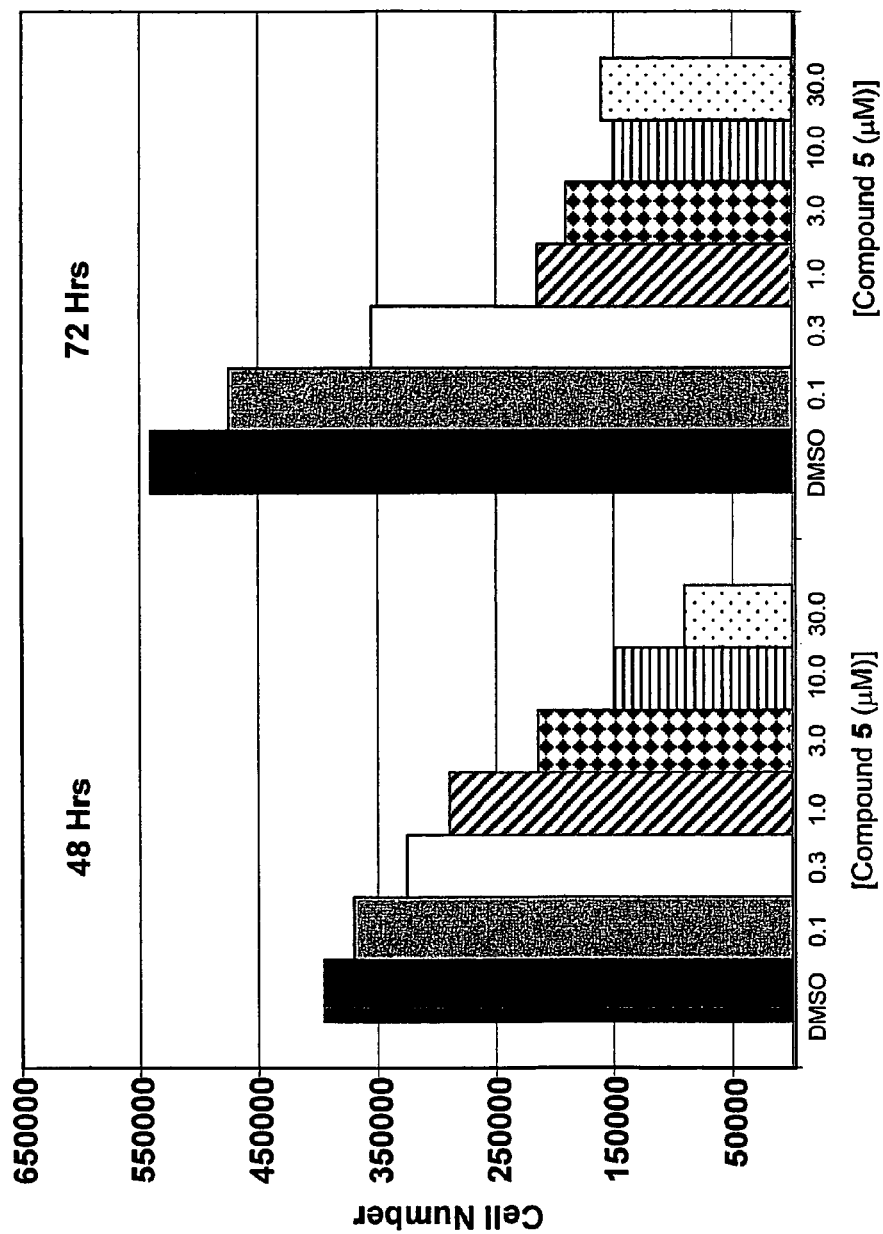
FIG. 13 is a bar graph showing cellular proliferation of Jurkat cells treated with compound 5 at concentrations of 0.1 (medium grey bars), 0.3 (uncolored bars), 1.0 (diagonally striped bars), 3.0 (diamond filled bars), 10.0 (horizontally striped bars), or 30.0 (dotted bars) μM for 48 or 72 hours as indicated at the top of the graph. Cellular proliferation of Jurkat cells treated with DMSO (dark colored bars) for 48 or 72 hours is also shown.
Figure 14:
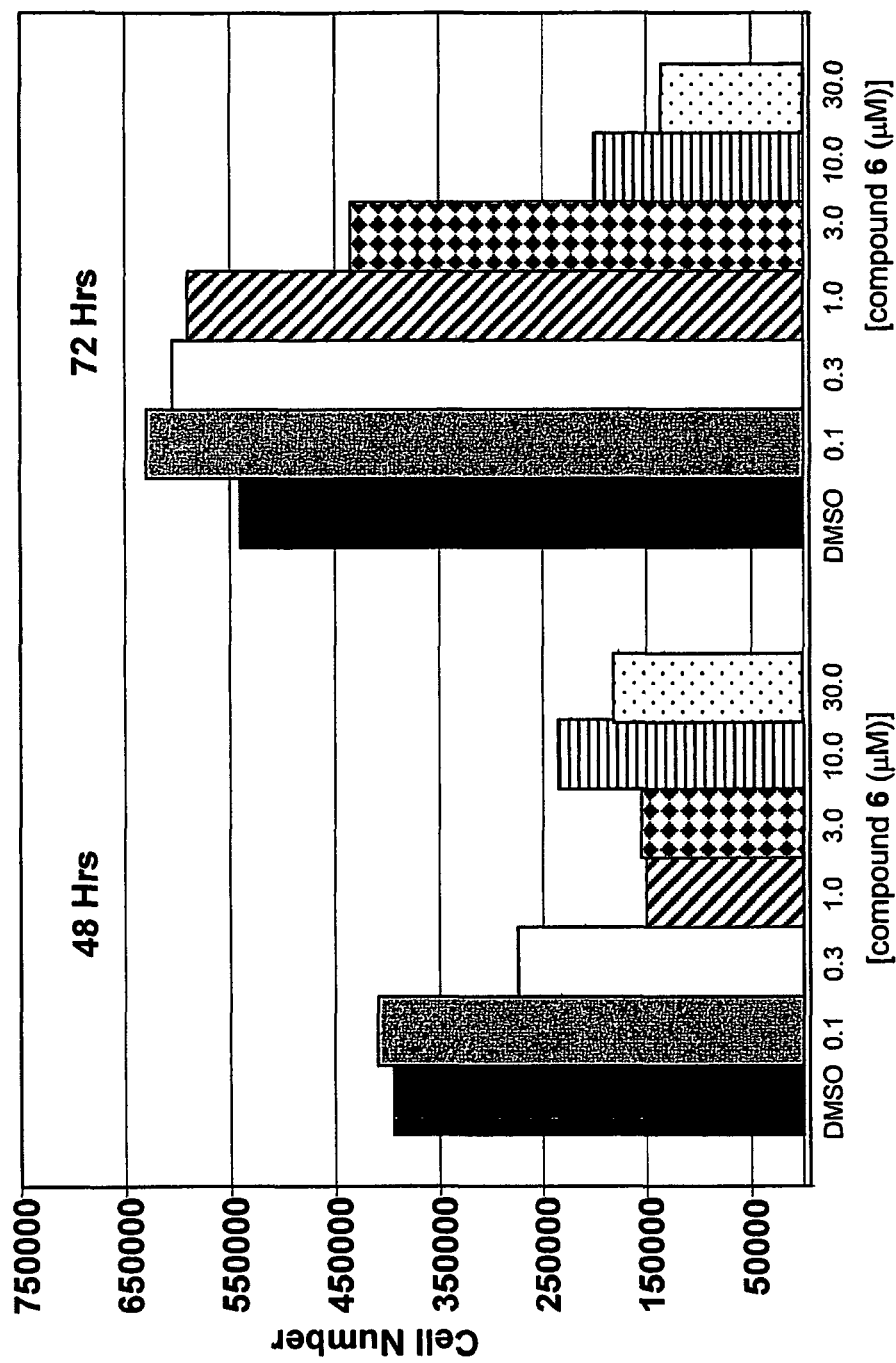
FIG. 14 is a bar graph showing cellular proliferation of Jurkat cells treated with compound 6 at concentrations of 0.1 (medium grey bars), 0.3 (uncolored bars), 1.0 (diagonally striped bars), 3.0 (diamond filled bars), 10.0 (horizontally striped bars), or 30.0 (dotted bars) μM for 48 or 72 hours as indicated at the top of the graph. Cellular proliferation of Jurkat cells treated with DMSO (dark colored bars) for 48 or 72 hours is also shown.
Figure 15:
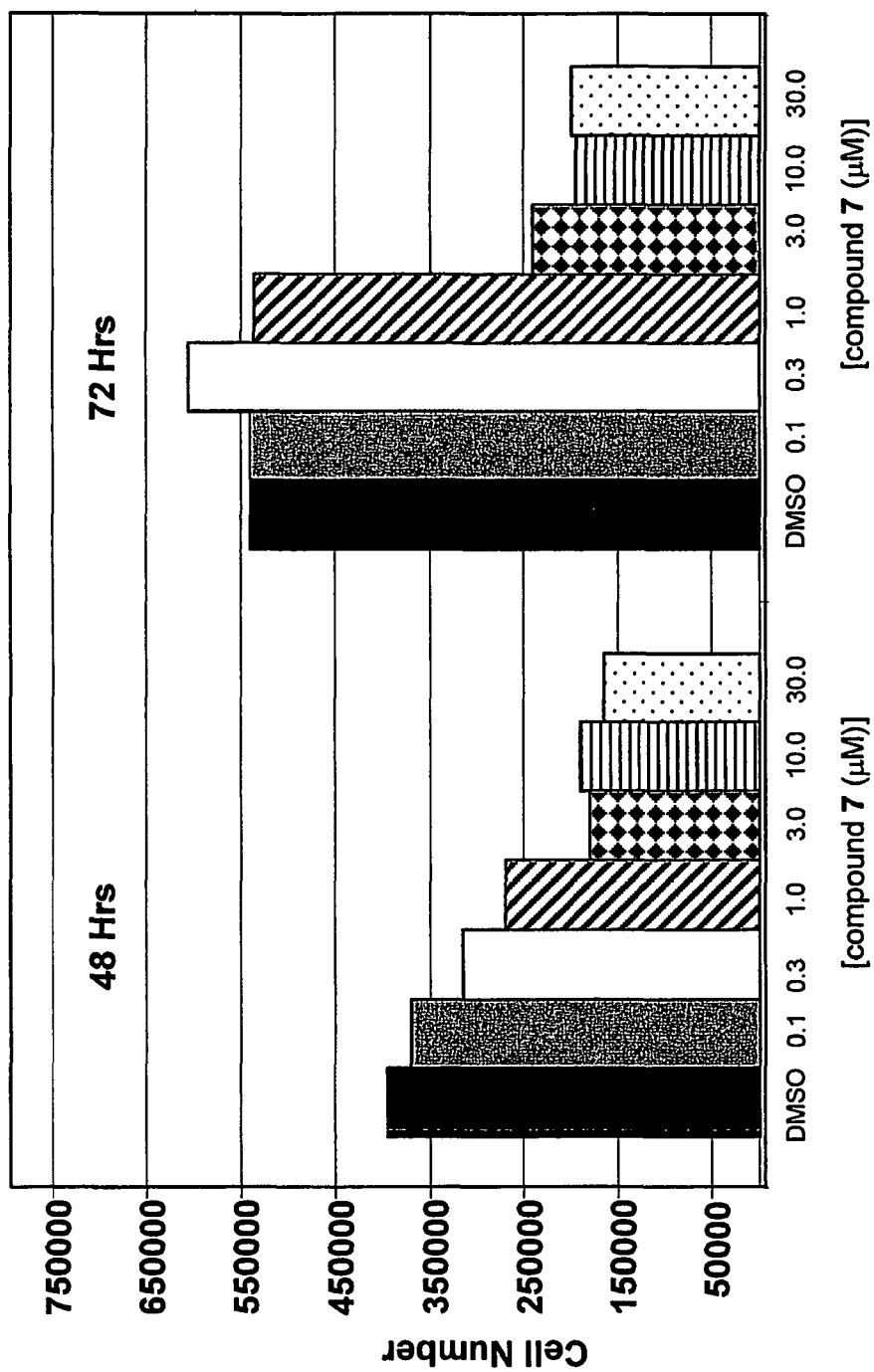
FIG. 15 is a bar graph showing cellular proliferation of Jurkat cells treated with compound 7 at concentrations of 0.1 (medium grey bars), 0.3 (uncolored bars), 1.0 (diagonally striped bars), 3.0 (diamond filled bars), 10.0 (horizontally striped bars), or 30.0 (dotted bars) μM for 48 or 72 hours as indicated at the top of the graph. Cellular proliferation of Jurkat cells treated with DMSO (dark colored bars) for 48 or 72 hours is also shown.
Figure 16:
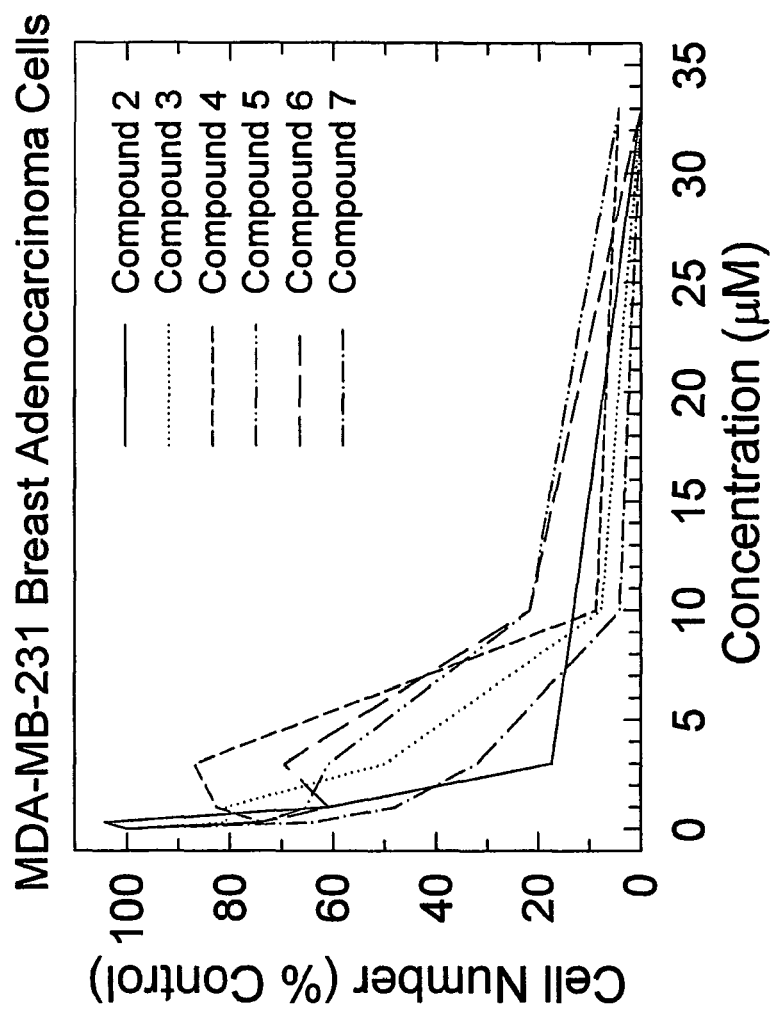
FIG. 16 is a graph showing the growth and survival of MDA-MB-231 breast adenocarcinoma cells in the presence of compounds 2-7 (at 0.3-33 µM).
Figure 17:
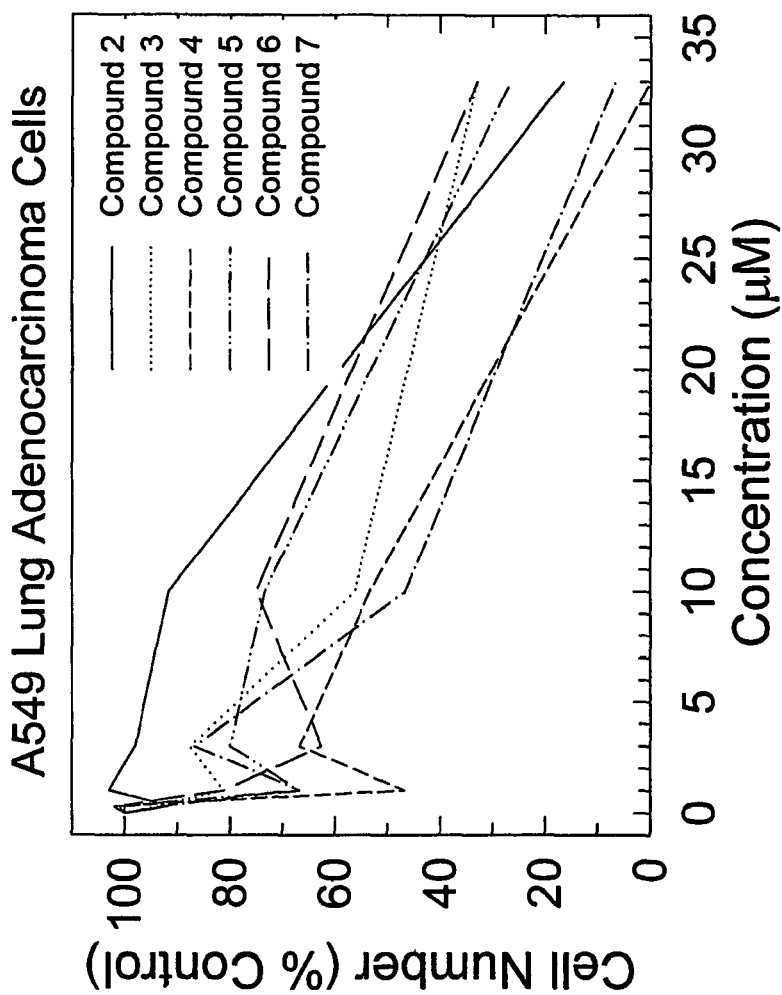
FIG. 17 is a graph showing the growth and survival of A549 lung adenocarcinoma cells in the presence of compounds 2-7 (at 0.3-33 µM).
Figure 18:
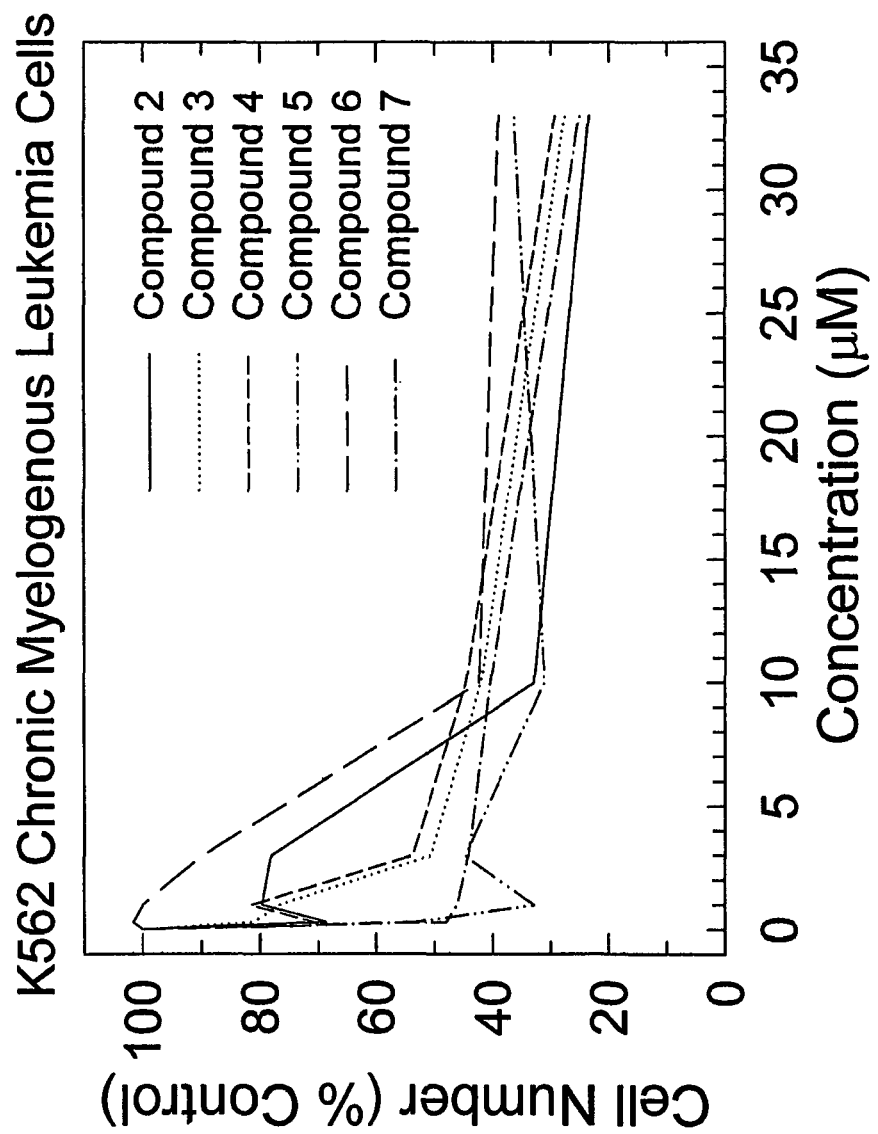
FIG. 18 is a graph showing the growth and survival of K562 chronic myelogenous leukemia cells in the presence of compounds 2-7 (at 0.3-33 µM).
Figure 19:
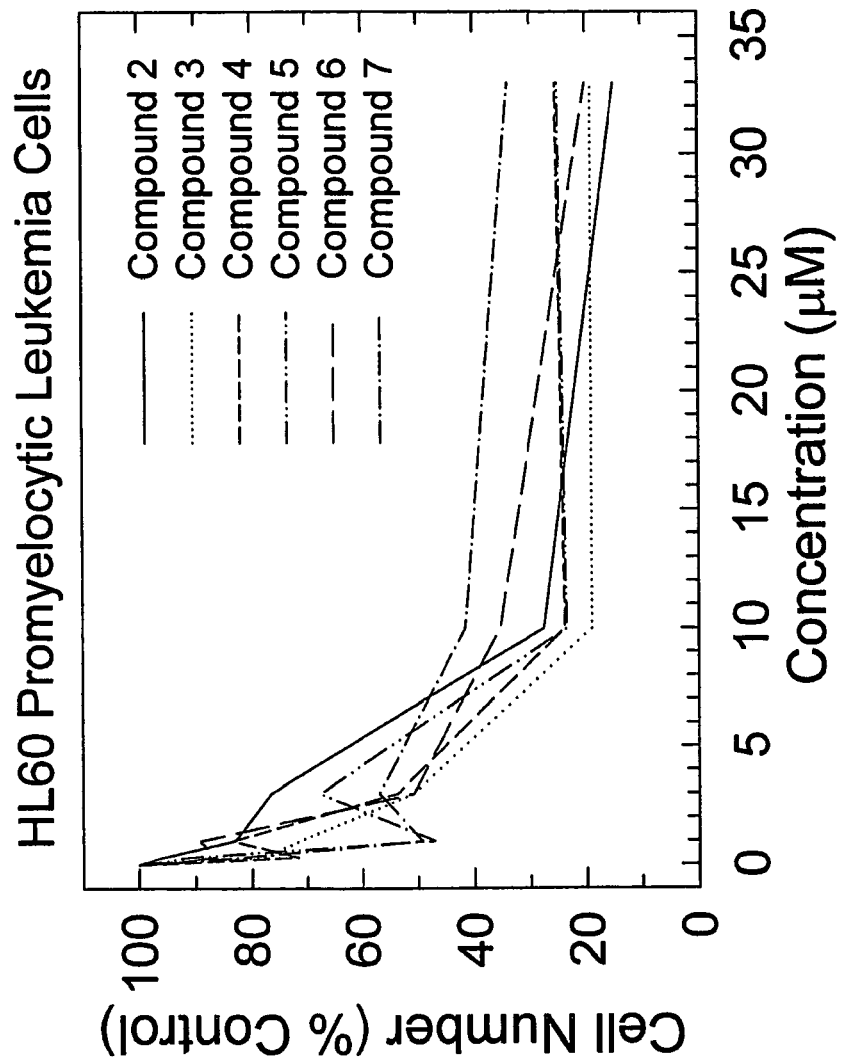
FIG. 19 is a graph showing the growth and survival of HL60 promyelocytic leukemia cells in the presence of compounds 2-7 (at 0.3-33 µM).
Figure 20:
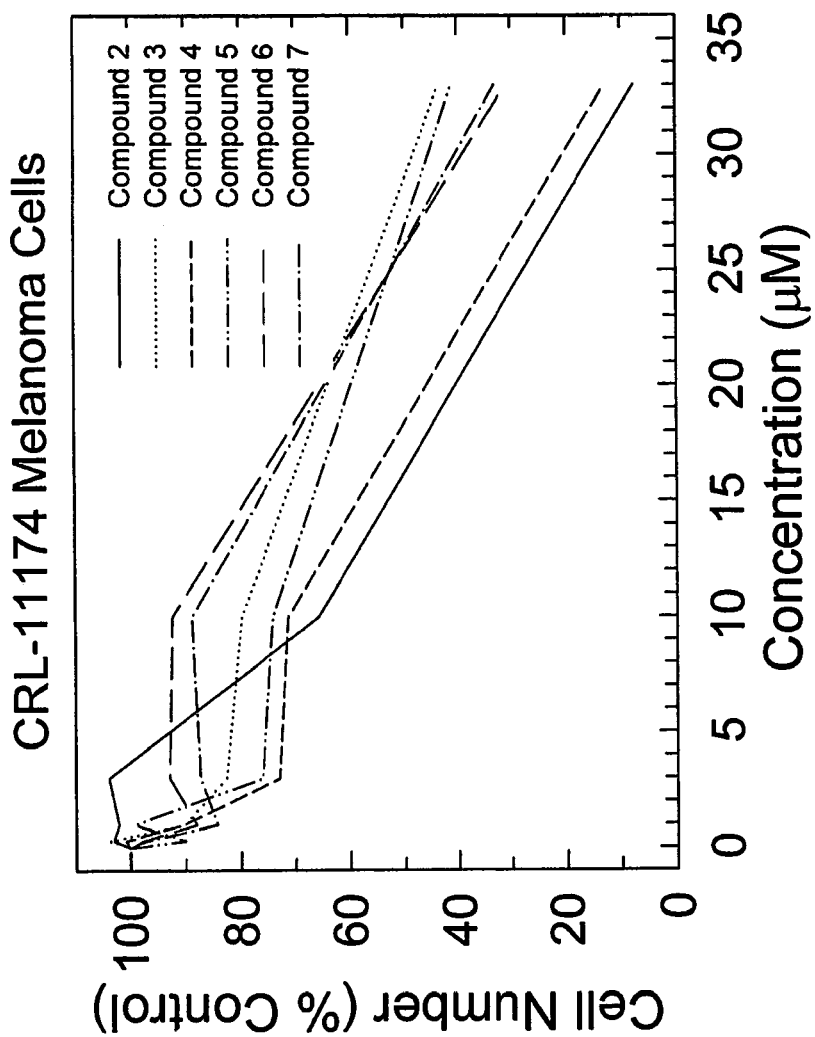
FIG. 20 is a graph showing the growth and survival of CRL-11174 melanoma cells in the presence of compounds 2-7 (at 0.3-33 µM).
Figure 21:
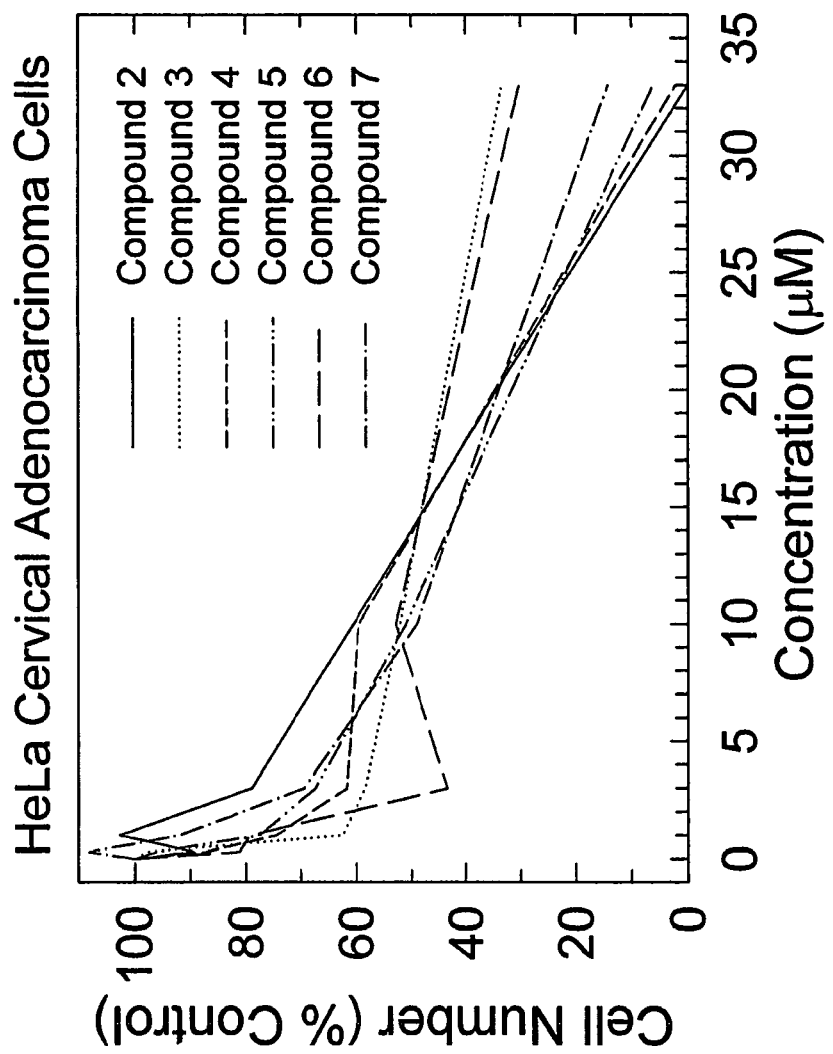
FIG. 21 is a graph showing the growth and survival of HeLa cervical adenocarcinoma cells in the presence of compounds 2-7 (at 0.3-33 µM).

The toxicity of compounds 2-7 toward various transformed cell lines was assessed as described hereinabove in Example 3. Compound 2 displayed dose-dependent cellular toxicity in two types of leukemia cell lines, HL-60 and K562 cells. See FIG. 10. The effects of various concentrations of compounds 3-7 on Jurkat leukemia cell proliferation are shown in FIGS. 11-15.

FIGS. 16-21 show the effects of compounds 2-7 in various transformed cells treated with 0.3, 1, 3, 10, or 33 μM of compound. All six of compounds 2-7 inhibited the proliferation of each examined solid tumor and hematologic cell type.

Example 7

Effects of Compound 1 on Glucose Uptake Observed by Micro-Pet

C57Bl/6 female mice (20 g) were injected subcutaneously with $1\times10^6$ Lewis lung carcinoma cells. When the xenografts were measured to have a mass of between 150 and 180 mg, the mice were split into two groups. One group was injected i.p. with 0.07 mg/g of compound 1. The other group was used as a control and injected i.p. with 50 μL DMSO. Four hours post-injection, tumors were removed and homogenized in equal volumes of 0.1 M and 0.05 M NaOH. F2,6BP assays were performed as previously described. See Van Shaftingen et al., *Eur. J. Biochem*, 129, 191-195 (1982). Compound 1 treatment significantly reduced F2,6BP production in the tumor xenografts compared to vehicle control. F2,6BP concentration in the compound 1-treated mouse xenografts was 8.5±1.7 pmol/mg, while in the control mouse xenografts' F2,6BP concentration was 13.1±1.9 pmol/mg.

Figure 22:
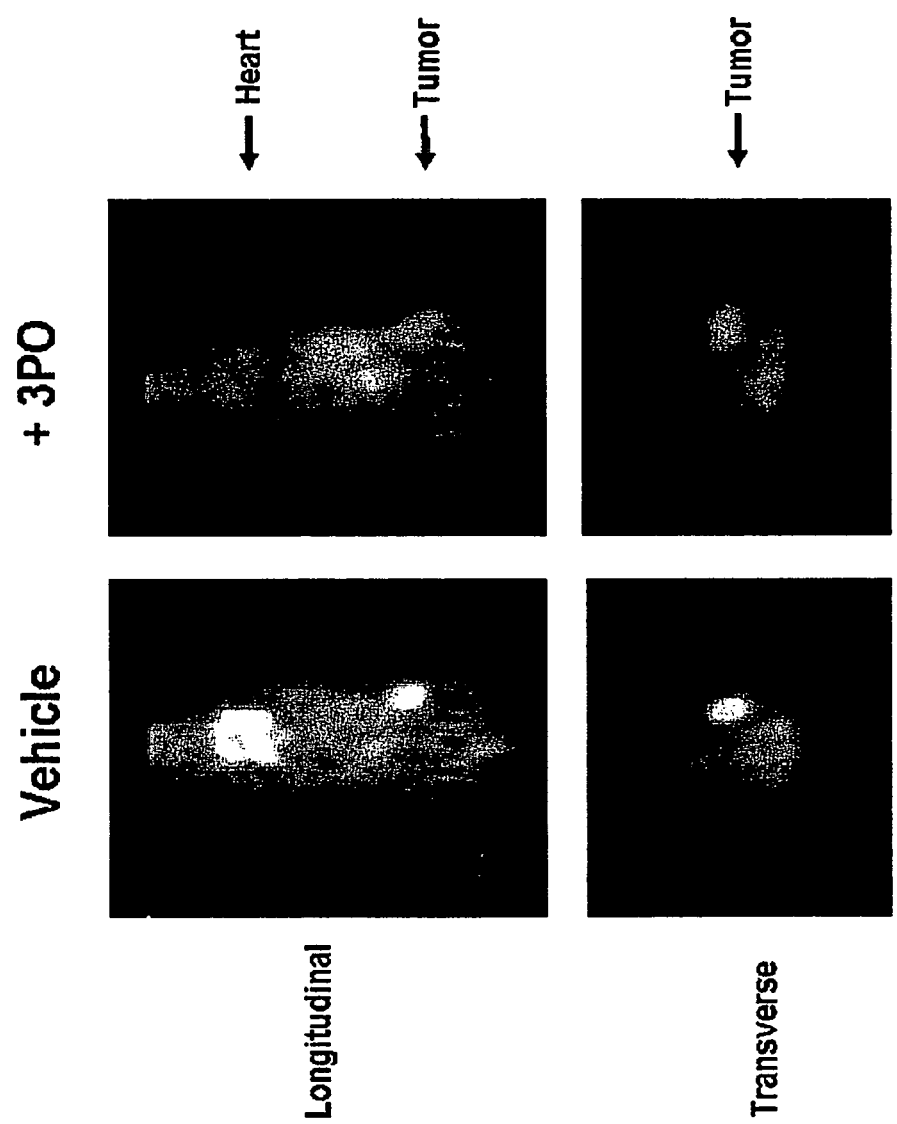
FIG. 22 shows micro-positron emission tomography (MicroPet) images of $^{18}$F-2-deoxy-glucose uptake in mice bearing Lewis lung carcinoma zenografts. The mice were given an interperitoneal (i.p.) injection of either 50 µl DMSO (Vehicle) or 0.07 mg/g 3PO in DMSO (+3PO) thirty minutes prior to i.p. injection with 150 µCurie $^{18}$F-fluoro-2-deoxy-glucose. Arrows indicate the position of the heart and the tumor xenograft within the right flank.

To further study the effects of compound 1, glucose uptake in compound 1-treated mice was studied using micro-positron emission tomography (micro-Pet). Lewis lung carcinoma xenograft bearing mice were given an i.p. injection of 50 μL of DMSO or of 0.07 mg/g compound 1 in DMSO. Thirty minutes after this first injection, each mouse was injected i.p. with 2-($^{18}$F)-fluoro-2-deoxy-glucose ($^{18}$F-2-DG; 150 μCurie, 100 μL in H$_2$O). After another 15 minutes, the mice were anesthetized with 2% isoflurane in oxygen and transferred to a R-4 Rodent Scanner Micro-PET (CTI Concorde Microsystems, Inc.; Knoxville, Tenn., United States of America). Three mice from each group (i.e., compound 1 treated or control) were studied. FIG. 22 shows micro-PET images taken of a representative compound 1-treated mouse and a representative control group mouse.

As shown in FIG. 22, compound 1 treatment significantly diminished $^{18}$F-2-DG uptake within the xenograft as compared to the control group mouse. A difference in cardiac $^{18}$F-2-DG uptake was also observed between the compound 1-treated and control group mice. Echocardiograms were performed as described in Dawn et al., *Proc. Natl. Acad. Aci., U.S.A.*, 102, 3766-3771 (2005). Echocardiographic examination of cardiac function in the mice revealed no acute changes in ejection fraction (Control (Vehicle): 69%±4%; Compound 1: 71%±6%). Thus the difference in cardiac glucose uptake does not appear to be the result of cardiotoxicity of compound 1. Overall, it appears that 1 targets PFK2 activity in vivo resulting in a reduced glycolytic phenotype.

Example 8

Effects of Compound 1 on Tumor Mass in Transgenic Mice

Transgenic MMTV-Neu Breast Tumor mice develop breast adenocarcinomas within 3-4 months of birth and rely on the transgenic expression of oncogenic Neu under the control of the mouse mammary tumor virus promoter/enhancer. These mice more closely mimic human cancer relative to xenograft models as a result of the insidious nature of their tumor growth and the lack of artifact caused by tissue culture conditions.

Figure 23:
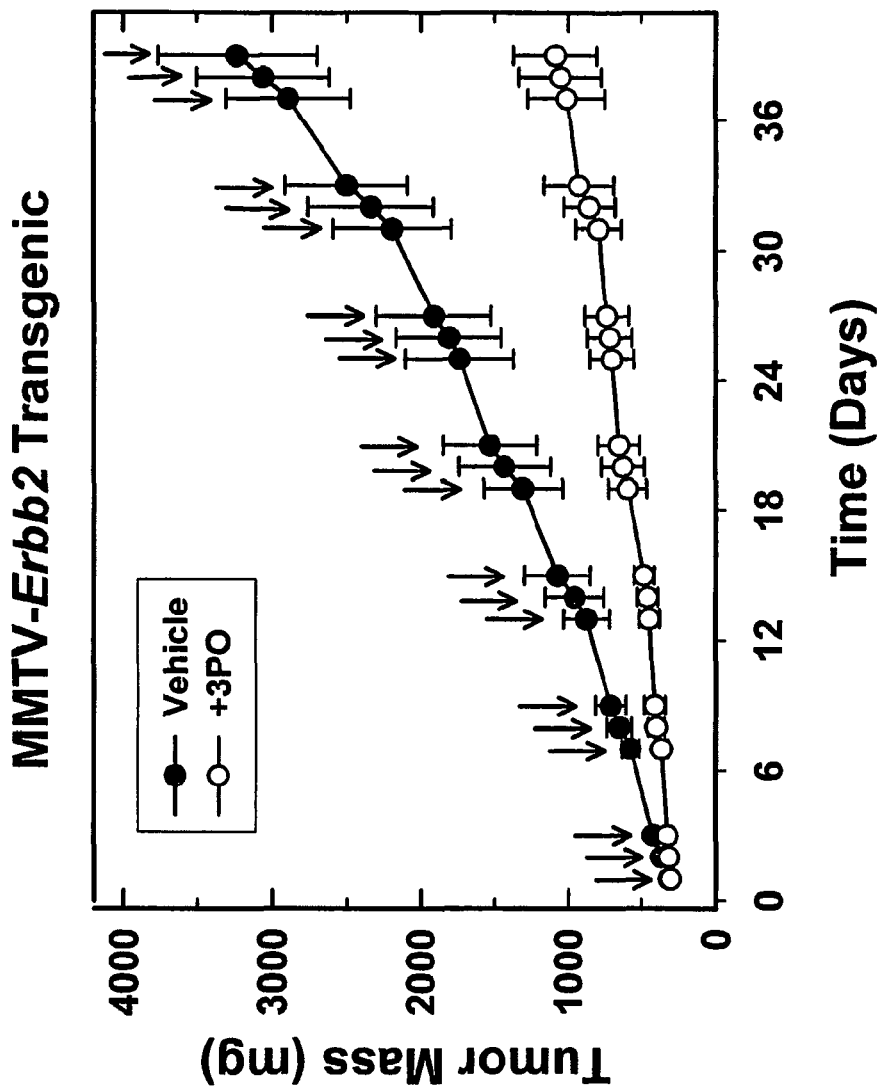
FIG. 23 is a graph showing the effects of 3PO treatment on tumor mass in four month old transgenic MMTV-Neu breast tumor mice. The mice were randomized into two groups with equal tumor burden. One group (+3PO) was administered 3PO (0.07 mg/g in DMSO; i.p.) daily in repeating cycles of 3 days on (indicated by arrows) and 3 days off. The second group (Vehicle) were injected with DMSO only.
Figure 24:
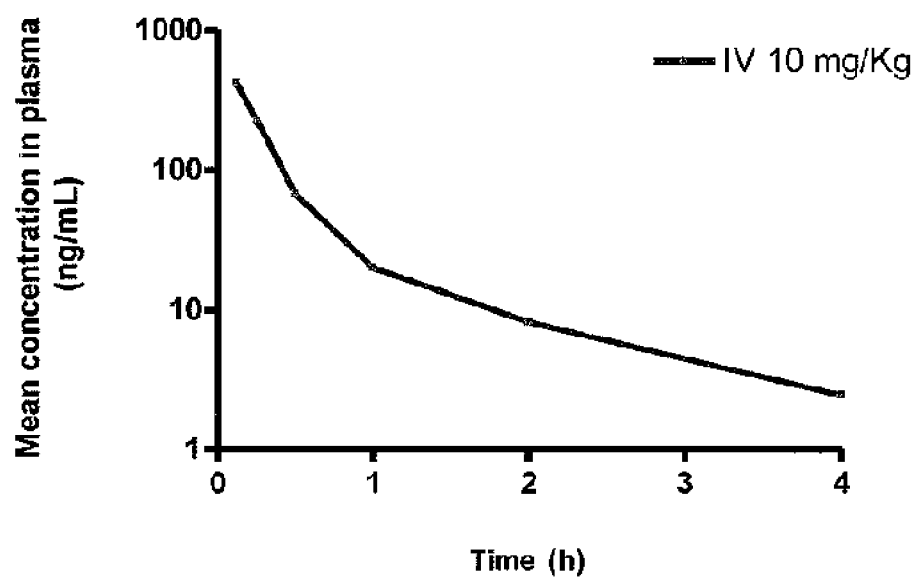
FIG. 24 is a graph showing time vs. plasma concentration, pharmacokinetic profile of ACT-PFK-070 in BalbC mice (IV dosing, 1 mg/kg).
Figure 25:
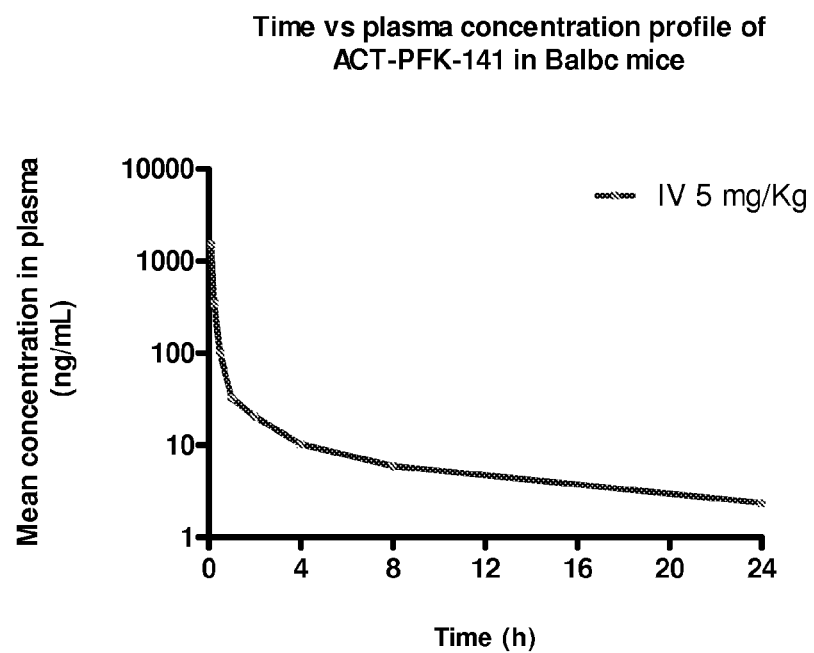
FIG. 25 is a graph showing time vs. plasma concentration, pharmacokinetic profile of ACT-PFK-141 in Balbc mice (IV dosing, 5 mg/kg).
Figure 26:
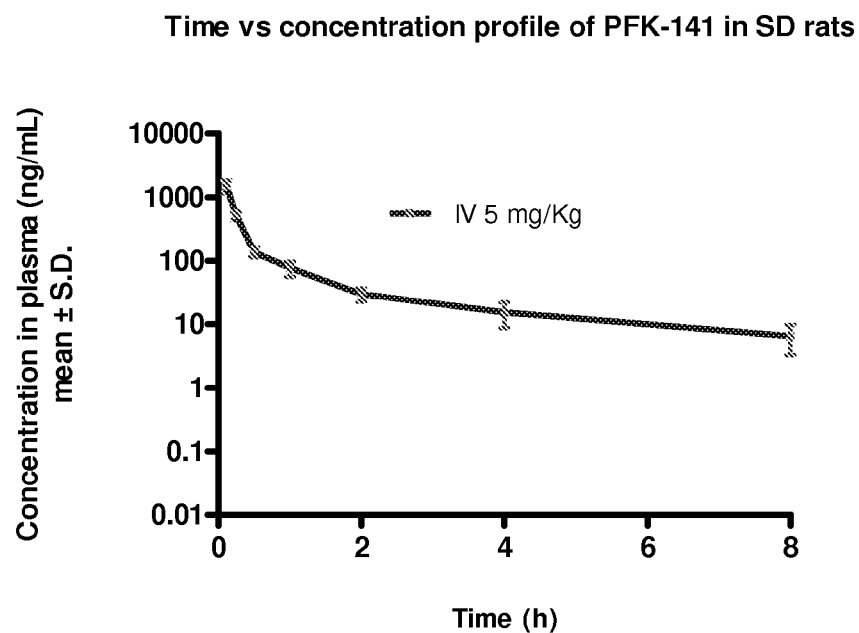
FIG. 26 is a graph showing time vs. plasma concentration, pharmacokinetic profile of ACT-PFK-141 in male Sprague-Dawley rats (IV dosing, 5 mg/kg).
Figure 27:
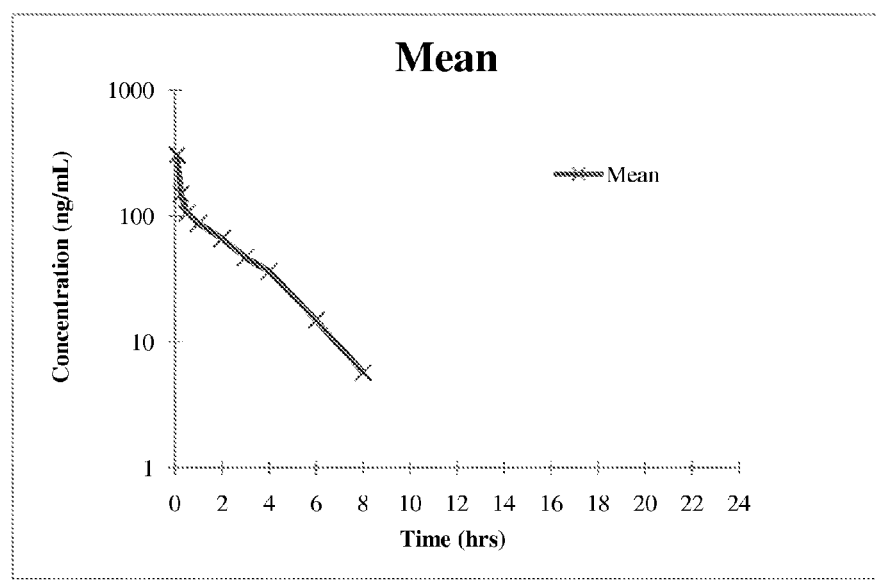
FIG. 27 is a graph showing time vs. plasma concentration, pharmacokinetic profile of ACT-PFK-141 in Beagle dogs (IV dosing, 5 mg/kg).
Figure 28:
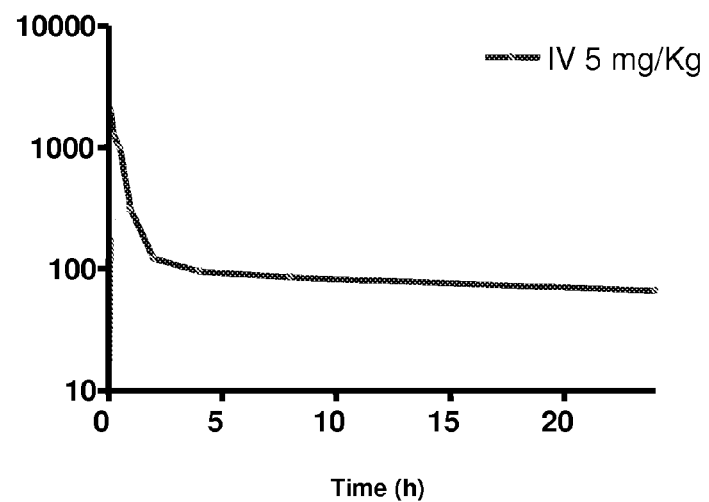
FIG. 28 is a graph showing time vs. plasma concentration, pharmacokinetic profile of ACT-PFK-151 in Balbc mice (IV dosing, 5 mg/kg).
Figure 29:
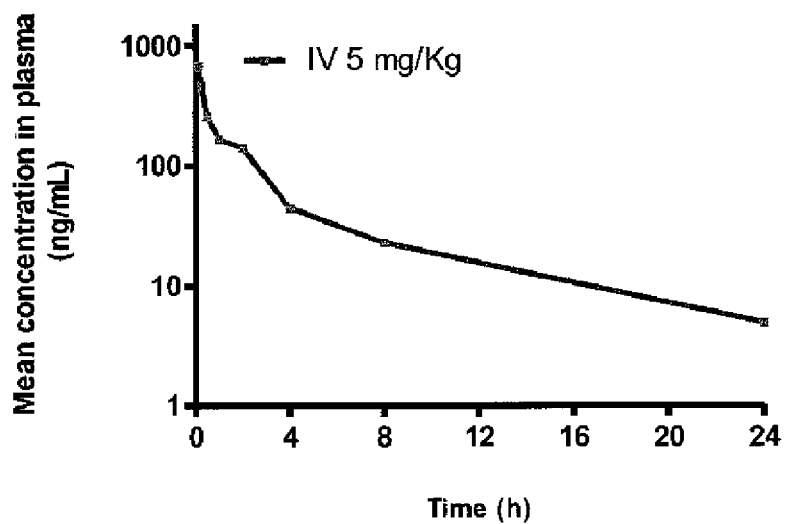
FIG. 29 is a graph showing time vs. plasma concentration, pharmacokinetic profile of ACT-PFK-154 in Balbc mice (IV dosing, 5 mg/kg).

To determine the effects of compound 1 on transgenic MMTV-Neu breast tumor mice, the relative tumor frequency and bulk in the transgenic mice was determined after 4 months and the mice were randomized into two groups with equal tumor burden. One group of mice were administered compound 1 daily in repeating cycles of 3 days on, 3 days off (0.07 mg/gm in DMSO; intraperitoneal administration; see arrows; until tumor mass exceeds 10% of body mass). Control mice were injected with vehicle control (DMSO alone). Tumor masses were determined according to the following established formula: mass (mg)=(width, mm$^2$×length, m)/2. To obtain statistical significance (assuming an alpha value of 0.05 and power of 0.90), each group required 30 mice. The effects of treatment with compound 1 on tumor mass over time is shown in FIG. 23.

Example 9

Synthesis of Compounds of Formulae (VI) and (VII)

The compounds of Formulae (VI) and (VII) are prepared using the general methods described below in Scheme I or II, together with synthetic methods known to one skilled in the art of organic synthesis and variations thereon. One skilled in the art will appreciate that quinolyl and aryl moieties may be unsubstituted or substituted with any number of suitable substituents. In some embodiments, the quinolyl moiety can be an isoquinolyl moiety. Such variations are within the purview of the ordinary skilled artisan.

As briefly described in the schemes below, the compounds Formulae (VI) and (VII) can be prepared by the reaction of the corresponding quinoline and isoquinoline aldehydes (1, 5, and 7) with the corresponding substituted or unsubstituted acetyl derivatives (2) in the presence of a suitable base. Alternatively, aldehydes may also be reacted with phosphorylidene derivatives (3) to give the desired products of Formulae (VI), or (VII).

The aldehydes are either commercially available or prepared from the methods known in the art. In some cases the aldehydes are prepared by the oxidation of the corresponding methyl compounds, as known in the art.

The acetyl derivatives and phosphorylidene derivatives (2 and 3) are also generated from procedures known in the art.

General scheme 1:

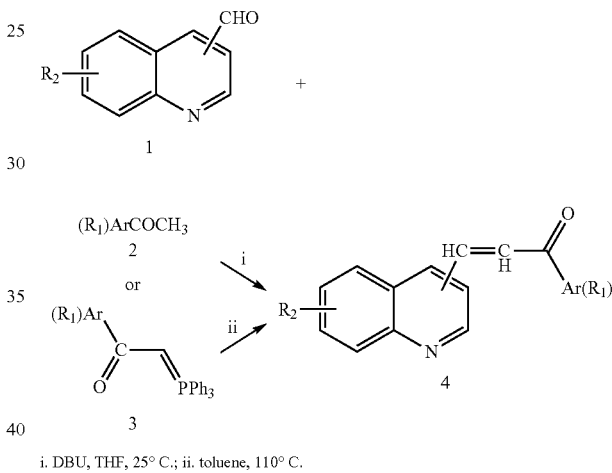

i. DBU, THF, 25° C.; ii. toluene, 110° C.

General scheme 2:

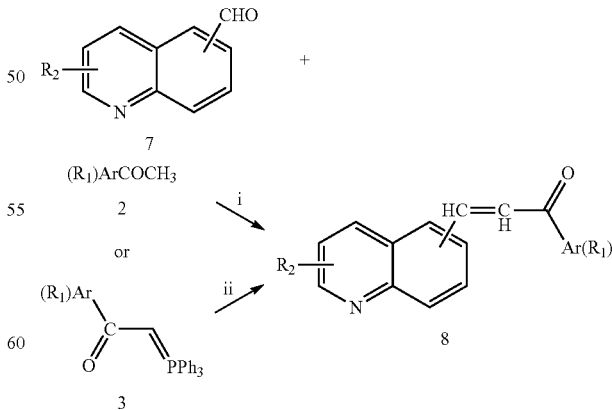

i. DBU, THF, 25° C.; ii. toluene, 110° C.

TABLE 2

Formula (VI) Exemplary Compounds

| Compound Number | MW | Structure & Name & NMR Data |
|---|---|---|
| ACT-PFK-013 | 260.3 | 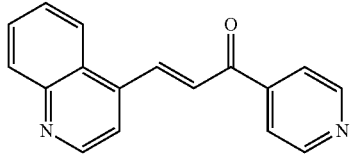 [SMILES: O=C(/C=C/c1ccnc2ccccc12)c1ccncc1]<br>1-Pyridin-4-yl-3-quinolin-4-yl-propenone. $^1$H NMR (300 MHz, CDCl$_3$): δ 9.00 (d, J = 4.5 Hz, 1H), 8.90 (d, J = 5.7 Hz, 2H), 8.59 (d, J = 15.6 Hz, 1H), 8.21-8.17 (m, 2H), 7.86-7.78 (m, 3H), 7.69-7.62 (m, 3H). |
| ACT-PFK-014 | 260.3 | 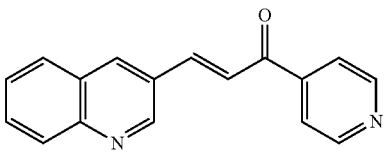 [SMILES: O=C(/C=C/c1cnc2ccccc2c1)c1ccncc1]<br>1-Pyridin-4-yl-3-quinolin-3-yl-propenone. $^1$H NMR (300 MHz, DMSO-d$_6$): δ 9.46 (s, 1H), 8.89-8.88 (m, 3H), 8.24-8.19 (m, 1H), 8.09-7.97 (m, 5H), 7.87-7.82 (m, 1H), 7.71-7.66 (m, 1H). |
| ACT-PFK-35 | 260.3 | 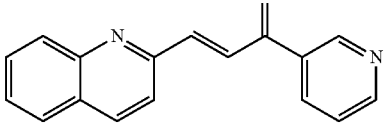<br>1-Pyridin-3-yl-3-quinolin-2-yl-propenone. $^1$H NMR (300 MHz, CDCl$_3$): δ 9.35-9.34 (m, 1H), 8.84 (dd, J = 4.8 Hz, 1.8 Hz, 1H), 8.36 (dt J = 8.1 Hz, 1.8 Hz, 1H), 8.24 (d, J = 8.4 Hz, 1H), 8.18-8.13 (m, 2H), 7.99 (d, J = 15.3 Hz, 1H), 7.87-7.84 (m, 1H). 7.69 (d, j +8.4 Hz, 1H), 7.63-7.6 (m, 1H), 7.58-7.47 (m, 1H). |
| ACT-PFK-36 | 260.3 | 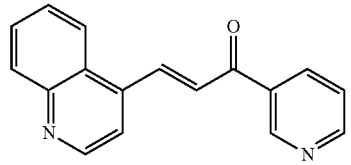 [SMILES: O=C(/C=C/c1ccnc2ccccc12)c1cccnc1]<br>1-Pyridin-3-yl-3-quinolin-4-yl-propenone. $^1$H NMR (300 MHz, CDCl$_3$): δ 9.24 (s, 1H), 8.93 (d, J = 4.5 Hz, 1H), 8.80-8.78 (m, 1H), 8.53 (d, J = 15.6 Hz, 1H), 8.29 (dt, J = 7.8 Hz, 2.1 Hz, 1H), 8.15-8.10 (m, 2H), 7.76-7.70 (m, 1H), 7.66-7.57 (m, 3H), 7.47-7.42 (m, 1H). |
| ACT-PFK-048 | 260.3 | 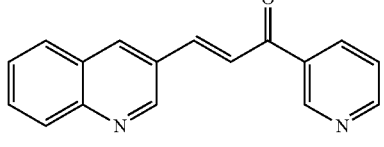<br>1-Pyridin-3-yl-3-quinolin-3-yl-propenone. $^1$H NMR (300 MHz, CdCl$_3$): δ 9.31 (s, 1 H), 9.25-9.20 (m, 1 H), 8.91-8.84 (m, 1H), 8.39-8.33 (m, 2 H), 8.15 (d, J = 9.0 Hz, 1H), 8.06-8.00 (m, 1H), 7.92-7.87 (m, 1H), 7.84-7.75 (m, 2H), 7.71-7.66 (m, 1H), 7.64-7.56 (m, 1H). |

TABLE 2-continued

Formula (VI) Exemplary Compounds

| Compound Number | MW | Structure & Name & NMR Data |
|---|---|---|
| ACT-PFK-052 | 309.3 | 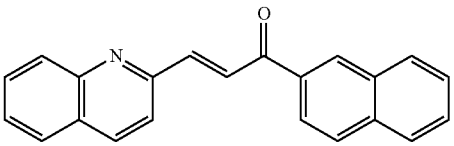 [SMILES: O=C(/C=C/c1ccc2ccccc2n1)c1ccc2ccccc2c1]<br>1-Naphthalen-2-yl-3-quinolin-2-yl-propenone. $^1$H NMR (300 MHz, CdCl$_3$): δ 8.68 (s, 1 H), 8.35 (d, J = 15.6 Hz, 1 H), 8.24 (d, J = 8.4 Hz, 1 H), 8.20-8.17 (m, 2 H), 8.06-7.91 (m, 4 H), 7.85 (d, J = 8.1 Hz, 1 H), 7.78-7.75 (m, 1 H), 7.72 (d, J = 8.4 Hz, 1 H), 7.64-7.56 (m, 3 H). |
| ACT-PFK-053 | 309.4 | 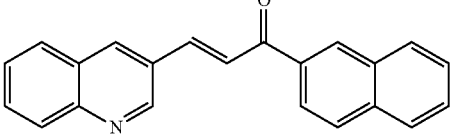<br>1-Naphthalen-2-yl-3-quinolin-3-yl-propenone. $^1$H NMR (300 MHz, CDCl$_3$): δ 9.28-9.27 (m, 1H), 8.61 (s, 1H), 8.41-8.40 (m, 1H), 8.17-8.14 (m, 2 H), 8.08-8.02 (m, 2H), 8.00-7.96 (m, 2H), 7.94-7.90 (m, 2H), 7.82-7.76 (m, 1H), 7.65-7.54 (m, 3H). |
| ACT-PFK-055 | 260.3 | 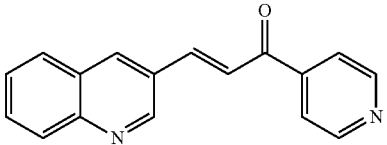 [SMILES: O=C(/C=C/c1cnc2ccccc2c1)c1ccncc1]<br>1-Pyridin-4-yl-3-quinolin-3-yl-propenone. $^1$H NMR (300 MHz, CDCl$_3$): δ 9.01-8.99 (m, 1H), 8.89-8.87 (m, 2H), 8.66-8.57 (m, 2H), 8.24 (d, J = 8.4, 1H), 8.01 (d, J = 7.2, 1H), 7.85-7.77 (m, 3H), 7.61-7.51 (m, 2H). |
| ACT-PFK-066 | 276.3 | 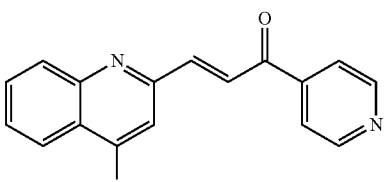<br>3-(4-Hydroxy-quinolin-2-yl)-1-pyridin-4-yl-propenone. $^1$H NMR (300 MHz, DMSO-d$_6$): δ 11.95 (s, 1H), 8.88 (d, J = 5.7 Hz, 2H), 8.21-8.16 (m, 1H), 8.08-7.97 (m, 3H), 7.89 (d, J = 7.8 Hz, 1H), 7.58 (t, J = 7.5 Hz, 1H), 7.40-7.38 (m, 1H), 7.28-7.23 (m, 1H), 7.15 (s, 1H). |
| ACT-PFK-067 | 276.3 | 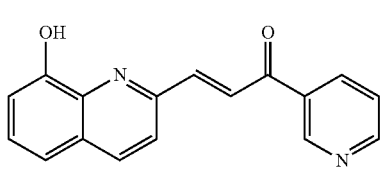 [SMILES: O=C(/C=C/c1ccc2cccc(O)c2n1)c1cccnc1]<br>3-(8-Hydroxy-quinolin-2-yl)-1-pyridin-3-yl-propenone. $^1$H NMR (300 MHz, DMSO-d$_6$): δ 9.94 (s, 1 H), 9.49 (d, J = 1.5, 1H), 8.90 (dd, J = 4.8 Hz, 1.5 Hz, 1H), 8.72 (d, J = 15.3 Hz, 1H), 8.56-8.53 (m, 1H), 8.43 (d, J = 8.4 Hz, 1H), 8.06 (d, J = 8.4 Hz, 1H), 7.97 (d, J = 15.3 H, 1H), 7.69-7.66 (m, 1H), 7.54-7.49 (m, 1H), 7.45-7.42 (m, 1H), 7.17-7.15 (m, 1H). |

TABLE 2-continued

Formula (VI) Exemplary Compounds

| Compound Number | MW | Structure & Name & NMR Data |
|---|---|---|
| ACT-PFK-068 | 273.3 | 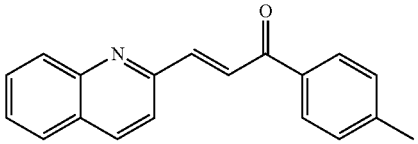 [SMILES: Cc1ccc(C(=O)/C=C/c2ccc3ccccc3n2)cc1]<br>3-Quinolin-2-yl-1-p-tolyl-propenone. ¹H NMR (300 MHz, DMSO-d₆): δ 8.49 (d, J = 8.4 Hz, 1 H), 8.33 (d, J = 15.6 Hz, 1H), 8.23 (d, J = 8.7 Hz, 1H), 8.12-8.08 (m, 3H), 8.04-8.02 (m, 1H), 7.86-7.80 (m, 2H), 7.69-7.64 (m, 1H), 7.43 (d, J = 7.8 Hz, 2H), 2.43 (s, 3H). |
| ACT-PFK-070 | 276.28 | 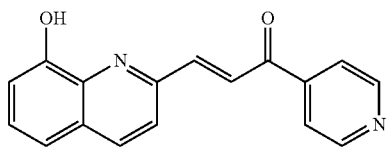 [SMILES: O=C(/C=C/c1ccc2cccc(O)c2n1)c1ccncc1]<br>3-(8-Hydroxy-quinolin-2-yl)-1-pyridin-4-yl-propenone. ¹H NMR (300 MHz, DMSO-d₆): δ 9.92 (s, 1 H), 8.92-8.90 (m, 2 H), 8.60 (d, = 15.3 H$_Z$, 1H), 8.43 (d, J = 8.4 H$_Z$, 1 H), 8.09-8.05 (m, 3 H), 7.95 (d, J = 15.6 Hz, 1 H), 7.54-7.49 (m, 1 H), 7.44-7.42 (m, 1 H), 7.18-7.14 (m, 1 H). |
| ACT-PFK-071 | 289.3 | 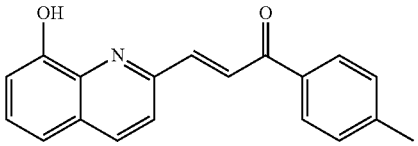 [SMILES: Cc1ccc(C(=O)/C=C/c2ccc3cccc(O)c3n2)cc1]<br>3-(8-Hydroxy-quinolin-2-yl)-1-p-tolyl-propenone. ¹H NMR (300 MHz, DMSO-d₆): δ 9.99 (s, 1H), 8.73 (d, J = 15.0, 1H), 8.49-8.46 (m, 1H), 8.26-7.94 (m, 4H), 7.51-7.45 (m, 4H), 7.23 (m, 1H), 2.58 (s, 3H) |
| ACT-PFK-073 | 289.3 | 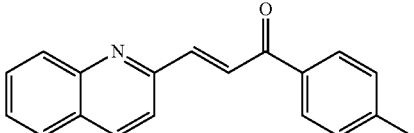<br>3-(4-Hydroxy-quinolin-2-yl)-1-p-tolyl-propenone. ¹H NMR (300 MHz, DMSO-d₆): δ 11.91 (s, 1H), 8.14-8.00 (m, 4H), 7.88 (d, J = 8.1 Hz, 1H), 7.57 (t, J = 7.5 Hz, 1H), 7.42-7.37 (m, 3H), 7.25 (t, J = 7.5 Hz, 1H), 7.11 (s, 1H), 2.42 (s, 3H) |
| ACT-PFK-076 | 259.3 | 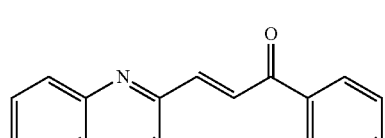<br>1-Phenyl-3-quinolin-2-yl-propenone. ¹H NMR (300 MHz, DMSO-d₆): δ 8.51-8.48 (m, 1 H), 8.33 (d, J = 15.9 H$_Z$, 1H), 8.26-8.11 (m, 2 H), 8.04-7.85 (m, 3 H), 7.83-7.60 (m, 5 H), 7.58-7.54 (m, 1H). |

TABLE 2-continued

Formula (VI) Exemplary Compounds

| Compound Number | MW | Structure & Name & NMR Data |
|---|---|---|
| ACT-PFK-085 | 260.3 | 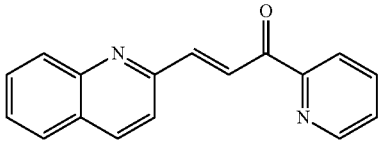 [SMILES: O=C(/C=C/c1ccc2ccccc2n1)c1ccccn1]<br>1-Pyridin-2-yl-3-quinolin-2-yl-propenone. $^1$H NMR (300 MHz, CdCl$_3$): δ 8.79-8.78 (m, 1 H), 8.73 (d, J = 15.9 H$_Z$, 1 H), 8.23-8.10 (m, 4 H), 7.93-7.81 (m, 3 H), 7.77-7.74 (m, 1 H), 7.59-7.49 (m, 2 H). |
| ACT-PFK-086 | 275.3 | 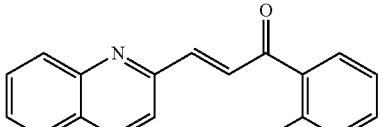<br>1-(2-Hydroxy-phenyl)-3-quinolin-2-yl-propenone. $^1$H NMR (300 MHz, DMSO-d$_6$): δ 11.97 (s, 1 H), 8.81-8.52 (m, 1 H), 8.40 (d, J = 15.6 H$_Z$, 1 H), 8.24-8.03 (m, 4 H), 7.93-7.82 (m, 2 H), 7.75-7.57 (m, 2 H), 7.33-7.18 (m, 2 H). |
| ACT-PFK-087 | 275.3 | 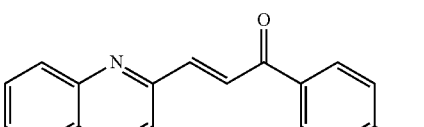<br>1-(4-Hydroxy-phenyl)-3-quinolin-2-yl-propenone. It was prepared using scheme-5. (Mixture of geometrical isomer). $^1$H NMR (300 MHz, DMSO-d$_6$): δ 10.54-10.27 (1H), 8.49-8.19 (m, 2H), 8.13-8.015 (m, 2H), 7.89-7.49 (m, 5H), 7.15-6.83 (m, 3H). |
| ACT-PFK-088 | 274.3 | 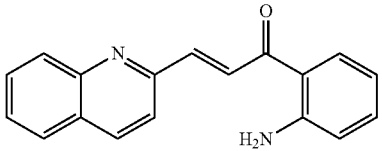 [SMILES: Nc1ccccc1C(=O)/C=C/c1ccc2ccccc2n1]<br>1-(2-Amino-phenyl)-3-quinolin-2-yl-propenone. $^1$H NMR (300 MHz, DMSO-d$_6$): δ 8.47-8.34 (m, 2H), 8.09-7.88 (m, 2H), 7.78-7.62 (m, 3H), 7.51-7.37 (m, 3H), 7.35-6.96 (m, 2H), 6.85-6.76 (m, 1H), 6.63-6.52 (m, 1H). |
| ACT-PFK-089 | 274.3 | 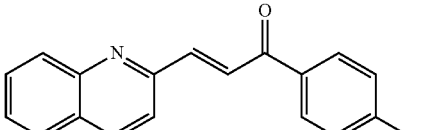<br>1-(4-Amino-phenyl)-3-quinolin-2-yl-propenone. $^1$H NMR (300 MHz, DMSO-d$_6$): δ 8.47 (d, J = 8.7 Hz, 1H), 8.29 (d, J = 15.6 Hz, 1H), 8.20 (d, J = 8.7 Hz, 1H), 8.09-7.95 (m, 4H), 7.84-7.77 (m, 2H) 7.72-7.63 (m, 2H), 6.67-6.65 (m, 2H). |

TABLE 2-continued

Formula (VI) Exemplary Compounds

| Compound Number | MW | Structure & Name & NMR Data |
|---|---|---|
| ACT-PFK-091 | 302.3 | 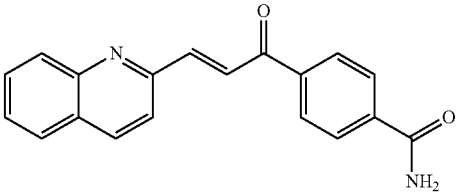 [SMILES: NC(=O)c1ccc(C(=O)/C=C/c2ccc3ccccc3n2)cc1]<br>4-(3-Quinolin-2-yl-acryloyl)-benzamide. ¹H NMR (300 MHz, DMSO-d₆): δ 8.47 (d, J = 8.4 Hz, 1H), 8.28 (d, J = 15.6 Hz, 1H), 8.18 (d, J = 8.7 Hz, 1H), 8.09-7.95 (m, 4H), 7.83-7.71 (m, 2H), 7.67-7.64 (m, 1H), 6.65 (d, 8.4 Hz, 2H), 6.27 (s, 2H). |
| ACT-PFK-094 | 303.3 | 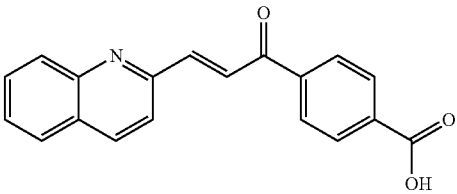 [SMILES: O=C(O)c1ccc(C(=O)/C=C/c2ccc3ccccc3n2)cc1]<br>4-(3-Quinolin-2-yl-acryloyl)-benzoic acid. ¹H NMR (300 MHz, DMSO-d₆): δ 8.50 (d, J = 8.7 Hz, 1H), 8.33 (d, J = 15.6 Hz, 1H), 8.25 (t, J = 8.1 Hz, 3H), 8.15-8.02 (m, 4H), 7.89-7.80 (m, 2H), 7.70-7.65 (m, 1H). |
| ACT-PFK-141 | 274.3 | 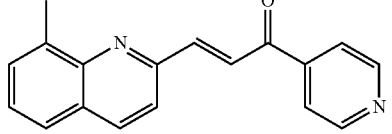<br>3-(8-Methyl-quinolin-2-yl)-1-pyridin-4-yl-propenone. ¹H NMR (300 MHz, DMSO-d₆): δ 8.89 (d, J = 3.90 Hz, 2H), 8.46 (d, J = 8.70 Hz, 1H), 8.28-8.20 (m, 2H), 8.02 (d, J = 4.20 Hz, 2H), 7.96-7.83 (m, 2H), 7.67 (, J = 6.60 Hz, 1H), 7.57-7.52 (m, 1H), 2.78 (s, 3H). HPLC-99.5% (area percentage) |
| ACT-PFK-143 | 278.3 | 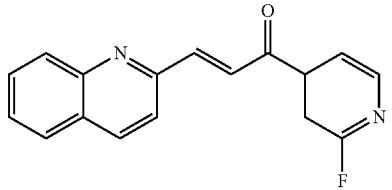 [SMILES: O=C(/C=C/c1ccc2ccccc2n1)C1C=CN=C(F)C1]<br>1-(2-Fluoro-pyridin-4-yl)-3-quinolin-2-yl-propenone. ¹H NMR (300 MHz, CDCl₃): δ 8.46 (d, J = 4.80 Hz, 1H), 8.25 (d, J = 8.40 Hz, 1H), 8.15 (d, J = 8.70 Hz, 2H), 8.09-7.96 (m, 2H), 7.87-7.79 (m, 3H), 7.69-7.58 (m, 2H), 7.52 (s, 1H). HPLC-99.3% (area percentage) |
| ACT-PFK-145 | 278.3 | 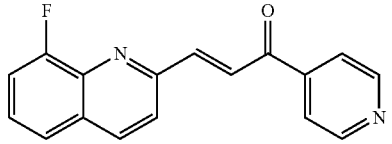 [SMILES: O=C(/C=C/c1ccc2cccc(F)c2n1)c1ccncc1]<br>3-(8-Fluoro-quinolin-2-yl)-1-pyridin-4-yl-propenone. ¹H NMR (300 MHz, DMSO-d₆): δ 8.89 (d, J = 4.50 Hz, 2H), 8.59 (d, J = 8.40 Hz, 1H), 8.35-8.23 (m, 2H), 8.02 (d, J = 4.50 Hz, 2H), 7.90-7.85 (m, 2H), 7.68-7.64 (m, 3H). HPLC- 99.5% (area percentage) |

TABLE 2-continued

Formula (VI) Exemplary Compounds

| Compound Number | MW | Structure & Name & NMR Data |
|---|---|---|
| ACT-PFK-149 | 276.3 | 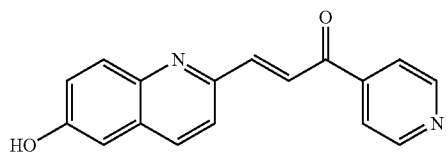 [SMILES: O=C(/C=C/c1ccc2cc(O)ccc2n1)c1ccncc1]
3-(6-Hydroxy-quinolin-2-yl)-1-pyridin-4-yl-propenone
¹H NMR (300 MHz, DMSO-d₆): δ 10.33 (s, 1H), 8.87 (d, J = 4.5 Hz, 2H) 8.26 (d, J = 8.70 Hz, 1H), 8.17-8.11 (m, 2H), 8.00 (d, J = 4.50 Hz, 2H), 7.94 (d, J = 9.0 Hz, 1H), 7.83 (d, J = 15.9 Hz, 1H), 7.37 (d, J = 9.0 Hz, 1H), 7.19 (s, 1H). |
| ACT-PFK-151 | 289.3 | 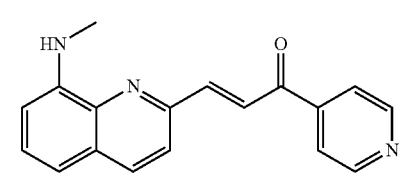 [SMILES: CNc1cccc2ccc(/C=C/C(=O)c3ccncc3)nc12]
3-(8-Methylamino-quinolin-2-yl)-1-pyridin-4-yl-propenone
¹H NMR (300 MHz, DMSO-d₆): δ 8.89 (s, 2H) 8.40-8.26 (m, 2H), 8.05-7.89 (m, 4H), 7.43 (s, 1H), 7.04 (br s, 2H), 6.62 (d, J = 6.30 Hz, 1H), 2.96 (s, 3H). |
| ACT-PFK-154 | 274.3 | 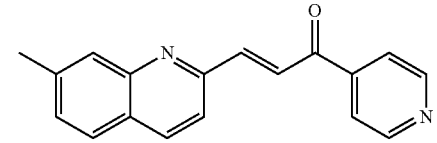 [SMILES: Cc1ccc2ccc(/C=C/C(=O)c3ccncc3)nc2c1]
3-(7-Methyl-quinolin-2-yl)-1-pyridin-4-yl-propenone
¹H NMR (300 MHz, DMSO-d₆): δ 8.89 (d, J = 4.20 Hz, 2H) 8.58 (d, J = 8.70 Hz, 1H), 8.27-8.20 (m, 2H), 8.02 (d, J = 4.20 Hz, 2H), 7.95-7.86 (m, 2H), 7.73-7.68 (m, 1H), 7.50 (d, J = 6.90 Hz, 1H), 2.70 (s, 3H). |
| ACT-PFK-157 | 289.3 | 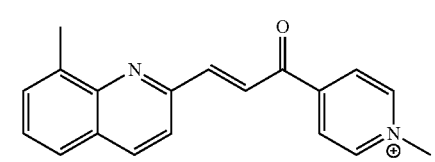 [SMILES: Cc1cccc2ccc(/C=C/C(=O)c3cc[n+](C)cc3)nc12]
1-Methyl-4-[3-(8-methyl-quinolin-2-yl)-acryloyl]-pyridinium
¹H NMR (300 MHz, DMSO-d₆): δ 9.25 (d, J = 6.60 Hz, 2H) 8.67 (d, J = 6.00 Hz, 2H), 8.51 (d, J = 4.80 Hz, 1H), 8.26-8.20 (m, 2H), 7.96-7.86 (m, 2H), 7.70 (d, J = 6.90 Hz, 1H), 7.61-7.56 (m, 1H), 4.45 (s, 3H), 2.79 (s, 3H). |

TABLE 3

Formula (VII) Exemplary Compounds

| Compound Number | MW | Structure & Name & NMR Data |
|---|---|---|
| ACT-PFK-037 | 260.3 | 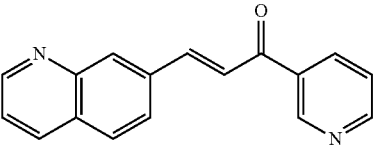 [SMILES: O=C(/C=C/c1ccc2cccnc2c1)c1cccnc1] 1-Pyridin-3-yl-3-quinolin-7-yl-propenone. $^1$H NMR (300 MHz, CDCl$_3$): δ 9.31-9.30 (m, 1 H), 9.01 (dd, J = 4.2 Hz, 1.8 Hz, 1H), 8.94 (d, J = 15.9 H$_Z$, 1H), 8.82 (dd, J = 4.8 Hz, 1.8 Hz, 1H), 8.35 (dt, J = 7.8 Hz, 2.1 Hz, 1H), 8.22-8.19 (m, 1H), 8.13-8.10 (m, 1H), 8.02 (d, j = 15.9 Hz, 1H), 7.94-7.91 (m, 1H), 7.62 (t, J = 7.8 Hz, 1H), 7.51-7.50 (m, 2H). |
| ACT-PFK-038 | 260.3 | 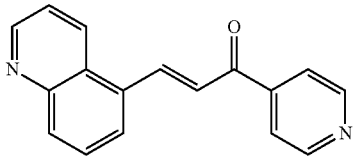 [SMILES: O=C(/C=C/c1cccc2ncccc12)c1ccncc1] 1-Pyridin-4-yl-3-quinolin-5-yl-propenone. $^1$H NMR (300 MHz, CDCl$_3$): δ 9.01-8.99 (m, 1 H), 8.89-8.87 (m, 2H), 8.66-8.57 (m, 2H), 8.24 (d, J = 8.4 H$_Z$, 1H), 8.01 (d, J = 7.2 Hz, 1H), 7.85-7.77 (m, 3H), 7.61-7.53 (m, 2H). |
| ACT-PFK-039 | 260.3 | 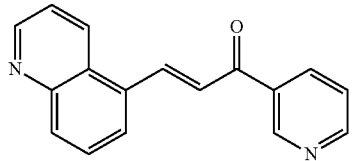 [SMILES: O=C(/C=C/c1cccc2ncccc12)c1cccnc1] 1-Pyridin-3-yl-3-quinolin-5-yl-propenone. $^1$H NMR (300 MHz, CDCl$_3$): δ 9.30 (d, J = 1.5 Hz, 1H), 9.00 (d, d, J = 1.8 Hz, J = 1.5 Hz, 1H), 8.84 ((d, d, J = 1.8 Hz, J = 1.8 Hz, 1H), 8.67-8.59 (m, 2 H), 8.36 (dt, J = 4.2 Hz, J = 3.6 Hz, 1 H), 8.23 (d, J = 8.4 Hz, 1 H), 8.01 (d, J = 7.2 Hz, 1 H), 7.82-7.77 (m, 1 H), 7.64 (d, J = 15.3 Hz, 1 H), 7.55-7.51 (m, 2 H). |
| ACT-PFK-047 | 260.3 | 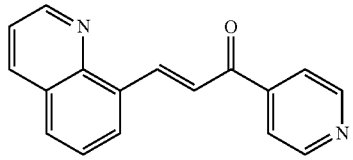 [SMILES: O=C(/C=C/c1cccc2cccnc12)c1ccncc1] 1-Pyridin-4-yl-3-quinolin-8-yl-propenone. $^1$H NMR (300 MHz, CDCl$_3$): δ 9.02-9.00 (m, 1H), 8.94 (d, J = 16.2 Hz, 1H), 8.86-8.84 (m, 2H), 8.23-8.19 (m, 1H), 8.11 (d, J = 7.5 Hz, 1H), 7.94-7.89 (m, 2H), 7.84-7.82 (m, 2H), 7.65-7.60 (m, 1H), 7.52-7.47 (m, 1H). |

TABLE 3-continued

Formula (VII) Exemplary Compounds

| Compound Number | MW | Structure & Name & NMR Data |
|---|---|---|
| ACT-PFK-051 | 309.3 | 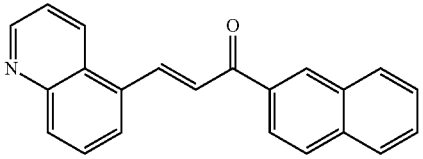 [SMILES: O=C(/C=C/c1cccc2ncccc12)c1ccc2ccccc2c1] 1-Naphthalen-2-yl-3-quinolin-5-yl-propenone. $^1$H NMR (300 MHz, CdCl$_3$): δ 9.01-8.99 (m, 1 H), 8.68-8.61 (m, 3 H), 8.24-8.21 (m, 1 H), 8.18-8.15 (m, 1 H), 8.07-7.97 (m, 3 H), 7.94-7.91 (m, 1 H), 7.87-7.78 (m, 2 H), 7.67-7.64 (m, 2 H), 7.59-7.56 (m, 1H). |

Example 10

Inhibition of Cancer Cell Proliferation

The ability of the compounds described herein to kill or inhibit the proliferation of cancer cells was measured using either the MTT assay, the Alamar Blue assay, or the Cell Titer Glow® assay using 48 or 72 hours exposure. Results for different cancer cell lines are shown in the Tables 4 and 5 below and demonstrate that these compounds inhibit cancer cell proliferation at low nanomolar concentrations across many types of cancer cell lines. The procedures are briefly described below. Cells of the desired tumor cell line were plated at 2×10$^5$ cells/ml in 96 well plates. Twice the indicated concentrations of the compounds of the invention were added to cells the following day in an equal volume of media. 72 hours later, cells were lysed and subjected to ATP determination using the CellTiter Glo-Luminescent Cell Viability Assay kit (Promega, Madison, Wis.). Experiments were done in triplicate. When using the MTT assay or the Alamar blue assay, the experimental conditions are essentially similar; at the end of the incubation period, 20 microl of the MTT solution is added per well and the samples are incubated for an additional four hours, rinsed and the absorbance at 570 nm measured. Results for the inhibition of cells proliferation are reported as IC50 as commonly done (the concentration leading to a 50% inhibition of proliferation of the cell population) and are listed in the Tables below. Table 4 lists the IC50 for the compounds of the invention in several cell lines including Jurkat, Calu-6, NCI-H82, U937, or NCI-H1437 cancer cell lines. Table 5 lists the IC50 of PFK-070 in a panel of 10 cell lines.

TABLE 4

IC$_{50}$ values (Alamar Blue assay, 72 hours).

| | IC$_{50}$s for Compounds of the Invention (μM) | | | | |
|---|---|---|---|---|---|
| Cpd | Jurkat | U937 | NCI-H82 | Calu-6 | NCI-H1437 |
| ACT-PFK-013 | 1 | | | | |
| ACT-PFK-014 | 4 | | | | |
| ACT-PFK-035 | 2.5 | | | | |
| ACT-PFK-036 | 2.5 | | | | |
| ACT-PFK-037 | 2.5 | | | | |
| ACT-PFK-038 | 1 | | | | |
| ACT-PFK-039 | 1 | | | | |
| ACT-PFK-047 | 14 | | | | |

TABLE 4-continued

IC$_{50}$ values (Alamar Blue assay, 72 hours).

IC$_{50}$s for Compounds of the Invention (μM)

| Cpd | Jurkat | U937 | NCI-H82 | Calu-6 | NCI-H1437 |
|---|---|---|---|---|---|
| ACT-PFK-048 | 17 | | | | |
| ACT-PFK-055 | >100 | | | | |
| ACT-PFK-066 | 2.4 | 1.3 | | 3.8 | |
| ACT-PFK-067 | 3.1 | 0.83 | | 2.4 | |
| ACT-PFK-068 | 5.5 | 1.6 | | 4.8 | |
| ACT-PFK-070 | 1.3 | 3.6 | 4 | 7.4 | 29.3 |
| ACT-PFK-071 | 4.8 | 1.9 | | 5 | |
| ACT-PFK-073 | 0.6 | 0.2 | | 0.8 | |
| ACT-PFK-076 | 6.4 | 2.5 | 4 | 3.3 | |
| ACT-PFK-085 | 4.9 | 2.9 | 2.7 | 6.9 | |
| ACT-PFK-086 | 80.5 | 19.3 | 22.5 | >100 | |
| ACT-PFK-087 | 3.7 | 1.3 | 2.3 | 1.6 | |
| ACT-PFK-088 | >100 | 17.2 | 38.5 | >100 | |
| ACT-PFK-089 | 4.2 | 1.6 | 0.9 | 2.1 | |
| ACT-PFK-091 | 0.6 | 0.4 | 0.7 | 0.2 | 4.2 |
| ACT-PFK-141 | 0.9 | | 1.1 | | 5.4 |
| ACT-PFK-143 | 1.7 | | 2.6 | | 4.3 |
| ACT-PFK-145 | 0.9 | | 1.5 | | 4.7 |
| ACT-PFK-149 | | | | | |
| ACT-PFK-151 | | | | | |
| ACT-PFK-154 | | | | | |

TABLE 5

IC$_{50}$ values (MTT assay, 48 hours) in a panel of cell lines using PFK-070.

| Cell line | PFK-070 IC$_{50}$ (nM) |
|---|---|
| H22 | 3945 |
| CT26 | 2060 |
| U87MG | 1678 |
| SK-N-SH | 1455 |
| LnCap | 1276 |
| A549 | 2685 |
| MiaPaca | 275 |
| BX-PC-3 | 1180 |
| BT474 | 952 |
| SK-BR-3 | 1598 |

Example 11

Inhibition of PFKFB3, the Recombinant Protein

The inducible bifunctional 6-Phosphofructo-2-kinase/fructose2,6-biphosphatase enzyme (PFKFB3) was expressed and purified in order to determine if the compounds of the invention inhibits its enzymatic activity. PFKFB3 was prepared by expression in *E. coli* and purified by GST column and column chromatography. SDS Page coumassie staining gels indicated that purity was high (>95%). The recombinant protein was pure and active as determined by the results of a kinase activity assay commercially available (Adapta® Kinase assay). The same assay was used to determine the inhibition of the protein and the results are shown in Table 6 below (IC50 values).

These results confirmed that the compounds of the invention are potent inhibitors of PFKFB3, have low nanomolar IC$_{50}$s, and interact with PFKFB3 and inhibit its enzymatic activity.

TABLE 6

IC$_{50}$s values for PFKFB3 Inhibitors of the present invention (nM).

| Analog | IC$_{50\ EArec}$ (nM) |
|---|---|
| PFK-141 | 210 ± 51 |
| PFK-143 | 654 ± 95 |
| PFK-145 | 294 ± 38 |
| PFK-149 | 811 ± 266 |
| PFK-151 | 289 ± 56 |
| PFK-154 | 622 ± 39 |

Example 12

Microsomal Stability in Human Liver Microsomes

Microsomal stability in vitro in different biologic media (liver microsomes, S9 fraction, hepatocytes) and species is ascertained to evaluate the rate at which a compound undergoes metabolism in the experimental in vitro conditions. Results for some compounds of the invention after a 60 minutes incubation period in human liver microsomes are shown in the Table 7 below. Results show that the rate of metabolism in vitro can be controlled as substitutions lead to metabolism rates varying between 20% and 100%. Experimental conditions are briefly described here: the stability in human liver microsomes of several compounds was done over 24 hours at 37° C. using pooled mixed gender human liver microsomes. These liver microsomes were prepared at 1.0 mg/ml of microsomal protein in a 100 mM potassium phosphate pH 7.4 buffer with 1 mM NADPH. The media was incubated at 37° C. with the compound in solution in DMSO. The concentration of the compound was followed by LC/MS-MS as a function of time. Samples were assayed at t=0 and 60 minutes. Testosterone was used as a positive control. The same experiment was performed with mouse, rat or dog liver microsomes instead of human liver microsomes.

TABLE 7

Human Liver Microsomal stability results.

| | Mean metabolized (%) | |
|---|---|---|
| Analog | 0 min | 30 min |
| ACT-PFK-070 | 0 | 85.5 |
| ACT-PFK-091 | 0 | 90.3 |
| ACT-PFK-092 | 0 | 89 |
| ACT-PFK-141 | 0 | 56.7 |
| ACT-PFK-145 | 0 | 70.9 |
| ACT-PFK-151 | 0 | 82 |
| ACT-PFK-154 | 0 | 57 |

Example 13

Solubility and Solution Stability Results

Chemical properties of the compounds of the invention were investigated, mainly the solubility in several solvents and pharmaceutically accepted excipients or dosing solutions and the stability of these solutions. Surprisingly, results show that the solubility of compounds of the invention, despite some structural similarities to PFK-015, have enhanced solubility profiles that enable treating cancer patients via parenteral administration. The increase in solubility when comparing the effect of chemical substituents is unpredictable and surprising if one compares the solubility values of PFK-070 to PFK-091 and PFK-070 to PFK-141 and 145 in a dosing solution that could be used to treat cancer patients (See Table 8A below). Briefly, selected compounds of the invention are dissolved in a small volume of the solvents/excipients of interest (Cremophor, or Cremophor:etoh or Tween80:etoh) at room temperature and diluted 1:9 in saline and left at room temperature for over 8 or 24 hours. Both the physical (absence of a precipitate) and the chemical stability (less than 5% degradation) of the solutions are measured (observation and HPLC after filtration). Studies using Cremophor and D5W (5% glucose in water for injection) or Tween 80 with either Saline or D5W lead to comparable results in solubility and similar differences between PFK-015 and the compounds of the invention.

Furthermore, the solution stability of the compounds was investigated and it was discovered that, in normal conditions, they lack the appropriate solution stability as they undergo a rapid photoisomerization; this lack of solution stability is such that methods to prevent these compounds from reacting in solutions are necessary if these compounds are to be used as chemotherapeutic agents for the treatment of cancer patients. Surprisingly, this lack of solution stability was not previously appreciated; the use of amber or dark glass containers, amber IV bags and tubings, or amber over-pouches, limits the UV-visible exposure and thus prevent this photo reaction from happening as seen in Table 8B.

TABLE 8A

Solubility results (mg/ml) after 24 hours at room temperature

| Cpd | Cre:EtOH:Saline[1] |
|---|---|
| PFK-070 | 0.1 |
| PFK-091 | 0.2 |
| PFK-141 | 0.8 |
| PFK-145 | 0.1 |
| PFK-149 | 0.3 |
| PFK-151 | 1.9 |
| PFK-154 | — |

[1]Cre:EtOH:Saline is a 5:5:90 mixture where Cre stands for Cremophor

TABLE 8B

Solubility stability results (mg/ml) in normal conditions and in amber containers.

| | Cre:EtOH:Saline[1] Cpd PFK-070, HCl (mg/ml) | |
|---|---|---|
| | Clear Vials | Amber Vials |
| 0 hrs | 1.0 | 1.0 |
| 2 hrs | 0.9 Change in color | No change |
| 4 hrs | 0.8 Change in color | No change |
| 8 hrs | <0.7 Change in color | No change |

TABLE 9

Solubility Profile in Aqueous Media, 015 analogs.

| | Solubility (mg/mL) at 23° C. | | |
|---|---|---|---|
| | pH = 3 | pH = 5 | pH = 7 |
| PFK-141, HCl | — | 1.7 | 1.9 |
| PFK-154, HCl | | 2.4 | 3.4 |

Example 14

Inhibition of 2-Deoxyglucose Uptake

Inhibition of PFKFB3 results in inhibiting glycolysis. Several feedback or feedforward activation and inhibition mechanisms exist so that, by a feedback mechanism, inhibiting the activity of PFKFB3 might inhibit glucose uptake by cells. An assay was developed to determine if there was inhibition of glucose uptake following exposure to the compounds on the invention. Briefly, Jurkat cells were plated at $1 \times 10^5$/mL in RPMI 1640 supplemented with 10% fetal bovine serum and 50 µg/mL gentamicin sulfate. Cells were immediately treated with vehicle or 0.5 µmol/L of the compound of the invention for 3 hours and subsequently placed in glucose-free RPMI 1640 for 30 min. $^{14}$C-2-deoxyglucose (0.25 µCi/mL; Perkin Elmer) was added for an additional 60 min and cells were then washed three times with ice-cold RPMI 1640 containing no glucose. Cell lysates were collected in 500 µL of 0.1% SDS, and scintillation counts (counts/min) were measured on 400 µL of lysate. Counts were normalized to protein concentration.

Results shown in Table 10 indicate that there is rapid and quantitative inhibition of glucose uptake by cells treated with PFKFB3 inhibitors.

TABLE 10

Percentage of Deoxyglucose Uptake Inhibition.

| Compound | Concentration | % Inhibition in 2-Deoxyglucose Uptake |
|---|---|---|
| PFK-070 | 0.5 µM | 45 |
| PFK-076 | 0.5 µM | 27 |
| PFK-085 | 0.5 µM | 31 |
| PFK-090 | 0.5 µM | 13 |
| PFK-091 | 0.5 µM | 11 |

Example 15

Pharmacokinetics

The pharmacokinetic parameters for several compounds listed above were determined in mice following IV (intravenous), IP (intraperitoneal), or PO (per os) administration and in rats or dogs. A typical study design includes, six Balbc male mice 7 to 8 weeks old. For instance, a dose of 10 mg/kg was administered IV using a 5% DMSO/90% Captisol (20% in water) solution or other pharmaceutically acceptable parenteral and oral formulations. Blood samples were collected at different intervals. Plasma samples were extracted and analyzed using an LC-MS/MS method. Similar protocols were used for the rats (Sprague Dawley rats) or dogs (beagles) PK studies; in the case of dogs PK studies, the number of animals per group was three. Pharmacokinetic results are illustrated in FIGS. 24 to 29 that show time versus plasma concentration in either Balbc mice, Sprague-Dawley rats, or Beagle dogs for PFK-070, 092, and 141, 151, and 154.

Example 16

Efficacy Studies

The activity of several compounds of the invention was investigated in vivo in tumor models. Several tumor models were used in these studies (the Lewis Lung Carcinoma or LLC model, the human glioblastoma xenograft U87MG tumor model, or the murine CT26 colon cancer model). The experimental protocol for the U87MG study is described below. Subsequent to subcutaneous inoculation of tumor cells, tumors started to develop and once tumors reached the desired volume of 150-200 mm$^3$ on average, treatment was initiated. Tumor volume was monitored in both groups and the average for both the control and treatment groups three times a week as well as body weights.

Figure 30:
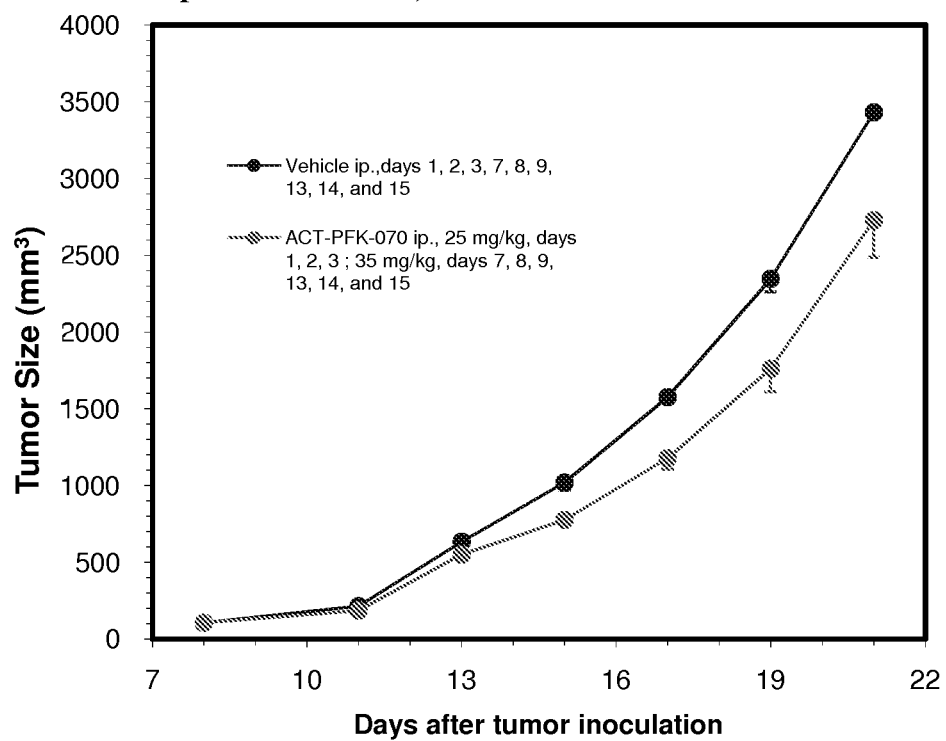
FIG. 30 shows the average tumor volume as a function of time in for control group and treatment groups in the Lewis Lung Carcinoma (ACT-PFK-070 dosed IP at 25 mg/kg).
Figure 31:
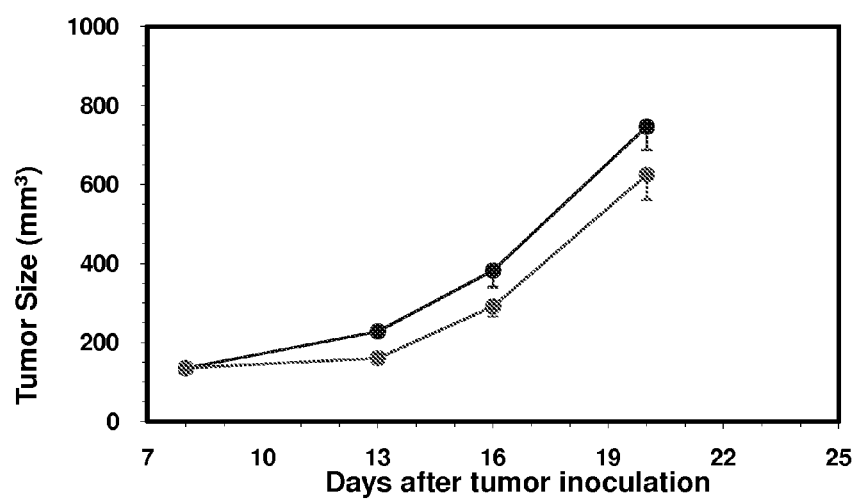
FIG. 31 shows the average tumor volume as a function of time for control group and treatment group in the U87MG glioblastoma multiforme model (ACT-PFK-141 dosed IP at 20 mg/kg).
Figure 32:
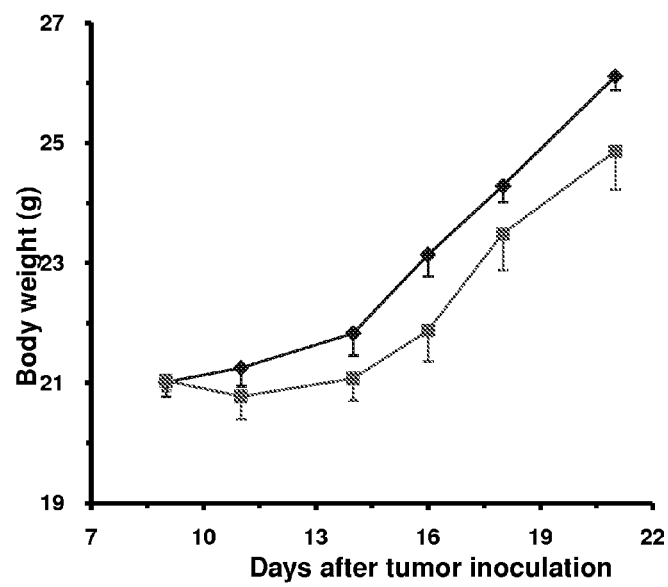
FIG. 32 shows the average tumor volume as a function of time for control group and treatment group in the CT26 colon tumor model (ACT-PFK-141 dosed IP at 20 mg/kg).

Briefly, athymic nude mice at 7-8 weeks of age were used for the study. Mice were housed in microisolator housing, with food and water provided as libitum, and quarantined for 4 days prior to the initiation of the study. U87MG cells were maintained in McCoy's 5A medium supplemented with 10% fetal bovine serum and 2 mM glutamine. Cells at 80% confluence were harvested using 0.25% trypsin/EDTA solution, washed once with PBS and resuspended in a mixture of serum-free medium/Matrigel (1:1 by volume) at a density of $3 \times 10^6$ cells/100 µl. 4 groups of 10 mice each were used in that experiment. U87MG cells suspended in 100 µl of a mixture of medium/Matrigel (1:1) were subcutaneously implanted in the right flank region. Animals were monitored for tumor growth daily after cell implantation. When tumor volumes reached approximately 150 mm3, mice were randomized into 2 groups of 8 mice each using only mice having tumor volumes closest to the mean value. Tumor volumes were measured using the formula $V=L \times W \times H \times \pi/6$, where L and W represent the longer and shorter diameters of the tumor and H represents the height of the tumor. Treatment began following randomization. ACT-PFK-092 was administered IP at a dose of 20 mg/kg on days 1, 3, 5, 7, 9, 11, and 13. Animals were observed for possible toxic effect from the drug treatment. Body weights were recorded and showed that the compounds were very well tolerated. Results are shown in FIGS. 30 to 32.

Similar protocols were used for the other studies using different models; differences might have included the use normal mice (C57Bcl6); administering larger number of cancer cells; including a positive control group; dosing using different routes of administration and different schedules or doses depending of the characteristics of the compounds tested. Results of several studies are shown and demonstrate that the compounds of the invention inhibit tumor growth in vivo in different tumor types.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A compound or an optical isomer or stereoisomer or racemic mixture thereof, the compound having the Formula:

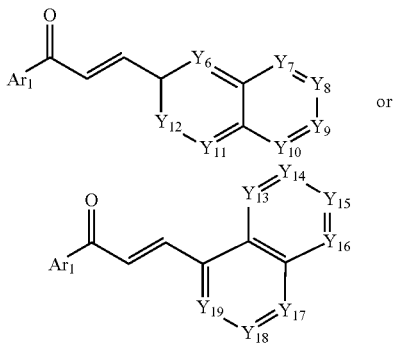

wherein $Ar_1$ is substituted or unsubstituted and is selected from the group consisting of phenyl, 2-pyridyl, 3-pyridyl, 4-pyridyl, 3,5-pyrimidinyl, and 2,4-pyrimidinyl, wherein $Ar_1$ substitutions are selected from the group consisting of H, F, Cl, OH, alkyl, O-alkyl, amino, alkylamino, carboxyl, aminocarbonyl, alkylaminocarbonyl, and combinations thereof;

$Y_6$, $Y_{11}$ and $Y_{12}$, are independently selected from the group consisting of N and CR, wherein when one of $Y_6$, $Y_{11}$, or $Y_{12}$ is N, the other two are CR;

$Y_{17}$, $Y_{18}$, and $Y_{19}$ are independently selected from the group consisting of N and CR, wherein when one of $Y_{17}$, $Y_{18}$, or $Y_{19}$ is N, the other two are CR;

each of $Y_7$, $Y_8$, $Y_9$, $Y_{10}$, $Y_{13}$, $Y_{14}$, $Y_{15}$, and $Y_{16}$ is CR; and each R is independently selected from the group consisting of H, F, OH, alkyl, amino, alkylamino, carboxyl, aminocarbonyl, alkylaminocarbonyl, and combinations thereof.

2. A compound selected from the group consisting of:
1-Naphthalen-2-yl-3-quinolin-2-yl-propenone;
1-Naphthalen-2-yl-3-quinolin-3-yl-propenone;
3-(4-Hydroxy-quinolin-2-yl)-1-pyridin-4-yl-propenone;
3-(8-Hydroxy-quinolin-2-yl)-1-pyridin-3-yl-propenone;
3-Quinolin-2-yl-1-p-tolyl-propenone;
3-(8-Hydroxy-quinolin-2-yl)-1-pyridin-4-yl-propenone;
3-(8-Hydroxy-quinolin-2-yl)-1-p-tolyl-propenone;
3-(4-Hydroxy-quinolin-2-yl)-1-p-tolyl-propenone;
1-Phenyl-3-quinolin-2-yl-propenone;
1-(2-Hydroxy-phenyl)-3-quinolin-2-yl-propenone;
1-(4-Hydroxy-phenyl)-3-quinolin-2-yl-propenone;
1-(2-Amino-phenyl)-3-quinolin-2-yl-propenone;
1-(4-Amino-phenyl)-3-quinolin-2-yl-propenone;
4-(3-Quinolin-2-yl-acryloyl)-benzamide;
4-(3-Quinolin-2-yl-acryloyl)-benzoic acid;
3-(8-Methyl-quinolin-2-yl)-1-pyridin-4-yl-propenone;
1-(2-Fluoro-pyridin-4-yl)-3-quinolin-2-yl-propenone;
3-(8-Fluoro-quinolin-2-yl)-1-pyridin-4-yl-propenone;
3-(6-Hydroxy-quinolin-2-yl)-1-pyridin-4-yl-propenone;
3-(8-Methylamino-quinolin-2-yl)-1-pyridin-4-yl-propenone;
3-(7-Methyl-quinolin-2-yl)-1-pyridin-4-yl-propenone; and
1-Methyl-4-[3-(8-methyl-quinolin-2-yl)-acryloyl]-pyridinium.

3. The compound

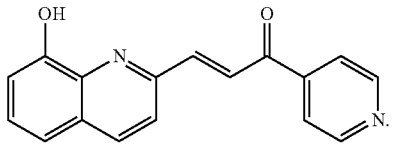 [SMILES: O=C(/C=C/c1ccc2cccc(O)c2n1)c1ccncc1]

* * * * *

SEQUENCE LISTING

```
<160> NUMBER OF SEQ ID NOS: 4

<210> SEQ ID NO 1
<211> LENGTH: 433
<212> TYPE: PRT
<213> ORGANISM: Homo sapiens

<400> SEQUENCE: 1

Ser Pro Thr Val Ile Val Met Val Gly Leu Pro Ala Arg Gly Lys Thr
1               5                   10                  15

Tyr Ile Ser Lys Lys Leu Thr Arg Tyr Leu Asn Trp Ile Gly Val Pro
            20                  25                  30

Thr Lys Val Phe Asn Val Gly Glu Tyr Arg Arg Glu Ala Val Lys Gln
        35                  40                  45

Tyr Ser Ser Tyr Asn Phe Phe Arg Pro Asp Asn Glu Glu Ala Met Lys
    50                  55                  60

Val Arg Lys Gln Cys Ala Leu Ala Ala Leu Arg Asp Val Lys Ser Tyr
65                  70                  75                  80

Leu Ala Lys Glu Gly Gly Gln Ile Ala Val Phe Asp Ala Thr Asn Thr
                85                  90                  95

Thr Arg Glu Arg Arg His Met Ile Leu His Phe Ala Lys Glu Asn Asp
            100                 105                 110

Phe Lys Ala Phe Phe Ile Glu Ser Val Cys Asp Asp Pro Thr Val Val
        115                 120                 125

Ala Ser Asn Ile Met Glu Val Lys Ile Ser Ser Pro Asp Tyr Lys Asp
    130                 135                 140

Cys Asn Ser Ala Glu Ala Met Asp Asp Phe Met Lys Arg Ile Ser Cys
145                 150                 155                 160
```

```
Tyr Glu Ala Ser Tyr Gln Pro Leu Asp Pro Asp Lys Cys Asp Arg Asp
                165                 170                 175
Leu Ser Leu Ile Lys Val Ile Asp Val Gly Arg Arg Phe Leu Val Asn
            180                 185                 190
Arg Val Gln Asp His Ile Gln Ser Arg Ile Val Tyr Tyr Leu Met Asn
        195                 200                 205
Ile His Val Gln Pro Arg Thr Ile Tyr Leu Cys Arg His Gly Glu Asn
    210                 215                 220
Glu His Asn Leu Gln Gly Arg Ile Gly Gly Asp Ser Gly Leu Ser Ser
225                 230                 235                 240
Arg Gly Lys Lys Phe Ala Ser Ala Leu Ser Lys Phe Val Glu Glu Gln
                245                 250                 255
Asn Leu Lys Asp Leu Arg Val Trp Thr Ser Gln Leu Lys Ser Thr Ile
            260                 265                 270
Gln Thr Ala Glu Ala Leu Arg Leu Pro Tyr Glu Gln Trp Lys Ala Leu
        275                 280                 285
Asn Glu Ile Asp Ala Gly Val Cys Glu Glu Leu Thr Tyr Glu Glu Ile
    290                 295                 300
Arg Asp Thr Tyr Pro Glu Glu Tyr Ala Leu Arg Glu Gln Asp Lys Tyr
305                 310                 315                 320
Tyr Tyr Arg Tyr Pro Thr Gly Glu Ser Tyr Gln Asp Leu Val Gln Arg
                325                 330                 335
Leu Glu Pro Val Ile Met Glu Leu Glu Arg Gln Glu Asn Val Leu Val
            340                 345                 350
Ile Cys His Gln Ala Val Leu Arg Cys Leu Leu Ala Tyr Phe Leu Asp
        355                 360                 365
Lys Ser Ala Glu Glu Met Pro Tyr Leu Lys Cys Pro Leu His Thr Val
    370                 375                 380
Leu Lys Leu Thr Pro Val Ala Tyr Gly Cys Arg Val Glu Ser Ile Tyr
385                 390                 395                 400
Leu Asn Val Glu Ser Val Cys Thr His Arg Glu Arg Ser Glu Asp Ala
                405                 410                 415
Lys Lys Gly Pro Asn Pro Leu Met Arg Arg Asn Ser Val Thr Pro Leu
            420                 425                 430
Ala

<210> SEQ ID NO 2
<211> LENGTH: 4497
<212> TYPE: DNA
<213> ORGANISM: Homo sapiens

<400> SEQUENCE: 2
agccaagccg gagaggaggc gagcggcagg gcctggtggc gagagcgcgg ctgtcactgc      60
gcccgagcat cccagagctt tccgagcgga cgagccggcc gtgccgggca tcccagcct    120 cgctaccctc gcagcacacg tcgagccccg cacaggcgag gtccggaac ttagcccaaa    180 gcacgtttcc cctggcagcg caggaaacgc ccggccgcgc gccggcgcac gccccctct    240 cctcctttgt tccgggggtc ggcggccgct ctcctgccag cgtcgggatc tcggccccgg    300
gaggcgggcc gtcgggcgca gccgcgaaga tgccgttgga actgacgcag agccgagtgc    360
agaagatctg ggtgcccgtg gaccacaggc ctcgttgcc cagatcctgt gggccaaagc    420
tgaccaactc ccccaccgtc atcgtcatgg tgggcctccc cgcccggggc aagacctaca    480
tctccaagaa gctgactcgc tacctcaact ggattggcgt ccccacaaaa gtgttcaacg    540 tcgggggagta tcgccgggag gctgtgaagc agtacagctc ctacaacttc ttccgccccg    600
```

```
acaatgagga agccatgaaa gtccggaagc aatgtgcctt agctgccttg agagatgtca        660
aaagctacct ggcgaaagaa gggggacaaa ttgcggtttt cgatgccacc aatactacta        720
gagagaggag acacatgatc cttcattttg ccaaagaaaa tgactttaag gcgttttca         780 tcgagtcggt gtgcgacgac cctacagttg tggcctccaa tatcatggaa gttaaaatct        840
ccagcccgga ttacaaagac tgcaactcgg cagaagccat ggacgacttc atgaagagga        900
tcagttgcta tgaagccagc taccagcccc tcgaccccga caaatgcgac agggacttgt        960
cgctgatcaa ggtgattgac gtgggccgga ggttcctggt gaaccgggtg caggaccaca       1020
tccagagccg catcgtgtac tacctgatga acatccacgt gcagccgcgt accatctacc       1080
tgtgccggca cggcgagaac gagcacaacc tccagggccg catcggggc gactcaggcc        1140 tgtccagccg gggcaagaag tttgccagtg ctctgagcaa gttcgtggag gagcagaacc       1200
tgaaggacct cgcgcgtgtgg accagccagc tgaagagcac catccagacg gccgaggcgc      1260
tgcggctgcc ctacgagcag tggaaggcgc tcaatgagat cgacgcgggc gtctgtgagg       1320
agctgaccta cgaggagatc agggacacct accctgagga gtatgcgctg cgggagcagg      1380
acaagtacta ttaccgctac cccaccgggg agtcctacca ggacctggtc cagcgcttgg       1440
agccagtgat catggagctg gagcggcagg agaatgtgct ggtcatctgc caccaggccg       1500
tcctgcgctg cctgcttgcc tacttcctgg ataagagtgc agaggagatg ccctacctga      1560
aatgccctct tcacaccgtc ctgaaactga cgcctgtcgc ttatggctgc cgtgtggaat       1620
ccatctacct gaacgtggag tccgtctgca cacaccggga gaggtcagag gatgcaaaga      1680
agggacctaa cccgctcatg agacgcaata gtgtcacccc gctagccagc ccgaaccca       1740 ccaaaaagcc tcgcatcaac agctttgagg agcatgtggc ctccacctcg gccgccctgc       1800
ccagctgcct gcccccggag gtgcccacgc agctgcctgg acaaaacatg aaaggctccc       1860
ggagcagcgc tgactcctcc aggaaacact gaggcagacg tgtcggttcc attccatttc       1920
catttctgca gcttagcttg tgtcctgccc tccgcccgag gcaaaacgta tcctgaggac       1980
ttcttccgga gagggtgggg tggagcagcg ggggagcctt ggccgaagag aaccatgctt       2040
ggcaccgtct gtgtcccctc ggccgctgga caccagaaag ccacgtgggt ccctggcgcc       2100
ctgcctttag ccgtgggcc cccacctcca ccctctgggt ttcctaggaa tgtccagcct       2160
cggagacctt cacaaagcct tgggagggtg atgagtgctg gtcctgacaa gaggccgctg       2220
gggacactgt gctgttttgt ttcgtttctg tgatctcccg gcacgtttgg agctgggaag       2280
accacactgg tggcagaatc ctaaaattaa aggaggcagg ctcctagttg ctgaaagtta       2340
aggaatgtgt aaaacctcca cgtgactgtt tggtgcatct tgacctggga agacgcctca       2400
tgggaacgaa cttggacagg tgttgggttg aggcctcttc tgcaggaagt ccctgagctg       2460
agacgcaagt tggctgggtg gtccacaccc tggctctcct gcaggtccac acaccttcca      2520
ggcctgtggc ctgcctccaa agatgtgcaa gggcaggctg gctgcacggg gagagggaag       2580
tattttgccg aaatatgaga actggggcct cctgctccca gggagctcca gggcccctct       2640
ctcctcccac ctggacttgg ggaaactga gaaacacttt cctggagctg ctggcttttg        2700 cactttttg atggcagaag tgtgacctga gagtcacacc ttctcttcag gaacgtagat       2760
gttggggtgt cttgccctgg ggggcttgga acctctgaag gtggggagcg gaacacctgg       2820
catccttccc cagcacttgc attaccgtcc ctgctcttcc caggtgggga cagtggccca       2880
agcaaggcct cactcgcagc cacttcttca agagctgcct gcacactgtc ttggagcatc       2940
tgccttgtgc ctggcactct gccggtgcct tgggaaggtc ggaagagtgg actttgtcct       3000
```

```
ggccttccct tcatggcgtc tatgacactt ttgtggtgat ggaaagcatg ggacctgtcg    3060
tctcagcctg ttggtttctc ctcattgcct caaaccctgg ggtaggtggg acgggggtc    3120 tcgtgcccag atgaaaccat ttggaaactc ggcagcagag tttgtccaaa tgacccttt    3180 caggatgtct caaagcttgt gccaaaggtc acttttcttt cctgccttct gctgtgagcc    3240
ctgagatcct cctcccagct caagggacag gtcctgggtg agggtgggag atttagacac    3300
ctgaaactgg gcgtggagag aagagccgtt gctgtttgtt ttttgggaag agcttttaaa    3360
gaatgcatgt ttttttcctg gttggaattg agtaggaact gaggctgtgc ttcaggtatg    3420
gtacaatcaa gtgggggatt ttcatgctga accattcaag ccctccccgc ccgttgcacc    3480
cactttggct ggcgtctgct ggagaggatg tctctgtccg cattcccgtg cagctccagg    3540
ctcgcgcagt tttctctctc tccctggatg ttgagtctca tcagaatatg tgggtagggg    3600
gtggacgtgc acgggtgcat gattgtgctt aacttggttg tattttcga tttgacatgg    3660 aaggcctgtt gctttgctct tgagaatagt ttctcgtgtc cccctcgcag gcctcattct    3720
ttgaacatca actctgaagt ttgatacaga taggggcttg atagctgtgg tccctctcc    3780 cctctgacta cctaaaatca ataccaaat acagaagcct tggtctaaca cgggacttt    3840 agtttgcgaa gggcctagat agggagagag gtaacatgaa tctggacagg gagggagata    3900
ctatagaaag gagaacactg cctactttgc aagccagtga cctgccttt gagggggacat    3960 tggacgggg ccggggcgg gggttgggtt tgagctacag tcatgaactt ttggcgtcta    4020
ctgattcctc caactctcca ccccacaaaa taacgggac caatattttt aactttgcct    4080
atttgttttt gggtgagttt ccccctcct tattctgtcc tgagaccacg ggcaaagctc    4140
ttcattttga gagagaagaa aaactgtttg gaaccacacc aatgatattt ttctttgtaa    4200
tacttgaaat ttatttttt attatttga tagcagatgt gctatttat tatttaatat    4260 gtataaggag cctaaacaat agaaagctgt agagattggg tttcattgtt aattggtttg    4320
ggagcctcct atgtgtgact tatgacttct ctgtgttctg tgtatttgtc tgaattaatg    4380
acctgggata taaagctatg ctagctttca aacaggagat gccttttcaga aatttgtata    4440 ttttgcagtt gccagaccaa taaaatacct ggttgaaata caaaaaaaaa aaaaaaa     4497
```

```
<210> SEQ ID NO 3
<211> LENGTH: 26
<212> TYPE: DNA
<213> ORGANISM: Artificial
<220> FEATURE:
<223> OTHER INFORMATION: synthetic

<400> SEQUENCE: 3
cttcatatgc cgttggaact gacgca                                           26

<210> SEQ ID NO 4
<211> LENGTH: 30
<212> TYPE: DNA
<213> ORGANISM: Artificial
<220> FEATURE:
<223> OTHER INFORMATION: synthetic

<400> SEQUENCE: 4
cttctcgagg tgtttcctgg aggagtcagc                                       30
```